US012105101B2

(12) United States Patent
Caughey et al.

(10) Patent No.: US 12,105,101 B2
(45) Date of Patent: *Oct. 1, 2024

(54) ASSAY FOR THE DETECTION OF ALPHA-SYNUCLEIN SEEDING ACTIVITY ASSOCIATED WITH SYNUCLEINOPATHIES

(71) Applicant: The U.S.A., as represented by the Secretary, Department of Health and Human Services, Bethesda, MD (US)

(72) Inventors: Byron Winslow Caughey, Hamilton, MT (US); Bradley Richard Groveman, Hamilton, MT (US); Christina Doriana Groveman, Hamilton, MT (US); Lynne DePuma Raymond, Hamilton, MT (US); Andrew Gregory Hughson, Hamilton, MT (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 197 days.

This patent is subject to a terminal disclaimer.

(21) Appl. No.: 17/708,560

(22) Filed: Mar. 30, 2022

(65) Prior Publication Data

US 2022/0291241 A1    Sep. 15, 2022

Related U.S. Application Data

(63) Continuation of application No. 16/652,804, filed as application No. PCT/US2018/052968 on Sep. 26, 2018, now Pat. No. 11,313,867.

(60) Provisional application No. 62/567,079, filed on Oct. 2, 2017.

(51) Int. Cl.
*G01N 33/68*  (2006.01)
*G01N 33/543*  (2006.01)

(52) U.S. Cl.
CPC ....... *G01N 33/6896* (2013.01); *G01N 33/543* (2013.01); *G01N 2800/2814* (2013.01)

(58) Field of Classification Search
CPC ............. G01N 33/6896; G01N 33/543; G01N 2800/2814; G01N 2800/2835; G01N 2800/7047
See application file for complete search history.

(56) References Cited

U.S. PATENT DOCUMENTS

| 8,216,788 B2 | 7/2012 | Caughey et al. |
| 2016/0077111 A1 | 3/2016 | Jara et al. |
| 2020/0232996 A1 | 7/2020 | Caughey et al. |

FOREIGN PATENT DOCUMENTS

WO    WO 2016/040907    3/2016

OTHER PUBLICATIONS

Fairfoul et al., Annals of Clinical and Translational Neurology, 2016; 3(10):812-818. (Year: 2016).*
Orru et al., Viruses, 2016, 8(140). (Year: 2016).*
Zarbiv et al., Neurobiology of Disease, 2014, 70:90-98. (Year: 2014).*
Berensmeier, "Magnetic Particles for the Separation and Purification of Nucleic Acids," *Appl. Microbiol. Biotechnol.*, vol. 73:495-504, 2006.
Fairfoul et al., "Alpha-Synuclein RT-QuIC in the CSF of Patients with Alpha-Synucleinopathies," *Ann. Clin. Transl. Neurol.*, vol. 3:812-818, 2016.
Kessler et al., "The N-Terminal Repeat Domain of α-Synuclein Inhibits β-Sheet and Amyloid Fibril Formation," *Biochem.*, vol. 42:672-678, 2003.
Koo et al., "Sequence Determinants Regulating Fibrillation of Human α-Synuclein," *Biochem. Biophys. Res. Comm.*, vol. 368:772-778, 2008.
Orrú et al., "Rapid and Sensitive RT-QuIC Detection of Human Creutzfeldt-Jakob Disease using Cerebrospinal Fluid," *mBio*, vol. 6:e02451-14, 2015.
Orrú et al., "Factors that Improve RT-QuIC Detection of Prion Seeding Activity," *Viruses*, vol. 8(140), 17pp., 2016.
Shahnawaz et al., "Development of a Biochemical Diagnosis of Parkinson Disease by Detection of a-Synuclein Misfolded Aggregates in Cerebrospinal Fluid," *JAMA Neurol* 74(2):163-172, 2017.
Metrick et al., "Million-fold sensitivity enhancement in proteopathic seed amplification assays for biospecimens by Hofmeister ion comparisons," *Proc Natl Acad Sci USA* 116(46):23029-23039, 2019.

* cited by examiner

*Primary Examiner* — Kimberly Ballard
*Assistant Examiner* — Stacey N Macfarlane
(74) *Attorney, Agent, or Firm* — Klarquist Sparkman, LLP

(57) ABSTRACT

Methods are disclosed for determining whether a subject has a synucleinopathy. Methods are also disclosed for detecting misfolded alpha synuclein (αSyn) in a biological sample or fraction thereof. These methods include the use of an αSyn seeding assay.

20 Claims, 26 Drawing Sheets

Specification includes a Sequence Listing.

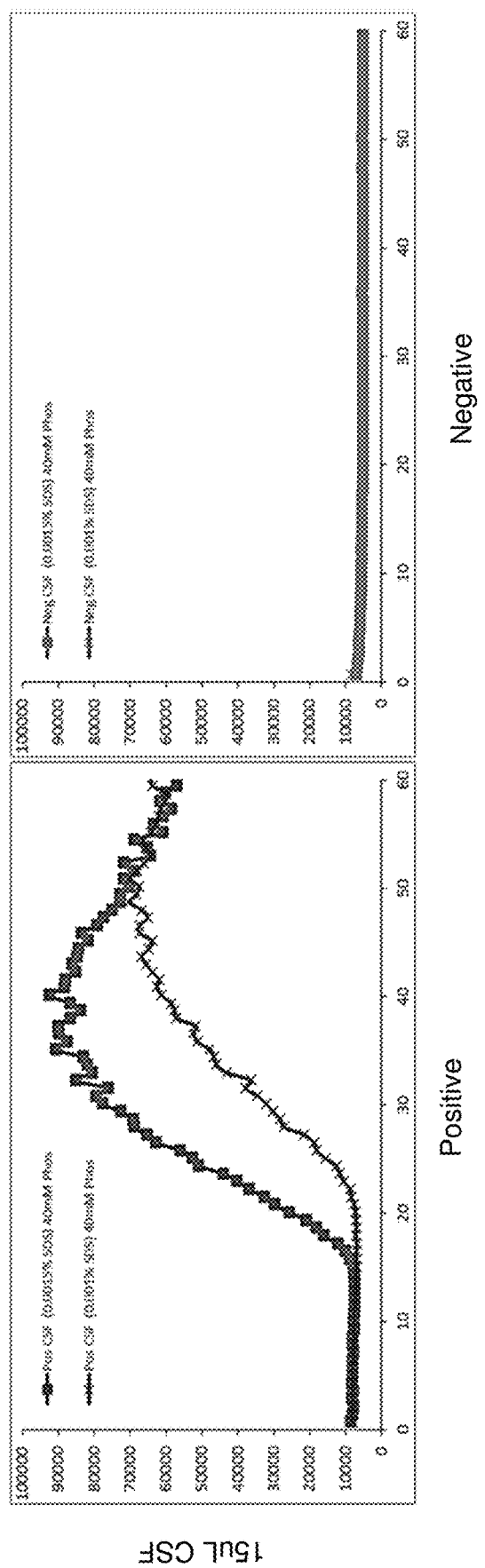

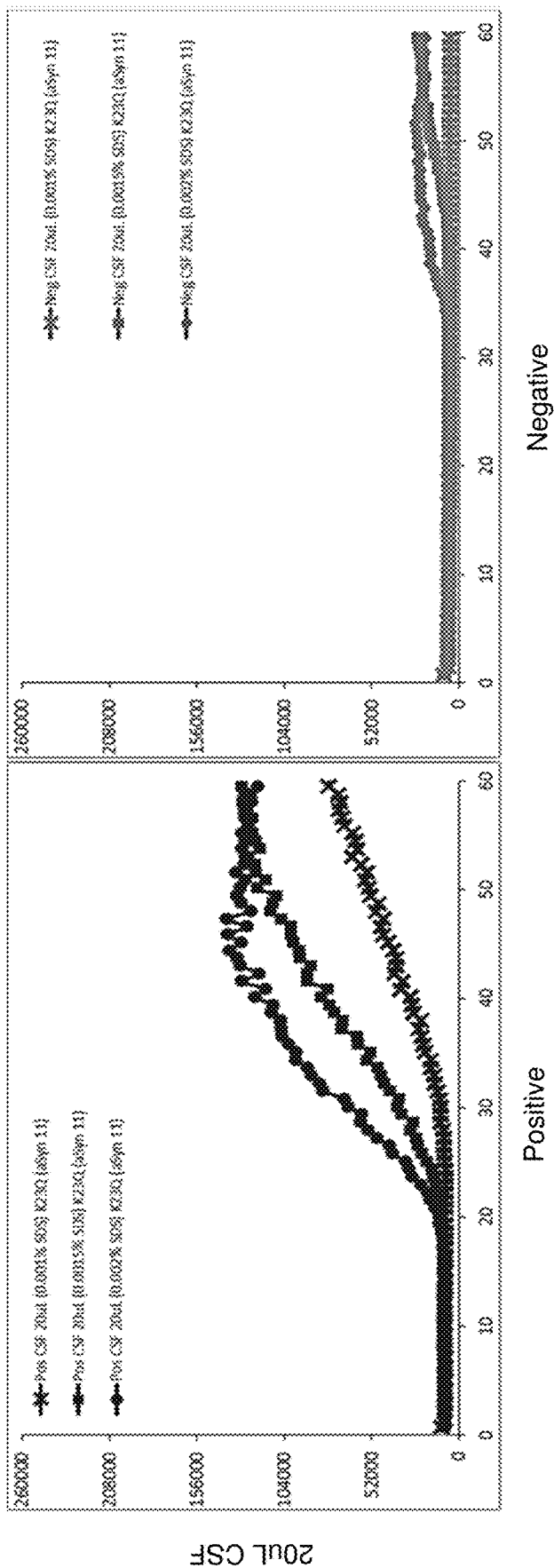

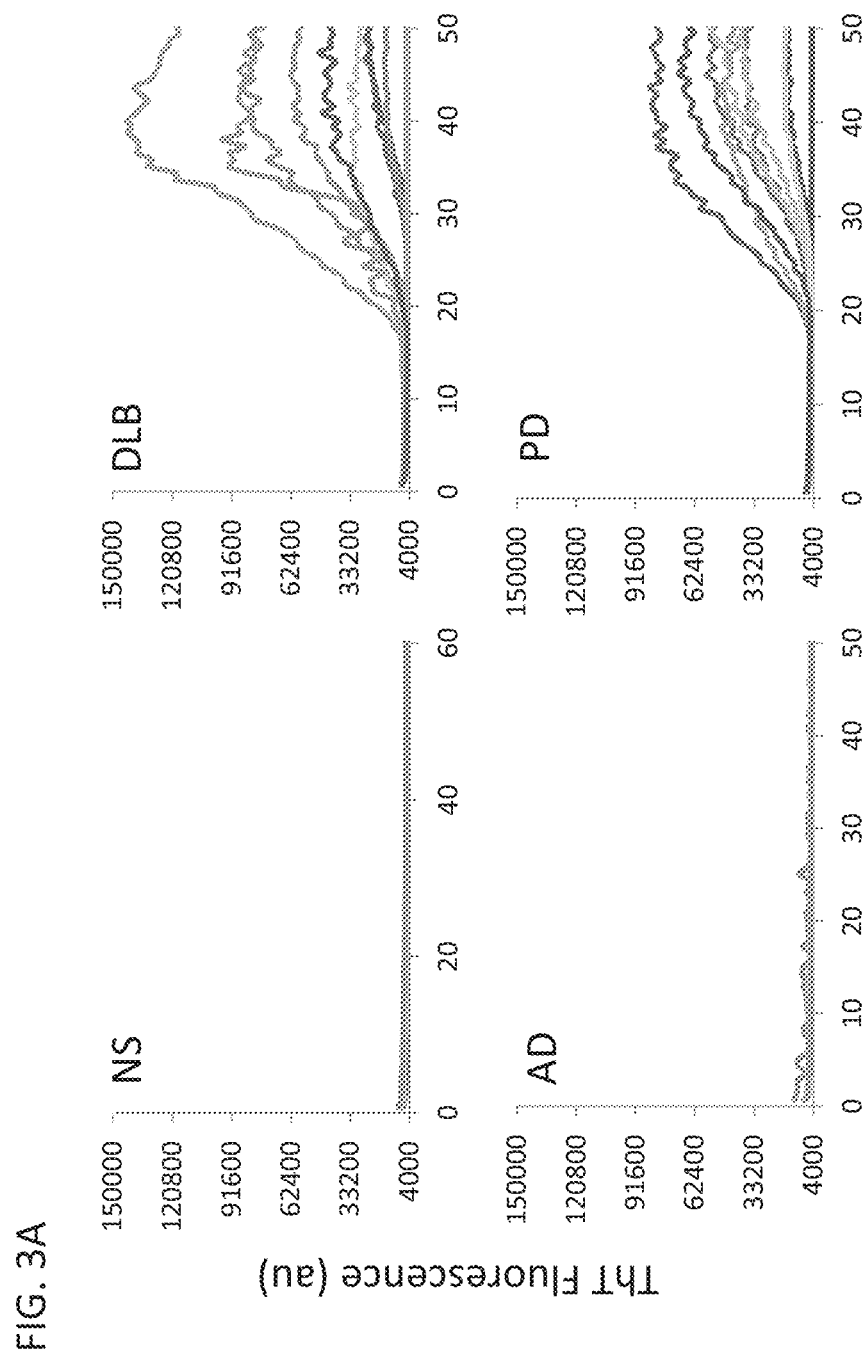

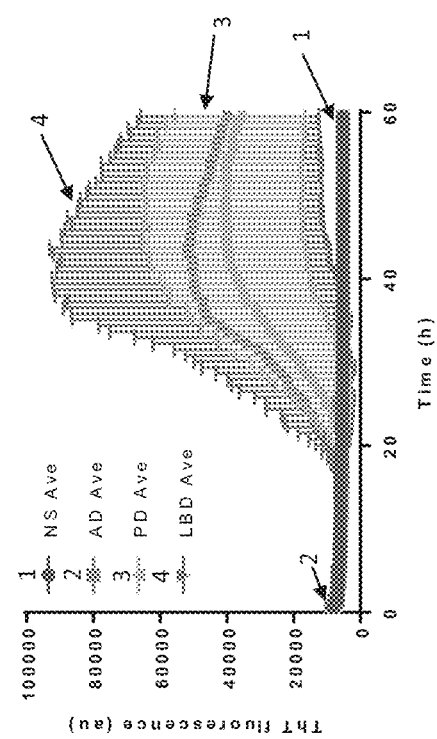
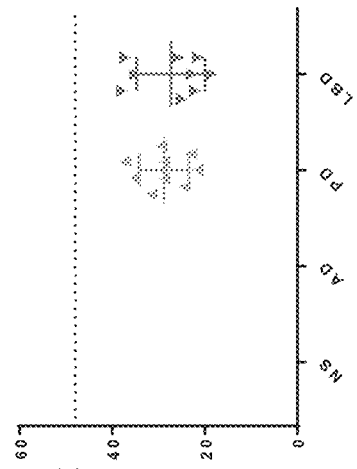
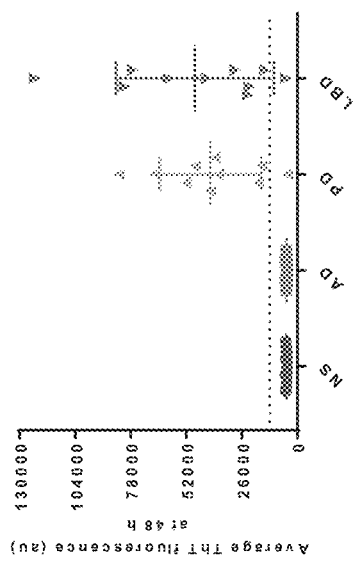
FIG. 3B
FIG. 3D
FIG. 3C

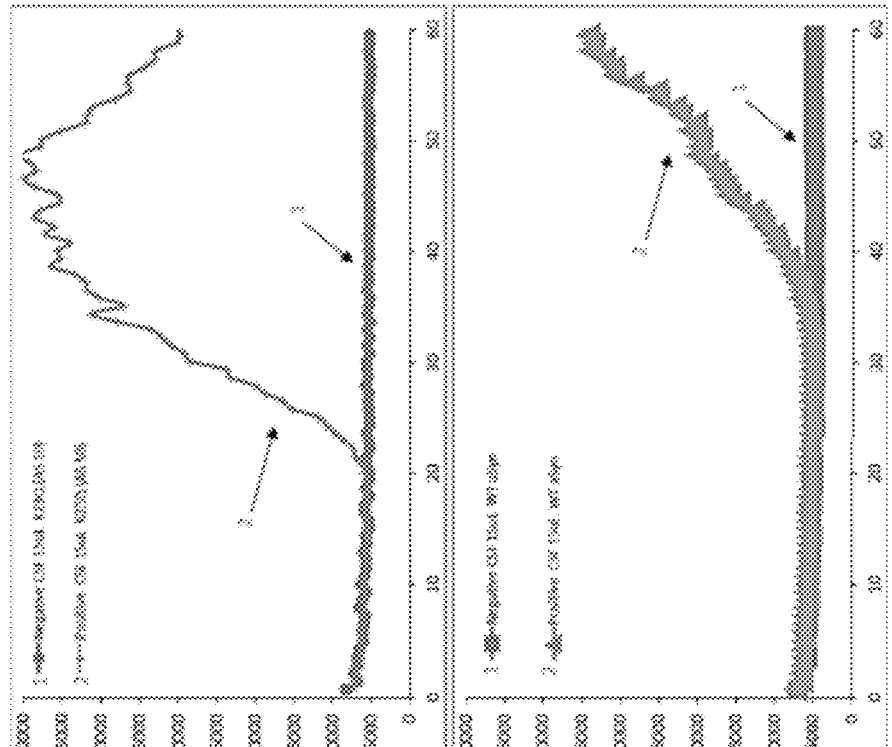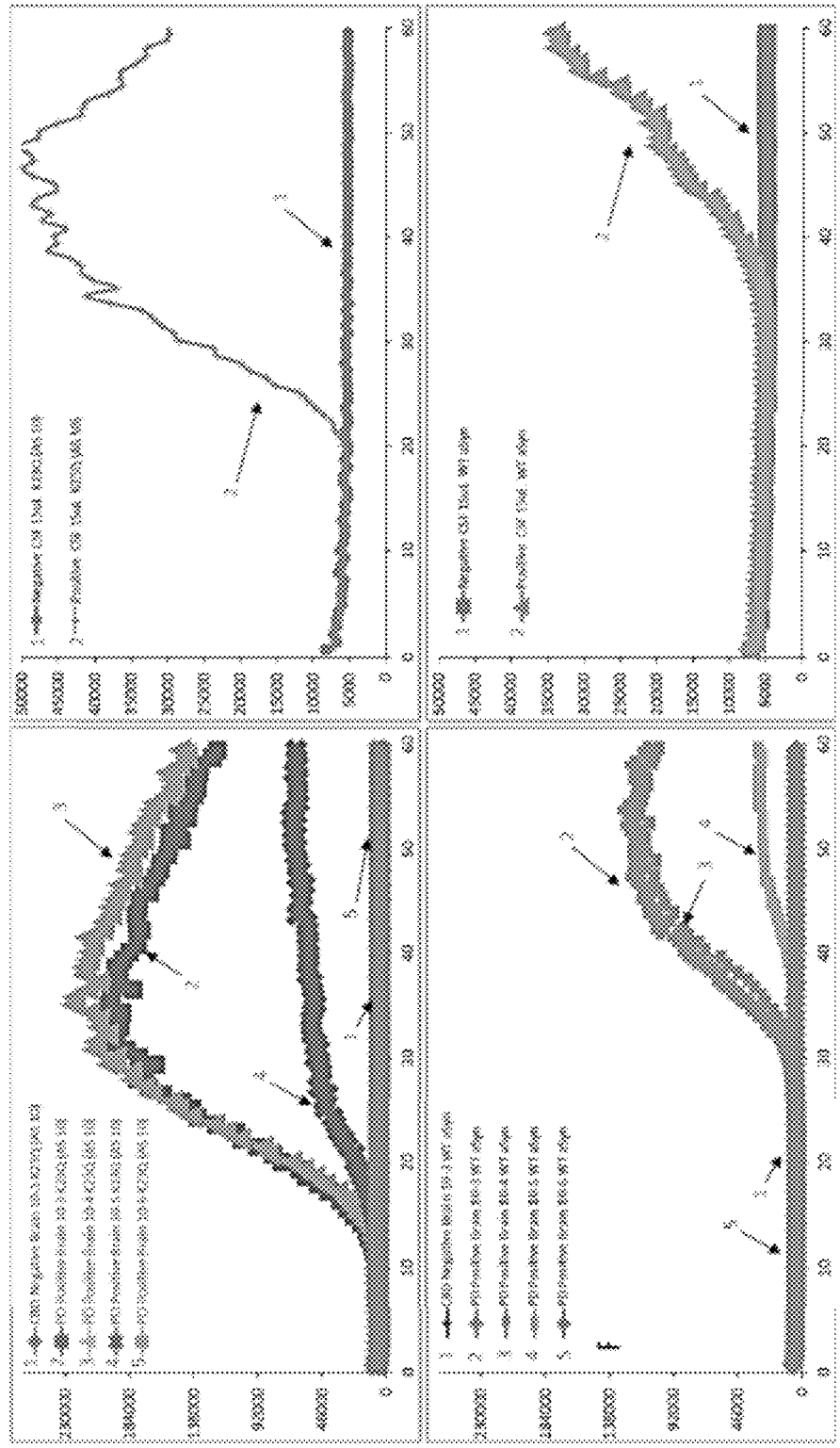

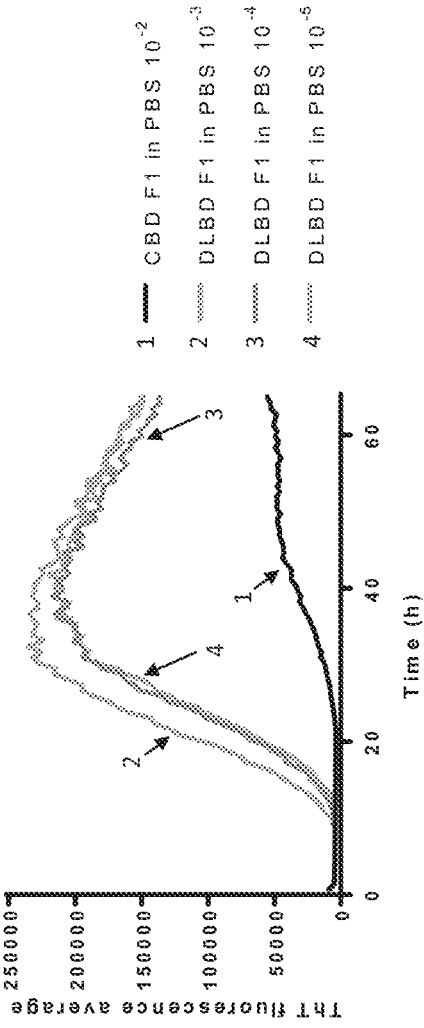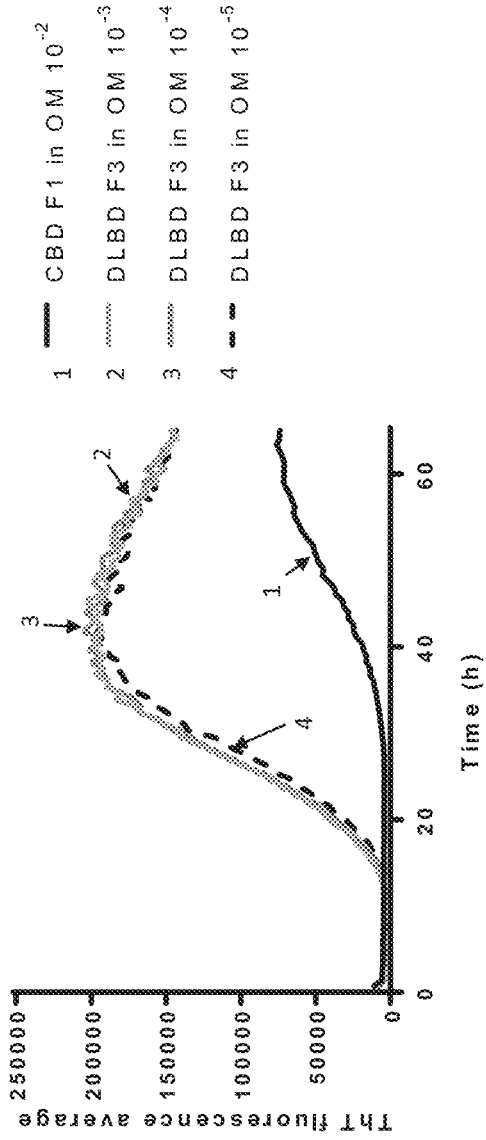
FIG. 7A
FIG. 7B

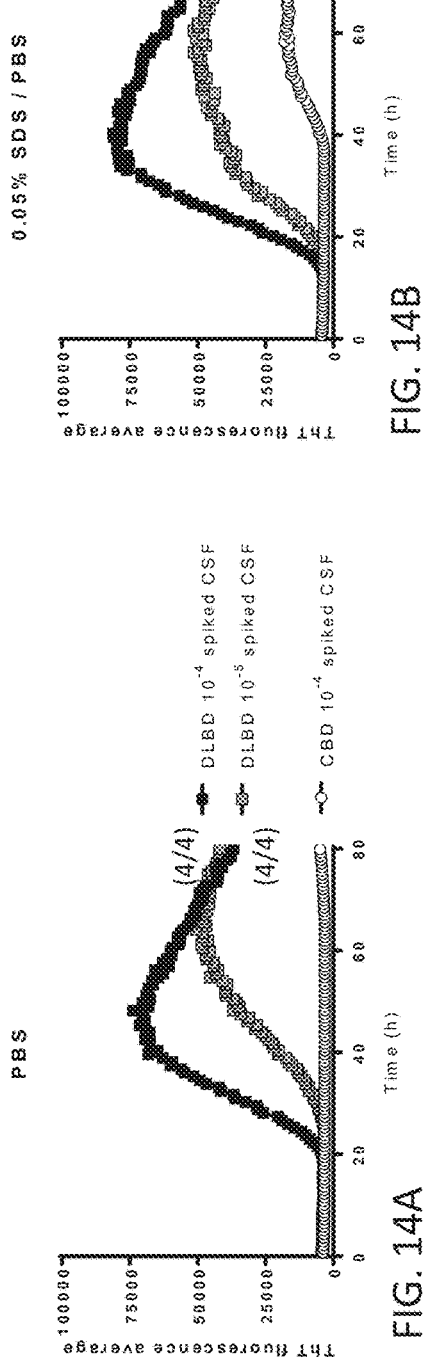
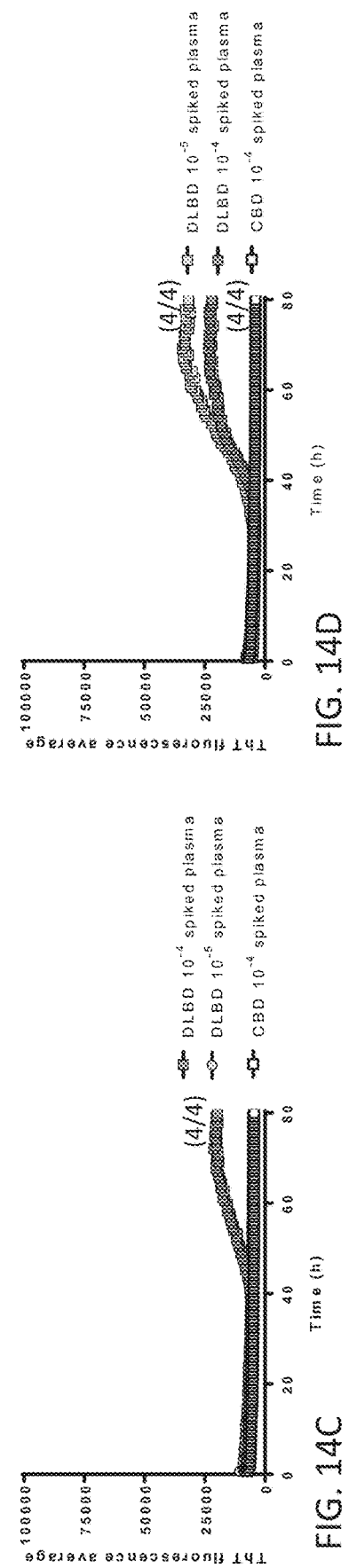

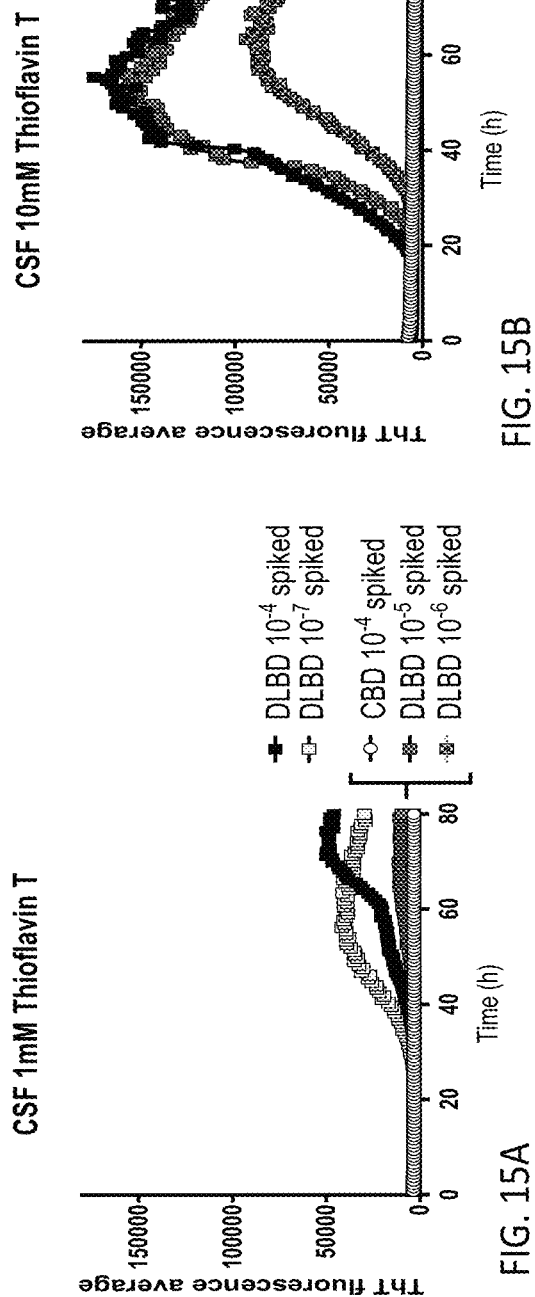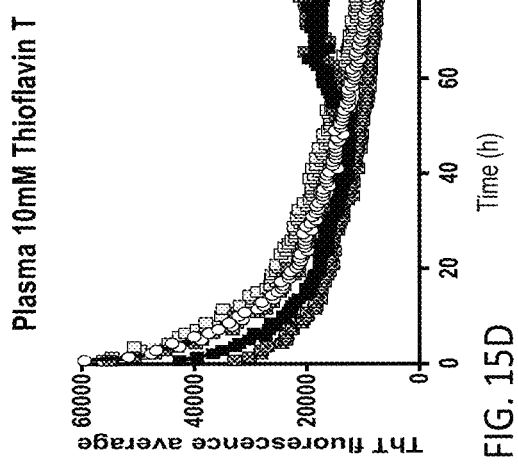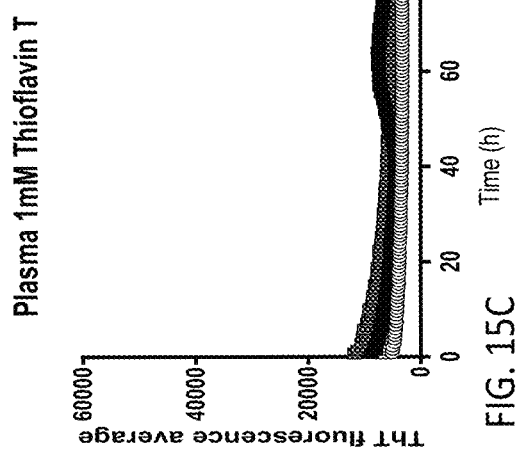
FIG. 15A
FIG. 15B
FIG. 15C
FIG. 15D

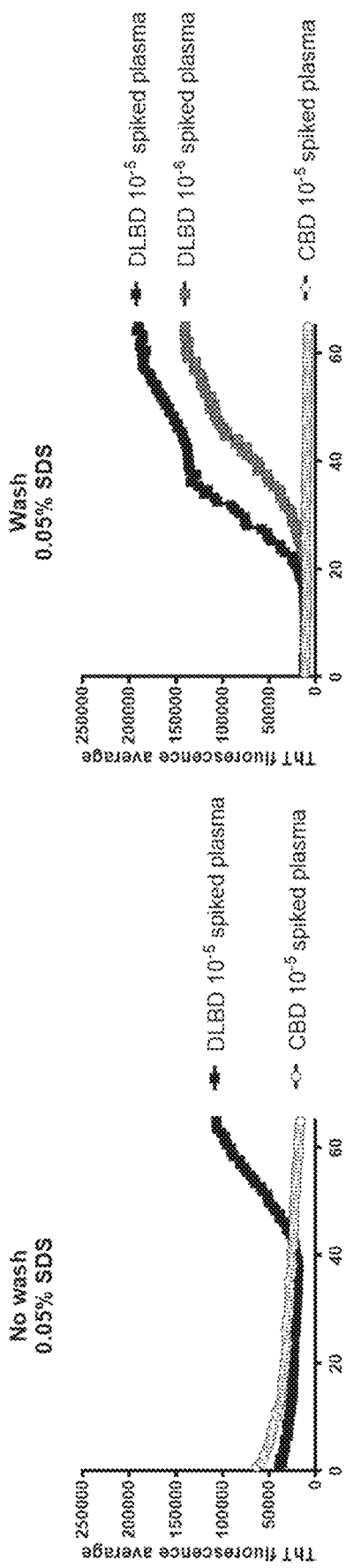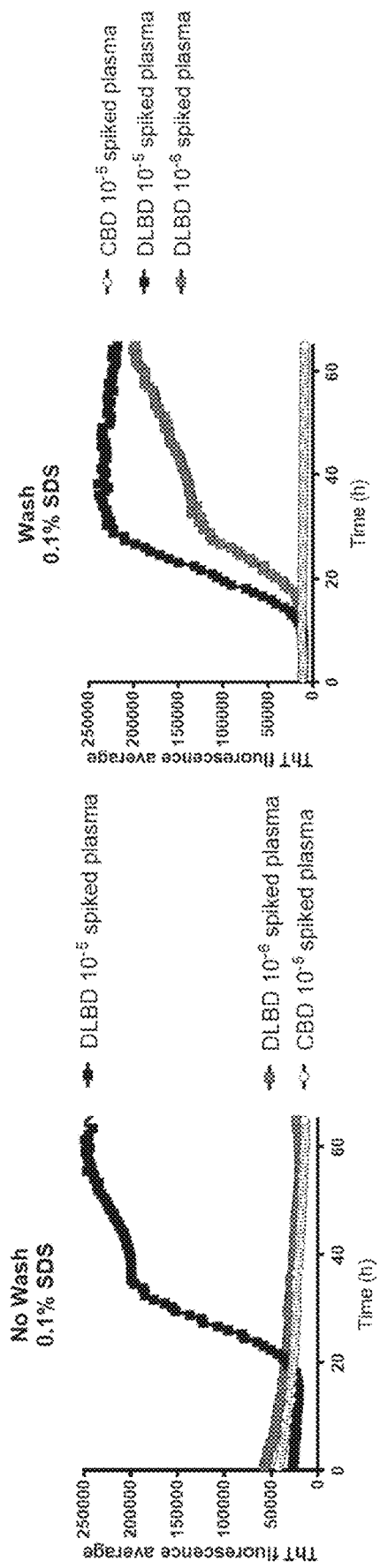
FIG. 16A  FIG. 16B  FIG. 16C  FIG. 16D

ASSAY FOR THE DETECTION OF ALPHA-SYNUCLEIN SEEDING ACTIVITY ASSOCIATED WITH SYNUCLEINOPATHIES

CROSS REFERENCE TO RELATED APPLICATIONS

This is a continuation of U.S. application Ser. No. 16/652,804, filed Apr. 1, 2020, issued as U.S. Pat. No. 11,313,867, on Apr. 26, 2022, which is the U.S. National Stage of International Application No. PCT/US2018/052968, filed Sep. 26, 2018, which was published in English under PCT Article 21(2), which claims the benefit of U.S. Provisional Application No. 62/567,079, filed Oct. 2, 2017. The above-listed applications are herein incorporated by reference in their entirety.

FIELD OF THE DISCLOSURE

This is related to the field of α-synucleinopathies, specifically to methods for rapid detection of misfolded α-Synuclein (αSyn) and diagnosis of α-synucleinopathies.

BACKGROUND

Many neurodegenerative diseases are caused, at least in part, by the accumulation of specific misfolded proteins. These deposits are typically identified upon post-mortem analysis of brain tissue, allowing diagnoses to be made based on specific neuropathological and molecular findings. Currently, prior to death, less certain diagnoses can be proffered based on combinations of clinical signs and biomarker levels. In addition, discrimination of causative agents in some diseases can be complicated by variations and overlaps in diagnostic indicators.

With Parkinson disease (PD), diagnoses are usually made late in the disease course with less accuracy by general practitioners and neurologists (50-75%) than movement disorder specialists (90%) (Hughes et al., 2002, Brain 125:861-70; Hughes et al., 1992, J. Neurol. Neurosurg. Psychiatry 55:181-184; Alder et al., 2014, Neurology 83:406-12). At first visit the diagnostic accuracy of a clinical diagnosis of PD varies between 26% and 88% (Alder et al., 2014, supra). Lewy Body dementias (including Dementia with Lewy bodies (DLB)), and multiple systems atrophy (MSA) are synucleinopathies that involve the pathological accumulation of α-Synuclein (αSyn). Attempts have been made to determine if cerebrospinal fluid (CSF) levels of total, phosphorylated or oligomeric αSyn can be used for diagnosis (reviewed in Parnetti et al., 2013, Nat Rev Neurol 9:131-40). To date, the results have been variable between studies, and the diagnostic utility of immunoassays for αSyn in CSF has not been demonstrated (Mollenhauer et al., 2017, Mov Disord doi:10.1002/mds.27090.; Sancesario and Bernardini, 2015, Crit Rev Clin Lab Sci 52:314-26) A need remains for highly sensitive assays for αSyn.

SUMMARY OF THE DISCLOSURE

While amplification reactions for detecting αSyn seeding activity have been developed, these methods are slow, and must be performed over 5 to 13 days. It is disclosed herein that using specific mutated recombinant alpha synuclein (rαSyn) substrates, a more rapid αSyn RT-QuIC assay was developed. Misfolded αSyn present in a sample was quickly detected, with excellent sensitivity and specificity. These methods disclosed herein can be used to detect misfolded αSyn in a biological sample, or fraction thereof, and can be used to diagnose synucleinopathies.

In some embodiments, methods are disclosed for determining whether a subject has a synucleinopathy. These methods include performing an αSyn seeding assay on a biological sample from the subject, or a fraction thereof, wherein the seeding assay includes: i) contacting the biological sample, or fraction thereof, with a soluble mutated rαSyn to form a reaction mixture, wherein the soluble mutated rαSyn comprises an amino acid sequence a) comprising one to eight point mutations in SEQ ID NO: 1, wherein the point mutations are at residues K23, D2, K21, K45, T59, G67, V77, and/or A78 and/or b) a deletion of up to ten amino acids in amino acids 2-11 of SEQ ID NO: 1; ii) incubating the reaction mixture to permit coaggregation of misfolded αSyn aggregates present in the biological sample, or fraction thereof, with the mutated rαSyn; iii) maintaining incubation conditions that promote coaggregation of the mutated rαSyn with the misfolded αSyn aggregates to result in a conversion of the soluble mutated rαSyn to mutated rαSyn aggregates while inhibiting spontaneous aggregation of soluble mutant rαSyn; and iv) agitating mutated rαSyn aggregates formed during step iii), wherein the conditions comprise shaking the reaction mixture in a shaking cycle, wherein each shaking cycle comprises a period of rest and a period of shaking. Misfolded mutated rαSyn aggregates are detected in the reaction mixture, wherein detection of misfolded mutated rαSyn aggregates in the reaction mixture indicates that the subject has the synucleinopathy.

Methods are also disclosed for detecting misfolded αSyn in a biological sample or a fraction thereof. These methods include mixing the biological sample or fraction thereof with a purified soluble mutated rαSyn to make a reaction mix, wherein the soluble mutated rαSyn comprises an amino acid sequence a) comprising one to eight point mutations in SEQ ID NO: 1, wherein the point mutations are at residues K23, D2, K21, K45, T59, G67, V77, and/or A78 and/or b) with a deletion of up to ten amino acids in amino acids 2-11 of SEQ ID NO: 1. An amplification reaction is performed that includes: (i) incubating the reaction mix to permit coaggregation of the soluble mutated rαSyn with misfolded αSyn that may be present in the reaction mix, and maintaining incubation conditions that promote coaggregation of the soluble mutated rαSyn with the misfolded αSyn and result in a conversion of the soluble mutated rαSyn to misfolded rαSyn aggregates initiated by the presence of misfolded αSyn in the sample, while inhibiting development of spontaneously arising rαSyn aggregates; and (ii) agitating aggregates formed during step (i), in shaking cycles, wherein each shaking cycle of the shaking cycles comprises a period of rest and a period of shaking, wherein agitating is performed in the absence of sonication. Misfolded rαSyn aggregates are then detected in the reaction mix, and detection of misfolded rαSyn in the reaction mix indicates that misfolded αSyn was present in the biological sample.

Protein amino acid residues are referred to throughout by their amino acid identity and position number in the protein. For example, with regard to SEQ ID NO: 1, "D2" refers to the aspartic acid at position 2 of the protein described in SEQ ID NO: 1; "K21" refers to the lysine at position 21 of the protein described in SEQ ID NO:1; "K23" refers to the lysine at position 23 of the protein described in SEQ ID NO:1 and so forth. Mutations to protein residues are referred to throughout by the amino acid originally present in the protein, the position number of the amino acid in the protein, followed by the new amino acid replacing the original amino acid in the mutated form of the protein. For example, "K23Q" indicates that the lysine at position 23 has been changed to a glutamine. "K23X" indicates that the lysine at position 23 has been changed to any other amino acid except lysine.

The foregoing and other features and advantages of the invention will become more apparent from the following detailed description of several embodiments which proceeds with reference to the accompanying figures.

BRIEF DESCRIPTION OF THE FIGURES

FIGS. 2A-2F. Sodium Dodecyl Sulfate (SDS) and CSF titration in αSyn RT-QuIC. Quadruplicate K23Q substrate αSyn RT-QuIC reactions were seeded with 10, 15 or 20 μL of CSF (FIGS. 2A-2B, 2C-2D and 2E-2F, respectively) in reactions containing 0.001, 0.0015 or 0.002% SDS. The CSF samples were either from a synucleinopathy (PD) patient or a non-synucleinopathy (CBD) control patient. Each well contained 6 glass beads of 1 mm diameter. Each sample trace represents the average thioflavin T (ThT) fluorescence of four wells. The results show that when using 10 μL of CSF per reaction in combination with 0.002% SDS some spontaneous conversion of the substrate in non-synucleinopathy (CBD) CSF seeded reactions can occur. This is not observed when the same volume of CSF was used in combination with 0.0015% SDS (FIG. 2B). In FIG. 2C, where reactions were seeded with 15 μl of CSF, rapid detection of αSyn seeding activity was observed in synucleinopathy positive CSF seeded reactions and no spontaneous conversion of the substrate (FIG. 2D) was observed in non-synucleinopathy CSF seeded reactions. In FIG. 2E, where reactions were seeded with 20 μl of CSF, samples gave weaker and slower fluorescence signals (average of quadruplicate wells) with spontaneous conversion of the substrate in non-synucleinopathy CSF seeded reactions with 0.002 and 0.0015% SDS in the reaction mix.

FIGS. 3A-3D. Blinded testing of CSF samples by αSyn RT-QuIC. Cerebrospinal fluid (CSF) samples from non-synucleinopathy (NS), Alzheimer's (AD, which only infrequently involves abnormal αSyn deposition), dementia with Lewy Bodies (DLB) or Parkinson Disease (PD) patients, were tested blinded using αSyn RT-QuIC with K23Q rαSyn substrate. Quadruplicate reactions were seeded with 15p L of CSF in the presence of 0.0015% SDS. Each sample trace represents the average ThT fluorescence from four replicate wells. Samples were incubated at 42° C. with cycles of one-minute double orbital shaking at 400 rpm and one-minute resting, for 50 hours. Each well contained 6 glass beads. FIG. 3A shows the kinetics of seeding activity from individual patients. FIG. 3B shows the average (+/−SD) fluorescence amplification kinetics for the AD, DLB and PD patients over time. FIG. 3C shows the overall average maximum fluorescence per sample type (+/−SD) at 48 hours when a final evaluation of the results is made. The dashed line shows the fluorescence threshold for a positive determination according to our criteria. FIG. 3D shows the time required to reach the positivity threshold in synucleinopathy (PD or LBD), non-synucleinopathy (NS) or Alzheimer (AD) samples. The dashed line indicated the 48-hour cutoff time. Most of the PD (%10) and DLB (%10) CSFs gave positive responses within 15-35 h (FIG. 3A). The average reaction time required to exceed the positivity threshold was similar for the PD and DLB specimens (FIG. 3D). Again, most of the control cases without any indication of synucleinopathy were negative in all 4 replicate αSyn RT-QuIC reactions. Overall, the results from this blinded panel indicated diagnostic sensitivities, i.e. the percentage of cases giving positive RT-QuIC responses, of 90% (95% CI, 54-99) for PD and 90% (95% CI, 54-99) for DLB. The negative results from the remainder of the apparent non-synucleinopathy controls indicated a specificity of 100% (95% CI=80-100).

FIGS. 4A-4D. Comparison of the performance of K23Q (FIGS. 4A and 4B) and wild type (FIGS. 4C and 4D) αSyn recombinant protein in the αSyn RT-QuIC. Reactions were seeded in quadruplicate with $10^{-3}$ to $10^{-6}$ dilutions of a synucleinopathy-negative (CBD) or -positive (PD) brain homogenate (FIGS. 4A & 4C); or 15 μL of CSF from non-synucleinopathy patients or a PD patient (FIGS. 4B & 4D). Each sample trace represents the average ThT fluorescence of quadruplicate wells. Samples were incubated at 42'C with one-minute shaking at 400 rpm and one-minute resting, for 50 hours. Each well contained 6 glass beads and CSF seeded reactions included 0.0015% SDS in the reaction mix. In no case were positive RT-QuIC responses observed from the CBD samples. The PD brain dilutions gave positive responses down to $10^{-5}$ using either the K23Q or wildtype rαSyn substrates, but the responses were faster and stronger using the K23Q substrate. The PD CSF seed also gave faster responses using the K23Q substrate.

FIGS. 7A-7B. Evaluation of olfactory mucosa (OM) tissue matrix effect on RT-QuIC detection of αSyn seeding activity. Brain tissue dilutions were spiked into non-prion disease human OM samples to give final concentrations of $10^{-2}$ corticobasal degeneration (CBD) or $10^{-3}$-$10^{-5}$ diffuse Lewy body disease (DLBD) brain tissue. Quadruplicate reactions were seeded with the indicated dilutions of OMs with each trace in the graph representing the average fluorescence readings for each sample dilution. FIG. 7A shows brain homogenate dilutions spiked into phosphate buffered saline (PBS) and FIG. 7B shows the same dilutions spiked into OM background. At $10^{-2}$ brain tissue dilutions spiked into PBS spontaneous conversion of the substrate was observed in the CBD reactions after ~25-30 hours of incubation. When $10^{-2}$ brain tissue dilutions were spiked into OM tissue background spontaneous conversion of the substrate occurred later around 40 hours. Overall, no major difference was observed in reaction kinetics when samples were diluted in an OM tissue background indicating that there is no significant tissue matrix effect on the αSyn RT-QuIC assay.

FIG. 13A. Human CSF from one LBD and one CBD patient were serially diluted into non-disease normal CSF. The equivalent volumes of endogenous CSF tested per well are shown. Thioflavin T fluorescence traces are the average of 4 replicate wells. The lowest detectable volume (3 positive reactions out of 4 replicate wells) of LBD CSF was of 0.046 μL. FIG. 13B. The same equivalents of LBD and CBD CSF samples indicated in the upper panel were further diluted into 500 μL of non-disease human CSF and captured using 2 μL (98 μg) per sample of IO particles in a 2-hour incubation at room temperature. Following capture, the particles were washed once with PBS and resuspended in 8 μL of PBS. Prior to seeding four replicate wells the particles were sonicated at 63% power until resuspended. The traces are the average of four replicate wells. These results showed that, by using the capture, seeding activity was recovered after dilution into a 2,700-fold greater volume of normal CSF. The IO capture increased the sensitivity of the assay by permitting collection and detection of αSyn seeds from much larger volumes of CSF than can be added directly to RT-QuIC reactions. This capture approach provides an increase in the assay's dynamic range for quantitation of seeding activity.

FIGS. 14A-14D. Comparison of IO particle treatment following αSyn seeding activity capture out of human CSF or plasma: 0.05% sodium dodecyl sulfate (SDS) in PBS vs. PBS alone. FIGS. 14A and 14B. Human CSF (500 μL) was spiked with brain homogenates to give final concentrations of $10^{-4}$ CBD (negative control) brain tissue or $10^{-4}$ and $10^{-5}$ DLBD brain tissue. αSyn seeding activity was captured using 98 μg of IO particles with an incubation of 2 hours at room temperature. At the end of the capture the particles were resuspended in either 0.05% sodium dodecyl sulfate (SDS) in PBS or in PBS alone. Next the particles were briefly cuphorn sonicated at 63% power and split into 4 wells. The traces are the average of four replicate wells. The results showed that detection of αSyn seeding activity in the DLBD-spiked CSF samples was similar with respect to reaction kinetics for the two brain dilutions. However, when the particles were resuspended in the 0.05% in PBS more rapid spontaneous conversion of the substrate was observed in the reactions seeded with the negative control CBD sample. These results indicated that in the case of CSF, following capture, the particles are better resuspended in PBS alone. FIGS. 14C-14D. Human plasma (500 µL) was spiked with brain homogenates to give final concentrations of $10^{-4}$ CBD (negative control) brain tissue or $10^{-4}$ and $10^{-5}$ DLBD brain tissue. αSyn seeding activity was captured using 98 µg of IO particles with an incubation of 2 hours at room temperature. At the end of the capture the particles were treated using the same methods. When the particles were resuspended in PBS alone seeding activity could only be detected in the $10^{-4}$ DLBD-spiked plasma and not in the $10^{-5}$-spiked plasma. In contrast, when the particles were resuspended in 0.05% SDS in PBS, αSyn seeding activity was detected in both the $10^{-4}$ and $10^{-5}$ spiked plasma. These results suggest that when using IO capture in plasma, the particles are better resuspended in 0.05% SDS in PBS rather than PBS alone to achieve maximal sensitivity. However, both 0.05% SDS in PBS and PBS alone (or another buffer) can be used, albeit with different sensitivities.

FIGS. 15A-15D. Assessment of Thioflavin T concentration (1 mM vs. 10 mM) on αSyn RT-QuIC detection of IO captured seeding activity. FIGS. 15A and 15B. Human CSF (500 µL) was spiked to give $10^{-4}$ final CBD brain tissue dilution or $10^{-4}$ to $10^{-7}$ DLBD brain tissue dilutions. αSyn seeding activity was captured using 98 µg of IO particles with an incubation of 2 hours at room temperature. At the end of the capture the particles were resuspended in PBS and briefly sonicated at 63% power prior to seeding four wells. The traces are the average of four replicate wells. The 10 mM ThT solution allowed for stronger fluorescence signals in the presence of the IO when testing CSF samples. FIG. 15C-15D. Human plasma (500 µL) was spiked to give $10^{-4}$ final CBD brain tissue dilution or $10^{-4}$ to $10^{-7}$ DLBD brain tissue dilutions. αSyn seeding activity was captured using 98 µg of IO particles with an incubation of 2 hours at room temperature. At the end of the capture the particles were resuspended in 0.05% SDS in PBS and briefly sonicated at 63% power prior to seeding four wells. The traces are the average of four replicate wells. The use of 10 mM ThT solution allowed for a slightly stronger fluorescence signal with IO capture from plasma samples, although the improvement was not as significant as the one observed for the study using CSF. Thus, increased ThT concentration can, but does not necessarily, provide increased sensitivity.

FIGS. 16A-16D. Comparison of 0.05 vs 0.1% SDS/PBS and no wash vs. one wash in IO capture of αSyn seeding activity spiked into human plasma. Human plasma (500 µL) was spiked to give $10^{-5}$ final CBD brain tissue dilution or $10^{-5}$ and $10^{-6}$ DLBD brain tissue dilution. αSyn seeding activity was captured using 98 µg of IO particles with an incubation of 2 hours at room temperature. At the end of the capture the particles were resuspended in either 0.05% or 0.1% SDS/PBS and briefly sonicated at 63% power prior to seeding 4 wells. The traces are the average of four replicate wells. The data (FIGS. 16A and 16C) showed a much stronger and faster detection of seeding activity at the $10^{-5}$ brain tissue dilution when the particles are resuspended in 0.1% SDS/PBS, but no detection of the $10^{-6}$ dilution was observed in both cases. A PBS wash (FIGS. 16B and 16D) was introduced after the capture and further compared the αSyn amplification kinetics following treatment with either 0.05% or 0.1% SDS/PBS. The PBS wash allowed for detection of the $10^{-6}$ brain tissue dilution spike with both SDS concentrations, with the 0.1% SDS given slightly faster and stronger fluorescence responses. The combination of the 0.1% SDS/PBS treatment and the use of one PBS wash improved the sensitivity and speed of detection of the αSyn RT-QuIC.

FIG. 20A. Non-disease human normal CSF (500 µL) was spiked with serial dilutions of DLBD or CBD brain homogenate. Final brain tissue dilutions in CSF are indicated. Spiked CSF was subjected to three consecutive captures with the same spiked material being incubated with fresh 2 μL of IO particles for 2 hours at room temperature. After each capture the particles were washed once with PBS, resuspended in 8 μL of PBS and stored at 4° C. until ready to be tested. Prior to seeding, the wells the particles were briefly sonicated at 63% power. Traces are the average Thioflavin T fluorescence for four replicate wells. These results show that, even after three captures of the same material, spiked seeding activity was detected at similar levels on the IO particle. This indicates that the capture efficiency of the IO beads was ≤33%. As αSyn seeds were detected throughout, that the sensitivity of the RT-QuIC amplification assay was confirmed to be sufficient to allow discrimination of positive vs. negative samples. FIG. 20B. Endogenous CSF samples from one DLBD and one CBD patient were subjected to three consecutive captures as described in FIG. 20A. The DLBD endogenous CSF sample (sample #12835) was tested undiluted, diluted 1:10 or 1:100 in non-disease CSF. The efficiency of capture was less than 100% and the αSyn RT-QuIC detected seeding activity was detected even after a third capture. Furthermore, the third capture showed slightly faster detection of seeding activity than the $1^{st}$ and $2^{nd}$ capture. This result suggests that a potential amplification inhibitor may be removed following capture.

FIG. 21A) column, an Ion Exchange column (IEX; FIG. 21B), or an IMAC followed by and IEX column (FIG. 21C). Seeds for the reactions were generated by shaking 1 mg/ml recombinant alpha-synuclein at 1,000 rpm for 5 days. The seed was serially diluted in phosphate buffer to a final concentration of 10 μg in the reaction. Phosphate buffer was used in the unseeded reactions as a control. The results showed that using both columns improved the stability of the substrate in the absence of seed and generated a protein that allowed faster amplification reactions compared to the IMAC and IEX columns individually.

SEQUENCE LISTING

Figure 1:
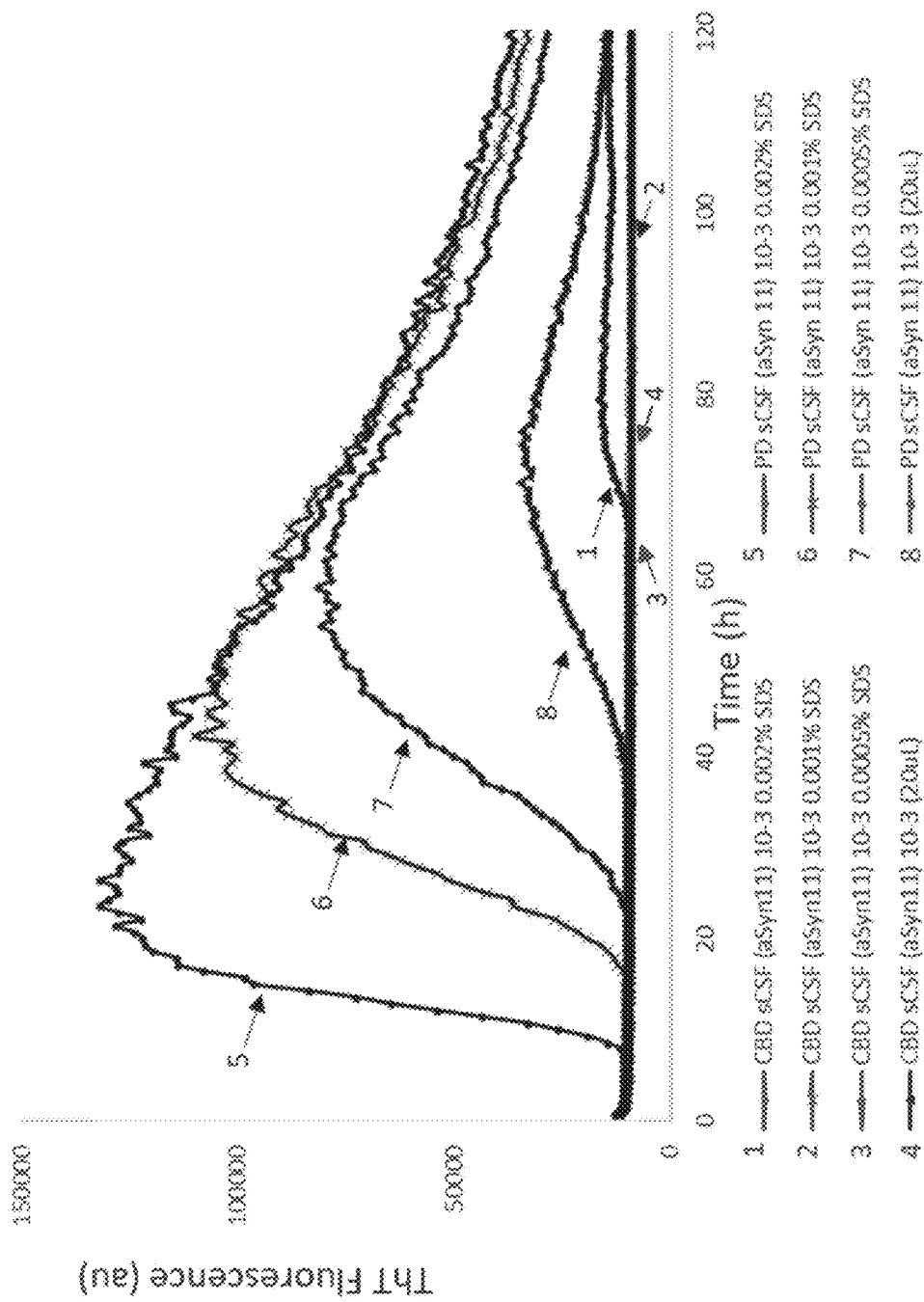
FIG. 1. Sodium Dodecyl Sulfate (SDS) titration in CSF-seeded αSyn RT-QuIC. Quadruplicate reactions were seeded with 20 μL per well of CSF from a patient with Cortical Basal Degeneration (CBD) (a tauopathy, sample wherein αSyn accumulation was not present) or one diagnosed with Parkinson Disease (PD). Each sample trace represents the average thioflavin T (ThT) signal of four wells. Each reaction mix contained either 0.002% (5), 0.001% (6), 0.0005% (7) or 0% (8) final SDS concentration. αSyn seeding activity was detected using the K23Q substrate while incubating at 42'C with cycles of one-minute double orbital shaking at 400 rpm and one-minute resting, for 120 hours. Each well contained 6 glass beads that were 1 mm in diameter. Matching negative controls are shown with matching symbols numbered 1-4. The results indicated that 0.0005%, 0.001% and 0.002% SDS accelerated PD CSF-seeded aggregation of K23Q rαSyn as detected by increased ThT fluorescence, relative to PD CSF-seeded reactions with no SDS or similarly treated reactions receiving the negative control, non-synucleinopathy CBD CSF.

The amino acid sequences listed below are shown using single letter code for amino acids, as defined in 37 C.F.R. 1.822. The Sequence Listing is submitted as an ASCII text file, Mar. 23, 2022, 34.3 KB, which is incorporated by reference herein. The following sequences are disclosed (X is any amino acid):

```
SNCA
                                                          (SEQ ID NO: 1)
MDVFMKGLSKAKEGVVAAAEKTKQGVAEAAGKTKEGVLYVGSKTKEGVVHGVATVAEKTKE

QVTNVGGAVVTGVTAVAQKTVEGAGSIAAATGFVKKDQLGKNEEGAPQEGILEDMPVDPDNE

AYEMPSEEGYQDYEPEA

6XHis SNCA
                                                          (SEQ ID NO: 2)
MGSSHHHHHHSSGLVPRGSHMDVFMKGLSKAKEGVVAAAEKTKQGVAEAAGKTKEGVLYVG

SKTKEGVVHGVATVAEKTKEQVTNVGGAVVTGVTAVAQKTVEGAGSIAAATGFVKKDQLGKN

EEGAPQEGILEDMPVDPDNEAYEMPSEEGYQDYEPEA

SNCA K23E
                                                          (SEQ ID NO: 3)
MDVFMKGLSKAKEGVVAAAEKTEQGVAEAAGKTKEGVLYVGSKTKEGVVHGVATVAEKTKE

QVTNVGGAVVTGVTAVAQKTVEGAGSIAAATGFVKKDQLGKNEEGAPQEGILEDMPVDPDNE

AYEMPSEEGYQDYEPEA

6XHis SNCA K23E
                                                          (SEQ ID NO: 4)
MGSSHHHHHHSSGLVPRGSHMDVFMKGLSKAKEGVVAAAEKTEQGVAEAAGKTKEGVLYVG

SKTKEGVVHGVATVAEKTKEQVTNVGGAVVTGVTAVAQKTVEGAGSIAAATGFVKKDQLGKN

EEGAPQEGILEDMPVDPDNEAYEMPSEEGYQDYEPEA

SNCA K23Q
                                                          (SEQ ID NO: 5)
MDVFMKGLSKAKEGVVAAAEKTQQGVAEAAGKTKEGVLYVGSKTKEGVVHGVATVAEKTKE

QVTNVGGAVVTGVTAVAQKTVEGAGSIAAATGFVKKDQLGKNEEGAPQEGILEDMPVDPDNE
```

AYEMPSEEGYQDYEPEA

6XHis SNCA K23Q
(SEQ ID NO: 6)
<u>MGSSHHHHHHSSGLVPRGSH</u>MDVFMKGLSKAKEGVVAAAEKT<u>Q</u>QGVAEAAGKTKEGVLYVG
SKTKEGVVHGVATVAEKTKEQVTNVGGAVVTGVTAVAQKTVEGAGSIAAATGFVKKDQLGKN
EEGAPQEGILEDMPVDPDNEAYEMPSEEGYQDYEPEA

SNCA del12
(SEQ ID NO: 7)
MKEGVVAAAEKTKQGVAEAAGKTKEGVLYVGSKTKEGVVHGVATVAEKTKEQVTNVGGAVV
TGVTAVAQKTVEGAGSIAAATGFVKKDQLGKNEEGAPQEGILEDMPVDPDNEAYEMPSEEGYQ
DYEPEA 6XHis SNCA del12
(SEQ ID NO: 8)
<u>MGSSHHHHHHSSGLVPRGSH</u>MKEGVVAAAEKTKQGVAEAAGKTKEGVLYVGSKTKEGVVHG
VATVAEKTKEQVTNVGGAVVTGVTAVAQKTVEGAGSIAAATGFVKKDQLGKNEEGAPQEGILE
DMPVDPDNEAYEMPSEEGYQDYEPEA SNCA D2X
(SEQ ID NO: 9)
MXVFMKGLSKAKEGVVAAAEKTKQGVAEAAGKTKEGVLYVGSKTKEGVVHGVATVAEKTKE
QVTNVGGAVVTGVTAVAQKTVEGAGSIAAATGFVKKDQLGKNEEGAPQEGILEDMPVDPDNE
AYEMPSEEGYQDYEPEA 6XHis SNCA D2X
(SEQ ID NO: 10)
<u>MGSSHHHHHHSSGLVPRGSH</u>MXVFMKGLSKAKEGVVAAAEKTKQGVAEAAGKTKEGVLYVG
SKTKEGVVHGVATVAEKTKEQVTNVGGAVVTGVTAVAQKTVEGAGSIAAATGFVKKDQLGKN
EEGAPQEGILEDMPVDPDNEAYEMPSEEGYQDYEPEA SNCA K21X
(SEQ ID NO: 11)
MDVFMKGLSKAKEGVVAAAEXTKQGVAEAAGKTKEGVLYVGSKTKEGVVHGVATVAEKTKE
QVTNVGGAVVTGVTAVAQKTVEGAGSIAAATGFVKKDQLGKNEEGAPQEGILEDMPVDPDNE
AYEMPSEEGYQDYEPEA 6XHis SNCA K21X
(SEQ ID NO: 12)
<u>MGSSHHHHHHSSGLVPRGSH</u>MDVFMKGLSKAKEGVVAAAEXTKQGVAEAAGKTKEGVLYVG
SKTKEGVVHGVATVAEKTKEQVTNVGGAVVTGVTAVAQKTVEGAGSIAAATGFVKKDQLGKN
EEGAPQEGILEDMPVDPDNEAYEMPSEEGYQDYEPEA SNCA K23X
(SEQ ID NO: 13)
MDVFMKGLSKAKEGVVAAAEKTXQGVAEAAGKTKEGVLYVGSKTKEGVVHGVATVAEKTKE
QVTNVGGAVVTGVTAVAQKTVEGAGSIAAATGFVKKDQLGKNEEGAPQEGILEDMPVDPDNE
AYEMPSEEGYQDYEPEA 6XHis SNCA K23X
(SEQ ID NO: 14)
<u>MGSSHHHHHHSSGLVPRGSH</u>MDVFMKGLSKAKEGVVAAAEKTXQGVAEAAGKTKEGVLYVG
SKTKEGVVHGVATVAEKTKEQVTNVGGAVVTGVTAVAQKTVEGAGSIAAATGFVKKDQLGKN
EEGAPQEGILEDMPVDPDNEAYEMPSEEGYQDYEPEA

SNCA K45X

-continued (SEQ ID NO: 15)
MDVFMKGLSKAKEGVVAAAEKTKQGVAEAAGKTKEGVLYVGSKTXEGVVHGVATVAEKTKE

QVTNVGGAVVTGVTAVAQKTVEGAGSIAAATGFVKKDQLGKNEEGAPQEGILEDMPVDPDNE

AYEMPSEEGYQDYEPEA

6XHis SNCA K45X (SEQ ID NO: 16)
<u>MGSSHHHHHHSSGLVPRGSH</u>MDVFMKGLSKAKEGVVAAAEKTKQGVAEAAGKTKEGVLYVG

SKTXEGVVHGVATVAEKTKEQVTNVGGAVVTGVTAVAQKTVEGAGSIAAATGFVKKDQLGKN

EEGAPQEGILEDMPVDPDNEAYEMPSEEGYQDYEPEA

SNCA T59X (SEQ ID NO: 17)
MDVFMKGLSKAKEGVVAAAEKTKQGVAEAAGKTKEGVLYVGSKTKEGVVHGVATVAEKXKE

QVTNVGGAVVTGVTAVAQKTVEGAGSIAAATGFVKKDQLGKNEEGAPQEGILEDMPVDPDNE

AYEMPSEEGYQDYEPEA

6XHis SNCA T59X (SEQ ID NO: 18)
<u>MGSSHHHHHHSSGLVPRGSH</u>MDVFMKGLSKAKEGVVAAAEKTKQGVAEAAGKTKEGVLYVG

SKTKEGVVHGVATVAEKXKEQVTNVGGAVVTGVTAVAQKTVEGAGSIAAATGFVKKDQLGKN

EEGAPQEGILEDMPVDPDNEAYEMPSEEGYQDYEPEA

SNCA G67X (SEQ ID NO: 19)
MDVFMKGLSKAKEGVVAAAEKTKQGVAEAAGKTKEGVLYVGSKTKEGVVHGVATVAEKTKE

QVTNVXGAVVTGVTAVAQKTVEGAGSIAAATGFVKKDQLGKNEEGAPQEGILEDMPVDPDNE

AYEMPSEEGYQDYEPEA

6XHis SNCA G67X (SEQ ID NO: 20)
<u>MGSSHHHHHHSSGLVPRGSH</u>MDVFMKGLSKAKEGVVAAAEKTKQGVAEAAGKTKEGVLYVG

SKTKEGVVHGVATVAEKTKEQVTNVXGAVVTGVTAVAQKTVEGAGSIAAATGFVKKDQLGKN

EEGAPQEGILEDMPVDPDNEAYEMPSEEGYQDYEPEA

SNCA V77X (SEQ ID NO: 21)
MDVFMKGLSKAKEGVVAAAEKTKQGVAEAAGKTKEGVLYVGSKTKEGVVHGVATVAEKTKE

QVTNVGGAVVTGVTAXAQKTVEGAGSIAAATGFVKKDQLGKNEEGAPQEGILEDMPVDPDNE

AYEMPSEEGYQDYEPEA

6XHis SNCA V77X (SEQ ID NO: 22)
<u>MGSSHHHHHHSSGLVPRGSH</u>MDVFMKGLSKAKEGVVAAAEKTKQGVAEAAGKTKEGVLYVG

SKTKEGVVHGVATVAEKTKEQVTNVGGAVVTGVTAXAQKTVEGAGSIAAATGFVKKDQLGKN

EEGAPQEGILEDMPVDPDNEAYEMPSEEGYQDYEPEA

SNCA A78X (SEQ ID NO: 23)
MDVFMKGLSKAKEGVVAAAEKTKQGVAEAAGKTKEGVLYVGSKTKEGVVHGVATVAEKTKE

QVTNVGGAVVTGVTAVXQKTVEGAGSIAAATGFVKKDQLGKNEEGAPQEGILEDMPVDPDNE

AYEMPSEEGYQDYEPEA

6XHis SNCA A78X (SEQ ID NO: 24)
<u>MGSSHHHHHHSSGLVPRGSH</u>MDVFMKGLSKAKEGVVAAAEKTKQGVAEAAGKTKEGVLYVG

SKTKEGVVHGVATVAEKTKEQVTNVGGAVVTGVTAVXQKTVEGAGSIAAATGFVKKDQLGKN

EEGAPQEGILEDMPVDPDNEAYEMPSEEGYQDYEPEA

DETAILED DESCRIPTION OF SEVERAL EMBODIMENTS

Management of neurological diseases such as Parkinson disease and dementia with Lewy bodies remains a challenge and would greatly benefit from a diagnostic test that is both practical and sensitive enough for early, ante-mortem identification of a patient affected by synucleinopathies. There is currently no objective test for Parkinson disease, and the current methods can have an up to 50% misdiagnosis rate. A hallmark of Parkinson disease is the accumulation of abnormal deposits of αSyn in the brain, called Lewy bodies. Fibrils of misfolded αSyn form through the process of seeded polymerization, whereby misfolded forms of αSyn act as a template, or "seed" to propagate conversion of natively folded αSyn into the misfolded form as the aggregates grow. This pathogenic self-propagation process can be used in detection methods. Disclosed in an amplification assay that uses mutated rαSyn as a substrate. This assay allows rapid detection of misfolded αSyn in biological samples, such as, but not limited to, cerebrospinal fluid, blood, serum, plasma, and olfactory mucosa samples. Fractions of these biological samples can be used in these assays. The disclosed methods can be used to diagnose synucleinopathies, select cohorts for therapeutic trials, monitor effects of therapies on misfolded αSyn, and/or monitor subjects at risk, such as due to a genetic predisposition or environmental factors.

I. Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Aggregate: A group of molecules in association, such as oligomers, multimers and polymers of αSyn, such as amyloid fibrils of misfolded αSyn protein. Co-aggregates are aggregates of more than one type of molecule, such as, but not limited to, mutated rαSyn and misfolded αSyn.

Alzheimer disease: A chronic neurodegenerative disease that is the cause of 60% to 70% of cases of dementia. The most common early symptom is difficulty in remembering recent events (short-term memory loss). As the disease advances, symptoms can include problems with language, disorientation (including easily getting lost), mood swings, loss of motivation, not managing self-care, and behavioral issues. Although the speed of progression can vary, the average life expectancy following diagnosis is three to nine years.

Alzheimer disease is characterized by loss of neurons and synapses in the cerebral cortex and certain subcortical regions of the brain. This loss results in gross atrophy of the affected regions, including degeneration in the temporal lobe and parietal lobe, and parts of the frontal cortex and cingulate gyrus. Degeneration is also present in brainstem nuclei like the locus coeruleus. Both amyloid plaques and neurofibrillary tangles are clearly visible by microscopy in brains of patients. The plaques are dense, mostly insoluble deposits of beta-amyloid peptide and cellular material outside and around neurons. Tangles (neurofibrillary tangles) are aggregates of the microtubule-associated protein tau that accumulate inside the cells themselves. Aggregates of misfolded αSyn have been detected in the brains of a small minority of cases of Alzheimer disease, but this is not a consistent or defining feature of AD.

Agitation: Introducing any type of turbulence or motion into a mixture or reaction mix, for examples by sonication, stirring, or shaking. In some embodiments, agitation includes the use of force sufficient to fragment misfolded synuclein aggregates, which disperses the aggregates and/or polymers to facilitate further amplification. In some examples, fragmentation includes complete fragmentation, whereas in other examples, fragmentation is only partial, for instance, a population of aggregates can be about 1%, 2%, 5%, 10%, 20%, 30%, 40%, 50%, 60%, 70%, 80%, 90%, or 100% fragmented by agitation. Exemplary agitation methods are described in the Examples section below. In some embodiments, agitation includes shaking (and not sonication).

Amyloid: Fibrillar ultrastructure of protein aggregates that contains cross-beta structure and typically stains in characteristic ways with certain dyes such as thioflavin T (ThT). In the latter case, the fluorescence yield of the dye is enhanced by binding to amyloids. Many different proteins can form amyloids in association with a wide variety of diseases. Aggregates of αSyn can take the form of amyloid.

Antibody: A polypeptide ligand comprising at least a light chain or heavy chain immunoglobulin variable region which specifically recognizes and binds an epitope of an antigen or a fragment thereof. An antibody can specifically bind αSyn, such as misfolded αSyn, or a particular mutant rαSyn. Antibodies can be composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

The term antibody includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen, such as αSyn. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds an antigen of interest has a specific $V_H$ region and the $V_L$ region sequence, and thus specific CDR sequences. Antibodies with different specificities (due to different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected, or a progeny thereof. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

Antibody binding affinity: Affinity of an antibody for an antigen, such as αSyn. In one embodiment, affinity is calculated by a modification of the Scatchard method described by Frankel et al., Mol. Immunol., 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$ M, at least about $2.0 \times 10^{-8}$ M, at least about $2.5 \times 10^{-8}$ M, at least about $3.0 \times 10^{-8}$ M, at least about $3.5 \times 10^{-8}$ M, at least about $4.0 \times 10^{-8}$ M, at least about $4.5 \times 10^{-8}$ M, or at least about $5.0 \times 10^{-8}$ M.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T-cells respond. An antigen can be a tissue-specific antigen, or a disease-specific antigen, such as misfolded αSyn.

Conservative variant: In the context of a protein, refers to a peptide or amino acid sequence that deviates from another amino acid sequence only in the substitution of one or several amino acids for amino acids having similar biochemical properties (so-called conservative substitutions). Conservative amino acid substitutions are likely to have minimal impact on the activity of the resultant protein, such as in an RT-QuIC assay. Further information about conservative substitutions can be found, for instance, in Ben Bassat et al. (*J. Bacteriol.*, 169:751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. In some examples, protein variants can have no more than 1, 2, 3, 4, 5, 10, 15, 30, 45 conservative amino acid changes.

In one example, a conservative variant protein is one that functionally performs substantially like a similar base component, for instance, a rαSyn protein having conservative variations in the sequence as compared to a reference rαSyn protein. For example, a conservative variant of a mutated rαSyn protein, will aggregate with misfolded αSyn, and will form aggregates with the same reaction kinetics under similar reaction conditions. In this example, a mutated rαSyn protein and the conservative variant do not have the same amino acid sequences, but have changes at residues that do not substantially affect reaction kinetics. The conservative variant can have, for instance, one, two, three, four, or five substitutions in the amino acid sequence. However, a conservative variant of a mutant rαSyn still contains, for example, a) the one to eight point mutations in SEQ ID NO: 1, wherein the point mutations are at residues K23, D2, K21, K45, T59, G67, V77, and/or A78 (wherein the number is the position and the letter is the amino acid in the sequence) and/or b) the deletion of up to ten amino acids in amino acids 2-11 of SEQ ID NO: 1. The conservative amino acid substitutions can occur in any domain of the mutated rαSyn protein. However, generally the a) one to eight point mutations in SEQ ID NO: 1, wherein the point mutations are at residues K23, D2, K21, K45, T59, G67, V77, and/or A78 and/or b) a deletion of up to ten amino acids in amino acids 2-11 of SEQ ID NO: 1, is/are maintained.

Conditions sufficient to detect: Any environment that permits the desired activity, for example, that permits an interaction to be detected, or such as conditions that allow a detectable label to be detected. For example, such conditions include appropriate temperatures, buffer solutions, and detection means such as fluorimeters and digital imaging equipment.

Detect: To determine if an agent (such as a signal or protein, for example misfolded αSyn) is present or absent. In some examples, this can further include quantification, for example the quantification of the amount of αSyn protein in a sample, such as a cerebrospinal fluid, brain tissue, nasal brushing, blood sample, serum sample, tissue sample, or any other sample or a fraction of a sample.

Diagnostic: Identifying the presence or nature of a pathologic condition, such as, but not limited to, identifying the presence of misfolded αSyn protein and identifying a synucleinopathy. Diagnostic methods differ in their sensitivity and specificity. The "sensitivity" of a diagnostic assay is the percentage of diseased individuals (true positives) who test positive. The "specificity" of a diagnostic assay is 1 minus the false positive rate, where the false positive rate is defined as the proportion of those without the disease who test positive. While a particular diagnostic method may not provide a definitive diagnosis of a condition, it provides a positive indication that aids in diagnosis. "Prognostic" is the probability of development (for example severity) of a pathologic condition.

Disaggregate: To partially or completely disrupt an aggregate, such as an aggregate of misfolded αSyn protein.

Encode: Any process whereby the information in a polymeric macromolecule or sequence is used to direct the production of a second molecule or sequence that is different from the first molecule or sequence. As used herein, the term is construed broadly, and can have a variety of applications. In some aspects, the term "encode" describes the process of semi-conservative DNA replication, wherein one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (for instance, by the process of transcription incorporating a DNA-dependent RNA polymerase enzyme). Also, an RNA molecule can encode a peptide, such as αSyn, as in the process of translation. When used to describe the process of translation, the term "encode" also extends to the triplet codon that encodes an amino acid. In some aspects, an RNA molecule can encode a DNA molecule, for instance, by the process of reverse transcription incorporating an RNA-dependent DNA polymerase. In another aspect, a DNA molecule can encode a peptide, where it is understood that "encode" as used in that case incorporates both the processes of transcription and translation.

Fluorophore: A chemical compound, which when excited by exposure to a particular stimulus, such as a defined wavelength of light, emits light (fluoresces), for example at a different wavelength (such as a longer wavelength of light). Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) can eliminate the need for an external source of electromagnetic radiation, such as a laser. Thioflavin T and Thioflavin S are fluorophores of use for the detection of αSyn aggregates.

Non-limiting examples of particular fluorophores that can attached to antibodies that specifically binds αSyn, or αSyn aggregates are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others. In some examples, a fluorophore is detectable label, such as a detectable label attached to an antibody.

Immunoassay: A biochemical test that measures the presence or concentration of a substance in a sample, such as a biological sample, or fraction thereof, such as a nasal brushing or a blood sample, cerebrospinal fluid sample, brain tissue sample, or a serum sample obtained from a subject, using the reaction of an antibody to its cognate antigen, for example the specific binding of an antibody to a protein, such as misfolded αSyn. Both the presence of antigen or the amount of antigen present can be measured.

Immunoprecipitation (IP): The technique of precipitating a protein antigen out of solution using an antibody or peptides that specifically binds to that particular protein. These solutions will often be in the form of a crude lysate of an animal tissue. Other sample types could be body fluids or other samples of biological origin. Generally, in IP the antibody or peptides are coupled to a solid substrate at some point in the procedure. Antibodies are commercially available that bind total synuclein, oligomeric synuclein and phosphosynuclein.

Isolated: An "isolated" biological component, such as a peptide or assembly of polypeptides (for example, soluble or misfolded αSyn), cell, nucleic acid, or serum samples has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a cell as well as chemically synthesized peptide and nucleic acids. The term "isolated" or "purified" does not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation, such as at least 50%, at least 60%, at least 70%, at least 80%, at least 90%, at least 95%, or even at least 99% of the peptide or protein concentration.

Misfolded: A protein, such as αSyn, that no longer contains all or part of the structural conformation of the protein as it exists when involved in its typical, nonpathogenic normal function within a biological system. Misfolded αSyn can take the form of oligomers and aggregates. A misfolded protein can be the pathogenic form.

Multiple System Atrophy: A neurodegenerative disease characterized by a combination of autonomic, cerebellar, parkinsonian and pyramidal symptoms, also known as olivopontocerebellar atrophy, striatonigral degeneration and Shy-Drager syndrome. MSA is divided into categories based on the motor phenotype; MSA is divided into the parkinsonian (MSA-P) and cerebellar (MSA-C) variants. MSA-P is only poorly L-DOPA-responsive. In most countries, MSA-P is more common than MSA-C. Like Parkinson disease, the onset of MSA is usually in the sixth decade of life, but it progresses faster than PD. The mean survival time of a patient with MSA from the onset of symptoms is usually 6-10 years.

Proteinaceous oligodendroglial cytoplasmic inclusions (Papp-Lantos bodies) are the major histological hallmark of MSA. Less often, oligodendroglial nuclear inclusions are present, as are neuronal cytoplasmic and nuclear inclusions. Schwann cell cytoplasmic inclusions are also a common feature Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single and double stranded forms of DNA. A nucleic acid molecule can include either or both naturally occurring and modified nucleotides linked together by naturally occurring and/or non-naturally occurring nucleotide linkages.

Parkinson disease: A degenerative disorder of the central nervous system that impairs motor skills, cognitive processes, and other functions. Parkinson disease is also referred to as Parkinson disease, Parkinson, PD and primary Parkinsonism. The most obvious symptoms of Parkinson disease are motor-related, including tremor, rigidity, slowness of movement and postural instability. Among non-motor symptoms are autonomic dysfunction and sensory and sleep difficulties. Cognitive and neurobehavioral problems, including dementia, are common in the advanced stages of the disease.

In subjects that develop Parkinson disease, symptoms typically begin around the age of 60, although there are young-onset cases. Symptoms result from insufficient formation and action of dopamine produced in the dopaminergic neurons of the midbrain (specifically the substantia nigra). Pathologically the disease is characterized by the accumulation of misfolded αSyn forming inclusions called Lewy bodies. Such pathology can only be demonstrated at autopsy so diagnosis is mainly clinical (based on symptoms). Some tests such as neuroimaging techniques can also aid in diagnosis.

Pick Disease: A type of frontotemporal degeneration that is a rare neurodegenerative disease that causes progressive destruction of neurons in the brain. Symptoms include loss of language (aphasia), movement disorders and/or dementia. While some of the symptoms can initially be alleviated, the disease progresses and patients often die within two to ten years. A defining characteristic of the disease is build-up of tau proteins in neurons, accumulating into silver-staining, spherical aggregations known as "Pick bodies." Pick bodies are almost always found in several regions in the brain, including the dentate gyrus, the pyramidal cells of the CA1 sector and subiculum of the hippocampus, the neocortex, and a plurality of other nuclei. Changes in personality help Pick disease to be distinguished from Alzheimer disease. Symptoms include difficulty in language and thinking, efforts to dissociate from family, behavioral changes, unwarranted anxiety, irrational fears, impaired regulation of social conduct (e.g., breaches of etiquette, vulgar language, tactlessness, disinhibition, misperception), passivity, low motivation (aboulia), inertia, over-activity, pacing and wandering.

PMCA or Protein Misfolding Cyclic Amplification: A method for amplifying a protein, such as misfolded rαSyn, in a sample by mixing a substrate with the sample, incubating the reaction mix to permit the substrate to initiate the conversion of a mutant rαSyn protein to aggregates, fragmenting any aggregates formed during the incubation step by sonication, and repeating one or more cycles of the incubation and fragmentation steps.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell.

QuIC or Quaking Induced Conversion: A particular type of rαSyn seed detection assay, in which shaking of the reaction vessels is performed instead of sonication to agitate the reaction. An "alpha (a) synuclein seeding assay" or a "seeded synuclein polymerization assay" is an assay for misfolded αSyn seeds that induces aggregate formation from mutated rαSyn.

Real Time (RT)-QuIC: A type of QuIC assay that includes intermittent shaking without sonication to agitate the reaction and includes the use of a fluorescent readout, such as the fluorescent dye thioflavin T (ThT) of thioflavin S (ThS) to detect amyloid produced by a seeding assay. Exemplary protocols are disclosed, for example, in Wilham et al., PLOS Pathog. 6(12): e1001217, pages 1-15. In the presently disclosed methods, this assay can use a mutated rαSyn protein as a substrate, intermittently shaken reactions, and can be predominantly detergent-free or use low levels of detergent (such as 0-0.1% of SDS or 0.001%-0.005% SDS). The assay includes fluorescent detection of αSyn aggregates. Both QuIC and RT-QuIC can be used to detect misfolded αSyn, with synuclein seeding activity, from a biological sample or fraction thereof. In some examples, misfolded αSyn protein is detected by the production of ThT-reactive forms of αSyn in this assay.

Sample: A biological sample obtained from a subject, such as a human or veterinary subject, which contains for example nucleic acids and/or proteins. As used herein, biological samples include all clinical samples useful for detection of misfolded αSyn in subjects, including, but not limited to, nasal brushings, saliva, cells, tissues (e.g., brain tissue or skin tissue), and bodily fluids, such as: blood; derivatives and fractions of blood, such as serum; extracted galls; biopsied. A sample can be surgically removed tissue, including tissues that are, for example, unfixed, frozen, fixed in formalin and/or embedded in paraffin. Samples can be tears; milk; skin scrapes; surface washings; urine; sputum; cerebrospinal fluid; prostate fluid; pus; muscle; lymphoid tissues; olfactory mucosa; urine; feces; or bone marrow aspirates. A tissue sample can be any tissue of interest, such as brain tissue. The sample can be cerebrospinal fluid. In some embodiments, a sample may be contacted in solution with an agent, such as but not limited to a mutated form of rαSyn protein or an antibody that specifically binds mutated rαSyn protein. In other embodiments, a sample may be contacted in solid phase with an agent, such as but not limited to a mutated form of rαSyn protein or an antibody that specifically binds mutated rαSyn protein. In other embodiments, a sample may be contacted in solution and in solid phase with an agent, such as but not limited to a mutated form of rαSyn protein or an antibody that specifically binds mutated rαSyn protein. A "fraction" of a biological sample is any portion, component, concentrate, or purified element from a biological sample. An exemplary fraction can be prepared by contacting a biological sample with particles that bind αSyn protein. These fractions, including the particles, are of use in the methods disclosed herein.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences. Methods for aligning sequences for comparison are described in detail below, in the Detailed Description.

Single Round: Performing a method wherein serial amplification reactions are not performed. For example, misfolded αSyn can be amplified in a sample, by mixing the sample with purified mutant rαSyn to make a reaction mix; performing an amplification reaction that includes (i) incubating the reaction mix to permit coaggregation of the soluble mutated rαSyn with misfolded αSyn that may be present in the reaction mix, and maintaining incubation conditions that promote coaggregation of the soluble mutated rαSyn with the misfolded αSyn and result in a conversion of the soluble mutated rαSyn to misfolded rαSyn aggregates initiated by the presence of misfolded αSyn in the sample, while inhibiting development of spontaneously mutated rαSyn aggregates; (ii) agitating aggregates formed during step (i) in shaking cycles; (iii) optionally repeating steps (i) and (ii) one or more times. Misfolded rαSyn aggregates are detected in the reaction mix, wherein detection of misfolded rαSyn aggregates in the reaction mix indicates that misfolded αSyn was present in the sample. In a single round reaction, a portion of the reaction mix is not removed and incubated with additional mutated rαSyn in a separate reaction mixture.

Sonication: The process of disrupting or dispersing biological materials using sound wave energy.

Specific binding agent: An agent that binds substantially only to a defined target. In some embodiments, a specific binding agent is an antibody that specifically binds misfolded αSyn.

The term "specifically binds" refers to the preferential association of an antibody or other ligand, in whole or part, with an antigen. Specific binding may be distinguished as mediated through specific recognition of the antigen. Although selectively reactive antibodies bind antigen, they may do so with low affinity. On the other hand, specific binding results in a much stronger association between the antibody (or other ligand) and antigen (or cells bearing the antigen) than between the bound antibody (or other ligand) and another protein (or cells lacking the antigen). Specific binding typically results in greater than 2-fold, such as greater than 5-fold, greater than 10-fold, or greater than 100-fold increase in amount of bound antibody or other ligand (per unit time) to a cell or tissue expressing the target epitope as compared to a cell or tissue lacking this epitope. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Synucleln: The synuclein family includes α, β and γ synuclein. Alpha synuclecin (αSyn) is abundant in the human brain. It is believed to pay a role in maintaining a supply of synaptic vesicles in presynaptic terminals. The wild-type human αSyn protein is made of 140 amino acids and is encoded by the SNCA gene. An exemplary wild-type human αSyn sequence is shown in SEQ ID NO: 1. Exemplary mRNA and protein sequences for human αSyn are provided in GENBANK® Accession No. NM_000345.3, Sep. 15, 2017, incorporated herein by reference, and Accession Number: NP_000336.1, as available on Sep. 12, 2017. Exemplary mRNA and protein sequences for mouse αSyn are provided in GENBANK® Accession No. NM_001042451.2, Sep. 18, 2017, incorporated herein by reference. There are three domains of wild-type αSyn. Residues 1-60 are an amphipathic N-terminal region dominated by four 11-residue repeats including the consensus sequence KTKEGV (amino acids 21-26 of SEQ ID NO: 1). This sequence has a structural alpha helix propensity similar to apolipoproteins-binding domains. Residues 61-95 are a central hydrophobic region which includes the non-amyloid-β component (NAC) region, involved in protein aggregation. Residues 96-140 are a highly acidic and proline-rich region which has no distinct structural propensity. In some embodiments, an αSyn polypeptide includes 1-10 point mutations, such as 1, 2, 3, 4, 5, 6, 7, 8, 9, or 10 point mutations as compared with SEQ ID NO: 1. Point mutation include, but are not limited to, mutations a K23, D2, K21, K45, T59, G67, V77, A78. An αSyn polypeptide can also include a deletion of up to 11 amino acids, such as in residues 1-60. An exemplary αSyn deletion of use has a deletion comprising, or consisting of, amino acids 2-11.

Misfolded αSyn can aggregate or oligomerize to form insoluble aggregates and/or higher oligomers, leading to the formation of αSyn aggregates that can be in the form of protofibrils, fibrils, plaques or inclusion bodies. "Soluble" αSyn remains in solution in biological fluids and pharmaceutically acceptable carriers. "Aggregates" of misfolded αSyn can precipitate and form fibrils, deposits, tangles, plaques, or other forms that are insoluble in biological fluids and pharmaceutically acceptable carriers. "Seed" refers to misfolded αSyn aggregates with catalytic or templating activity for inducing further misfolding, oligomerization, and/or aggregation.

Synucleinopathy: A disease wherein Lewy bodies, including misfolded synuclein, are present. Synucleinopathies include, but are not limited to, Parkinson disease (PD), MSA and Lewy body dementia. A list of exemplary synucleinopathies is provided in a Table below. Lewy body dementia (LBD) is a progressive brain disorder in which Lewy bodies (abnormal deposits of αSyn) build up in areas of the brain that regulate behavior, cognition, and/or movement. LBD is a term that includes two clinical diagnoses: Parkinson disease dementia and dementia with Lewy bodies (DLB). PD has a more dopamine associated deposition of αSyn and DLB has a more diffuse deposition throughout the brain. Insoluble aggregates in brain tissue that include αSyn (Lewy bodies) are associated with multiple neurological disorders, including neurodegenerative diseases, Parkinson disease and DLB. A disorder associated with a αSyn aggregates in brain tissue is referred to as synucleinopathy. The presence of Lewy bodies in neurons of the substantia nigra is the histopathological hallmark of Parkinson disease, and Lewy bodies are found in brain tissue in DLB.

Truncated: A protein that is not the full-length native sequence, and thus includes fewer amino acids than the native protein. In some embodiments, a truncated protein, such as a mutated rαSyn protein, does not include N-terminal amino acids, such as amino acids 2-11 of a wild-type αSyn.

Unless otherwise explained, all technical and scientific terms used herein have the same meaning as commonly understood by one of ordinary skill in the art to which this disclosure belongs. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In addition, the materials, methods, and examples are illustrative only and not intended to be limiting.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (see, for instance, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999).

II. Overview of Several Embodiments

Methods are disclosed herein for determining whether a subject has a synucleinopathy. The subject can be a human. The synucleinopathy can be, for example, Parkinson disease, Dementia with Lewy Bodies, or multiple system atrophy. Additional synucleinopathies are disclosed below (see the Table).

In some embodiments, the methods include performing an αSyn seeding assay on a biological sample from the subject, or a fraction thereof. The biological sample can be a nasal brushing, saliva, skin, blood, serum, plasma, cerebrospinal fluid, feces, urine or tissue sample, such as, but not limited to, a brain tissue sample. The fraction can be produced by incubating the biological sample with IO particles, optionally washing the particles, and using the IO particles in the reaction mix. In further embodiments, the assay includes: contacting a biological sample or fraction thereof with a soluble mutated rαSyn to form a first reaction mixture, wherein the soluble mutated rαSyn includes an amino acid sequence a) comprising one to eight point mutations in SEQ ID NO: 1, wherein the point mutations are at residues K23, D2, K21, K45, T59, G67, V77, and/or A78 and/or b) a deletion of up to ten amino acids in amino acids 2-11 of SEQ ID NO: 1. Any amino acid can be inserted at amino acids K23, D2, K21, K45, T59, G67, V77, and A78. The reaction mixture is incubated to permit coaggregation of misfolded αSyn aggregates present in the biological sample, or fraction thereof, with the mutated rαSyn, and incubation conditions are maintained that promote coaggregation of the mutated rαSyn with the misfolded αSyn aggregates to result in a conversion of the soluble mutated rαSyn to mutated rαSyn aggregates while inhibiting spontaneous aggregation of soluble mutant rαSyn. Mutated rαSyn aggregates (that include misfolded mutated rαSyn) that are formed are agitated wherein the conditions include shaking the reaction mixture in a shaking cycle, wherein each shaking cycle comprises a period of rest and a period of shaking. Misfolded mutated rαSyn aggregates are detected in the reaction mixture. Detection of misfolded mutated rαSyn aggregates in the reaction mixture indicates that the subject has the synucleinopathy.

In some embodiments, the soluble mutated rαSyn can include the amino acid sequence of one of SEQ ID NO: 3, 5, 7, 9, 11, 13, 15, 17, 19, 21, or 23. In further embodiments, the soluble mutated rαSyn can consist of the amino acid sequence of one of SEQ ID NO: 3, 5, 7, 9, 11, 13, 15, 17, 19, 21, or 23. In additional embodiments, the soluble misfolded rαSyn can include the amino acid sequence of one of SEQ ID NOs: 4, 6, 8, 10, 12, 14, 16, 18, 20, 22 or 24. In more embodiments, the soluble misfolded rαSyn can consist of the amino acid sequence of one of SEQ ID NOs: 4, 6, 8, 10, 12, 14, 16, 18, 20, 22 or 24. When the mutated rαSyn includes at least six histidines, the protein can be purified using immobilized metal ion affinity chromatography, such as, but not limited to, nickel ion affinity chromatography.

In further embodiments, detecting the presence of misfolded mutated rαSyn aggregates comprises the use of fluorescence. In some embodiments, the presence of mutated rαSyn aggregates can be detected using an amyloid-sensing dye. The dye can be, for example, thioflavin T or thioflavin S. Thus, the reaction mix can include thioflavin T (ThT), and detecting mutated rαSyn aggregates can include detecting fluorescence. In more embodiments, misfolded mutated rαSyn aggregates can be detected within 24-48 hours. In other embodiments, misfolded mutated rαSyn aggregates can be detected after 18-35 hours. Additional embodiments are disclosed below.

In additional embodiments, agitating aggregates can include agitating aggregates in the absence of sonication. In further embodiments, period of rest and the period of shaking are substantially equal in the shaking cycle. The shaking cycle can be 20 to 180 seconds in length. In some examples, the period of rest and the period of shaking are each 30-60 seconds in length, such as 60 seconds in length.

In further embodiments, the incubation conditions include the use of a temperature of about 30 to about 55° C. In some non-limiting examples, the incubation conditions include the use of a temperature of about 42° C.

The incubation conditions can include 0-0.1% sodium dodecyl sulfate (SDS). In some embodiments, the incubation conditions include SDS. In some non-limiting examples, the incubation conditions include 0.001%-0.005% SDS.

In more embodiments, the reaction mixture includes 1 to 10 beads per 100 µl, such as wherein the reaction mixture comprises 6 beads per 100 µl. The beads can be about 0.5 mm to about 3 mm in diameter, such as about 1 mm in diameter. In some embodiments, the beads are glass.

Methods are also provided for detecting misfolded αSyn in a biological sample or fraction thereof. The biological sample can be from a human. In some embodiments, the biological sample is a nasal brushing, saliva, skin, blood, serum, plasma, cerebrospinal fluid, feces, urine or tissue sample, such as a brain tissue sample. These methods include (a) mixing the biological sample or fraction thereof with a purified soluble mutated rαSyn to make a reaction mix, wherein the soluble mutated rαSyn includes an amino acid sequence a) comprising one to eight point mutations in SEQ ID NO: 1, wherein the point mutations are at residues K23, D2, K21, K45, T59, G67, V77, and/or A78 and/or b) with a deletion of up to ten amino acids in amino acids 2-11 of SEQ ID NO: 1.

The methods also include (b) performing an amplification reaction that includes the steps of (i) incubating the reaction mix to permit coaggregation of the soluble mutated rαSyn with misfolded αSyn that may be present in the reaction mix, and maintaining incubation conditions that promote coaggregation of the soluble mutated rαSyn with the misfolded αSyn and result in a conversion of the soluble mutated rαSyn to misfolded rαSyn aggregates initiated by the presence of misfolded αSyn in the sample, while inhibiting development of spontaneously arising rαSyn aggregates; and (ii) agitating aggregates formed during step (i), in shaking cycles, wherein each shaking cycle of the shaking cycles comprises a period of rest and a period of shaking, wherein agitating is performed in the absence of sonication. Furthermore, the methods include (c) detecting misfolded rαSyn aggregates in the reaction mix, and detection of misfolded rαSyn in the reaction mix indicates that misfolded αSyn was present in the biological sample.

In some embodiments, the presence of misfolded αSyn in a biological sample or fraction thereof indicates that the subject from whom the sample was taken has a synucleinopathy. The synucleinopathy can be, for example, Parkinson disease, Lewy body dementia, or multiple system atrophy.

The soluble mutated rαSyn can include the amino acid sequence of one of SEQ ID NO: 3, 5, 7, 9, 11, 13, 15, 17, 19, 21, or 23. The soluble mutated rαSyn can consist of the amino acid sequence of one of SEQ ID NO: 3, 5, 7, 9, 11, 13, 15, 17, 19, 21, or 23. The soluble misfolded rαSyn can include the amino acid sequence of one of SEQ ID NOs: 4, 6, 8, 10, 12, 14, 16, 18, 20, 22 or 24. The soluble misfolded rαSyn can consist of the amino acid sequence of one of SEQ ID NOs: 4, 6, 8, 10, 12, 14, 16, 18, 20, 22 or 24. When the mutated rαSyn includes at least six histidines, the protein can be purified using immobilized metal ion affinity chromatography, such as, but not limited to, nickel ion affinity chromatography.

In some embodiments, detecting the presence of misfolded mutated rαSyn aggregates comprises the use of fluorescence. In some embodiments, the presence of mutated rαSyn aggregates can be detected using an amyloid-sensing dye. The dye can be, for example, thioflavin T or thioflavin S. Thus, the reaction mix can include thioflavin T (ThT), and detecting mutated rαSyn aggregates can include detecting fluorescence. In more embodiments, misfolded mutated rαSyn aggregates can be detected within 24-48 hours. Other embodiments are disclosed below.

In further embodiments, agitating aggregates in step (ii) comprises agitating aggregates in the absence of sonication. In yet other embodiments, the period of rest and the period of shaking are substantially equal in the shaking cycle in step (ii). In some non-limiting examples, the shaking cycle in step (ii) is 20 to 180 seconds in length. In other non-limiting examples, the period of rest and the period of shaking are each 30-60 seconds in length. For example, the period of rest and the period of shaking can be each 60 seconds in length.

In yet other embodiments, the amplification reaction is performed at a temperature of about 30 to about 55° C., such as at a temperature of about 42° C.

In further embodiments, the amplification reaction comprises 0-0.1% SDS. The amplification reactions can include SDS. In some non-limiting examples, the amplification reaction comprises 0.001%-0.005% sodium dodecyl sulfate.

In additional embodiments, misfolded mutated rαSyn aggregates can be detected within 24-48 hours.

In yet other embodiments, the reaction mix includes 1 to 10 beads per 100 µl. In some non-limiting examples, the reaction mix includes 6 glass beads per 100 µl. In more embodiments, the beads are about 0.5 mm to about 3 mm in diameter, such as about 1 mm in diameter. In other non-limiting examples, the beads are glass.

III. Substrates

Disclosed herein are methods for determining whether a subject has a synucleinopathy using a seeded αSyn polymerization assay, which is performed on a biological sample from the subject, or fraction thereof. Also disclosed herein are methods for determining if misfolded αSyn is present in a sample, such as a biological sample. In these assays, the sample is contacted with a purified mutated recombinant α-synuclein (rαSyn), wherein the mutated rαSyn has point mutations at residues K23, D2, K21, K45, T59, G67, V77, and/or A78 and/or b) a deletion of up to ten amino acids in amino acids 2-11 of the amino terminus.

A reference sequence for human αSyn is provided as SEQ ID NO: 1. Thus, references to positions, such as K23, D2, K21, K45, T59, G67, V77, and/or A78, or deletion of amino acids 2-11, with regard to the sequence shown in SEQ ID NO: 1. Exemplary amino acid sequences of use in the disclosed assays are provided as SEQ ID NOs: 3-24.

In some embodiments, the mutated rαSyn can include one of SEQ ID NO: 3, 5, 7, 9, 11, 13, 15, 17, 19, 21, or 23. While the mutated rαSyn can consist of one of SEQ ID NOs: 3, 5, 7, 9, 11, 13, 15, 17, 19, 21, or 23, it need not be limited to this sequence.

In one example, a conservative variant rαSyn can be utilized, that functionally performs substantially like the reference mutant rαSyn. For example, a conservative variant of a mutated rαSyn protein, will aggregate with misfolded αSyn, and will form aggregates with substantially the same kinetics under similar reaction conditions. In this example, a mutated rαSyn protein and the conservative variant do not have the same amino acid sequences, but have changes at residues that do not substantially affect reaction kinetics. The conservative variant can have, for instance, one, two, three, four, or five substitutions in the amino acid sequence. However, a conservative variant of a mutant rαSyn still contains, for example, a) the one to eight point mutations in SEQ ID NO: 1, wherein the point mutations are at residues K23, D2, K21, K45, T59, G67, V77, and/or A78 and/or b) the deletion of up to ten amino acids in amino acids 2-11. The conservative amino acid substitutions can occur in any domain of the mutated rαSyn protein. However, generally the a) one to eight point mutations in SEQ ID NO: 1, wherein the point mutations are at residues K23, D2, K21, K45, T59, G67, V77, and/or A78 and/or b) a deletion of up to ten amino acids in amino acids 2-11 of SEQ ID NO: 1, is/are maintained.

In additional embodiments, 1-20 amino acids, such as 1, 2, 3, 4, 5, 6, 7, 8, 9, 10, 11, 12, 13, 14, 15, 16, 17, 18, 19, or 20 amino acids can be added to the amino or carboxyl terminus of the mutated rαSyn. These amino acids can be any amino acids. In some non-limiting examples, 1, 2, 3, 4, 5, 6, 7, 8, 9 or 10 histidines can be added at either the amino or carboxyl terminus of a mutated rαSyn for purification purposes. Linkers can also be added. The mutated rαSyn protein can include for example, 6, 7, 8, 9 or 10 histidines at either the N or the C terminus. Exemplary mutated rαSyn that include additional amino acids are shown in SEQ ID NOs: 4, 6, 8, 10, 12, 14, 16, 18, 20, 22 or 24. Thus, the mutated rαSyn can include the amino acid sequence of one of SEQ ID NOs: 4, 6, 8, 10, 12, 14, 16, 18, 20, 22 or 24. The mutated rαSyn can consist of the amino acid sequence of one of SEQ ID NOs: 4, 6, 8, 10, 12, 14, 16, 18, 20, 22 or 24. The embodiments are not mutually exclusive. Thus, additional amino acids can be added at the amino and/or carboxyl terminus, and conservative substitutions can also be included.

One of skill in the art can readily produce mutated rαSyn protein that includes one or more amino acid substitutions at K23, D2, K21, K45, T59, G67, V77, and/or A78. In some embodiments, the mutated rαSyn includes 2, 3, 4, 5, 6, 7 or all 8 of these mutations. As noted above, the mutated rαSyn can also be a deletion mutant, wherein amino acids 2-11 are deleted. The mutated rαSyn can also be a deletion mutant, wherein amino acids 2-11 are deleted, and also can include 1, 2, 3, 4, 5, 6, or 7 mutations at positions K23, D2, K21, K45, T59, G67, V77, and/or A78 (with reference to the wild-type sequence, e.g., SEQ ID NO: 1). Mutated rαSyn or conservative variants that include these amino acid sequences are of use in the methods disclosed herein. Mutated rαSyn or conservative variants that consist of these amino acid sequences are of use in the methods disclosed herein. As discussed above, an additional 1, 2, 3, 4, 5, 6, 7, 8, 9, or 10 amino acids can be added to the amino or carboxyl terminus of the mutated rαSyn. These polypeptides are all of use in the methods disclosed herein.

The mutated rαSyn disclosed herein can be obtained by methods well-known in the art for recombinant peptide expression and purification. A DNA molecule encoding a mutated rαSyn can be generated. The DNA sequence is deduced from the protein sequence based on known codon usage. See, e.g., Old and Primrose, Principles of Gene Manipulation $3^{rd}$ ed., Blackwell Scientific Publications, 1985; Wada et al., Nucleic Acids Res. 20: 2111-2118 (1992). In some embodiments, the DNA molecule includes additional sequence, for example recognition sites for restriction enzymes which facilitate its cloning into a suitable cloning vector, such as a plasmid. Nucleic acids are provided including the coding regions, non-coding regions, or both, either alone or cloned in a recombinant vector, as well as oligonucleotides and related primer and primer pairs corresponding thereto. Nucleic acids may be DNA, RNA, or a combination thereof. Vectors can be expression vectors. Nucleic acids encoding mutated rαSyn polypeptides may be obtained by any method known within the art (e.g., by PCR amplification using synthetic primers hybridizable to the 3'- and 5'-termini of the sequence and/or by cloning from a cDNA or genomic library using an oligonucleotide sequence specific for the given gene sequence, or the like). Nucleic acids can also be generated by chemical synthesis.

Any of the methodologies known within the relevant art regarding the insertion of nucleic acid fragments into a vector may be used to construct expression vectors that contain a chimeric gene comprised of the appropriate transcriptional/translational control signals and peptide-coding sequences. Promoter/enhancer sequences within expression vectors can be plant, animal, insect, or fungus regulatory sequences. An inducible or constitutive promoter can be operably linked to a nucleic acid encoding an engineered chloride channel receptor. In some embodiments, the expression of the polypeptides encoded by the vectors are controlled by a constitutive promoter. Suitable promoters include, but are not limited to, the T7 promoter. In other embodiments, the expression of the polypeptides encoded by the vectors are controlled by an inducible or repressible promoter. Typically, the promoter is a constitutive promoter that results in high levels of transcription upon introduction into a host cell in the absence of additional factors. Optionally, the transcription control sequences include one or more enhancer elements, which are binding recognition sites for one or more transcription factors that increase transcription above that observed for the minimal promoter alone.

It may be desirable to include a polyadenylation signal to effect proper termination and polyadenylation of the gene transcript. Exemplary polyadenylation signals have been isolated from bovine growth hormone, SV40 and the herpes simplex virus thymidine kinase genes. Any of these or other polyadenylation signals can be utilized in the context of the adenovirus vectors described herein.

Thus, in one embodiment, the polynucleotide encoding a mutated rαSyn is included in a vector for expression. Suitable viral vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus, yeast and the like. A vector can also be used for expression in bacterial cells. Such vectors are known in the art, and include, for example, plasmids such as pBR322.

Any of the disclosed vectors can be expressed in suitable host cells. Following expression in host cells, such as eukaryotic or prokaryotic host cell, the recombinant mutated rαSyn is purified.

The inclusion of at least six histidines facilitates purification by immobilized metal ion affinity chromatography. Immobilized metal affinity chromatography (IMAC), also known as metal chelate affinity chromatography (MCAC), is a specialized aspect of affinity chromatography. The principle behind IMAC lies in the fact that many metal ions, i.e., nickel, zinc, cobalt and copper, can coordinate to the amino acids histidine, cysteine, and tryptophan via electron donor groups on the amino acid side chains. To utilize this interaction for chromatographic purposes, the metal ion must be immobilized onto an insoluble support. This can be done by attaching a chelating group to the chromatographic matrix. The most common chelating group used in this technique is iminodiacetic acid (IDA). It is coupled to a matrix such as SEPHAROSE 6B, via a long hydrophilic spacer arm. The spacer arm ensures that the chelating metal is fully accessible to all available binding sites on a protein. Another chelating group is tris(carboxymethyl)-ethylenediamine (TED). $Cu^{++}$, $Ni^{++}$, and $Co^{++}$ are also applied for certain proteins. Interactions between immobilized metals and tryptophan, tyrosine, or cysteine residues of proteins have been reported, however, these are generally weaker interactions.

In some embodiments, a solution including the protein of interest, such as a mutated rαSyn, is used at a physiological pH, such as a pH of about 7.2 to 7.8, such as about 7.4 to about 7.6, such as about 7.5. The solution is applied to an IMAC column, so that the protein binds to the column, and eluting the protein from the column, see U.S. Pat. No. 5,932,102, incorporated herein by reference. In some embodiments, the resin is washed with Tris buffer to remove proteins that do not specifically interact with the metal, such as a nickel ion. With nickel chromatography methods, washing efficiency can be improved by the addition of imidazole. One of skill in the art can readily use metal ion chromatography for the purification of proteins. The purification can use metal ion chromatography, and/or ion exchange chromatography.

In some embodiments, the column is washed, and then eluted with, for example, with 10 mM to 500 mM imidazole, such as about 50 mM imidazole to 500 mM imidazole, for example about 100 mM imidazole to about 500 mM imidazole or 150 mM imidazole to about 250 mM imidazole. One suitable, non-limiting buffer includes about 20 mM Tris, pH 7.5, and 500 mM imidazole. Another suitable, non-limiting buffer includes about 20 mM Tris, pH 7.5, and 50 mM imidazole.

In some embodiments, a solution including the protein of interest, such as a mutated rαSyn, is used at a pH of about 7.2 to 7.8, such as about 7.4 to about 7.6, such as about 7.5. The solution is applied to an anion-exchange column, so that the protein binds to the column, and then the protein is eluted from the column, see Paslawski et al., Methods Mol Biol. 2016; 1345:133-50. doi: 10.1007/978-1-4939-2978-8_9. In some embodiments, the resin is washed with Tris buffer to remove proteins that do not specifically interact with the resin, such as, but not limited to, Q-HP. With ion exchange chromatography methods, washing efficiency can be improved by the addition of salt, such as NaCl. One of skill in the art can readily use ion exchange chromatography for the purification of proteins.

In some embodiments, the column is washed, and then eluted with, for example, with up to 100 mM and up to 1000 mM NaCl, such as about 100 mM imidazole and 500 mM NaCl, for example about 50 mM imidazole to about 100 mM NaCl or 250 mM imidazole to about 1000 mM NaCl. One suitable, non-limiting buffer includes about 20 mM Tris, pH 7.5, and 1000 mM NaCl.

IV. α Synuclein RT-QuIC

Methods are disclosed herein for detecting misfolded αSyn in a biological sample, or fraction thereof, and determining whether a subject has a synucleinopathy. Synucleinopathies include, but are not limited to, the diseases listed in the table below (from Galvin et al., *Arch Neurol.* 2001; 58(2):186-190):

| Synucleinopathies* |
| --- |
| Parkinson disease |
| Sporadic<br>Familial with αS mutations<br>Familial with mutations other than αS<br>Dementia with Lewy bodies |
| "Pure" Lewy body dementia<br>Lewy body variant of Alzheimer disease<br>Familial Alzheimer disease with AFP mutations<br>Familial Alzheimer disease with PS-1 mutations<br>Familial Alzheimer disease with PS-2 mutations<br>Down syndrome<br>Multiple system atrophy |
| Shy-Drager syndrome<br>Striatonigral degeneration<br>Olivopontocerebellar atrophy<br>Neurodegeneration with brain iron accumulation, type 1 |
| Hallervorden-Spatz syndrome<br>Neuroaxonal dystrophy<br>Other diseases that may have synuclein-immunoreactive lesions |
| Traumatic brain injury<br>Pick disease<br>Amyotrophic lateral sclerosis |

*αS indicates α-synuclein;
APP, amyloid precursor protein; and
PS-1 and PS-2, presenilin-1 and -2.

Synucleinopathies include diseases wherein Lewy bodies are present. Synucleinopathies include, but are not limit to, Parkinson disease, multiple system atrophy (MSA) and Lewy body dementias. In some embodiments, the methods include selecting a subject suspected of having, or that has, a synucleinopathy, such as, but not limited to, Parkinson disease, MSA, and Lewy body dementias. Thus, the disclosed methods can be used to diagnose, or confirm the diagnosis of, a synucleinopathy. The disclosed methods can also be used to detect αSyn in a sample from any subject of interest, including subjects that are at risk for developing a synucleinopathy, or a subject suspected of having a synucleinopathy.

These methods are of use with any biological sample of interest, or a fraction of the biological sample of interest. The biological sample from a subject can be, but not is not limited to, a brain homogenate and/or a cerebrospinal fluid sample. In some embodiments, the biological sample is a nasal brushing, skin, saliva, cerebrospinal fluid, blood, fecal, tissue, urine, or serum sample. If the biological sample is a tissue sample, it can be any tissue of interest, including a brain sample, or nasal brushing, saliva, skin, blood, serum, plasma, cerebrospinal fluid, feces, urine or tissue sample. The tissue can be fresh tissue or fixed tissue, such as formalin-fixed tissue. In some specific non-limiting examples, the same is a cerebrospinal fluid sample.

The sample can be diluted, such as in a buffer. In some embodiments, serial dilutions of the sample are tested. The sample can be diluted, for example, at $10^{-1}$, $10^{-2}$, $10^{-3}$, $10^{-4}$, $10^{-5}$, $10^{-6}$, $10^{-7}$, $10^{-8}$, $10^{-9}$ or $10^{-10}$ dilution.

A fraction of the biological sample can be prepared. In some embodiments, to prepare the fraction, the biological sample can be contacted with particles comprising a paramagnetic material, such as, but not limited to, IO, that allows the separation of components that bind to the surface of the particles. The particles can allow the extraction or concentration of αSyn from the biological sample, prior to performing an amplification reaction, such as QuIC or RT-QuIC. The particles can be, for example, composed of a polymer coated with an antibody or another protein ligand, or can be particles formed of IO itself (without another substrate).

The particles can be of any size, such as diameter of the particles from approximately 1 mm to approximately 0.001 mm. The mean diameter of the population of particles may be from approximately 1 mm to approximately 0.1 mm. For example, the mean diameter of the particles may be 1 mm, 0.5 mm, or 0.01 mm. The population of particles may have a standard distribution of diameters of approximately plus or minus 10% from the mean diameter. In some embodiments, the diameter of the particles may be substantially homogeneous.

In some embodiments, the particles comprise iron oxide (IO), or another paramagnetic material, and the αSyn binds the particles. This can be used to isolate and concentrate the αSyn from the biological sample. The biological sample can be contacted with the particles, such as the IO particles, one, two, three or more times. The particles can be separated from the biological sample using a magnet or can be centrifuged or allowed to settle for separation. In some embodiments, about 10 μg to about 500 μg of particles, such as about 50 μg, about 60 μg, about 70 μg, about 80 μg, about 90 μg, about 100 μg, about 200 μg, about 300 μg, about 400 μg or about 500 μg of particles are contacted with the biological sample, such as about 100 μL to about 1,000 μL, or about 200 μL to about 200 μL of the biological sample, such as about 500 μL of the biological sample. Exemplary non-limiting concentrations are provided in the Examples section.

In further embodiments, the particles, such as the IO particles, can be washed prior to performing the amplification reaction. The particles, such as the IO particles, can be washed one, two, three or more times. In some embodiments, washing the iron oxide particles includes contacting the iron oxide particles with a buffered saline solution, such as phosphate buffered saline, Hepes buffered saline or Tris buffered saline, and collecting the iron oxide particles. In some embodiments, the buffered saline solution has a pH of about 7.2 to about 7.8, such as about 7.4 to about 7.6, such as about 7.5. In one non-limiting example, the buffered saline is phosphate buffered saline.

In some embodiments, the buffered saline solution further comprises a detergent. The detergent can be any detergent of interest, such as, but not limited to, sodium dodecyl sulfate (SDS). The detergent can be an anionic or a cationic detergent. In some non-limiting examples, the buffered saline solution comprises about 0.01 to about 1% SDS, such as about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9 or about 1.0% SDS. In a specific non-limiting example, about 0.05% SDS to about 0.1% SDS is included in the buffered saline solution, such as phosphate buffered saline.

In some embodiments, about 10 μg to about 500 μg of particles, such as about 50 μg, about 60 μg, about 70 μg, about 80 μg, about 90 μg, about 100 μg, about 200 μg, about 300 μg, about 400 μg or about 500 μg of particles are contacted with about 100 μL of the biological sample. The mixture may comprise approximately 10, 20, 30, 40 or 50 mg of particles per 100 μL of biological sample. For example, about 10 to about 50 mg of particles can be used per 100 μL of biological sample, from about 20 to about 50 mg of beads per 100 μL, or about 30 to about 50 mg of particles per 100 μL.

In some embodiments, the fraction is resuspended in a buffered saline solution, optionally including a detergent, prior to performing the assay. Suitable detergent and concentration are listed in the paragraphs above.

In some non-limiting examples, the sample is a cerebral spinal fluid sample and the fraction is resuspended in buffered saline. In other non-limiting examples, the sample is a human plasma sample, and the fraction is suspended in buffered saline including a detergent such as SDS, such as, but not limited to, phosphate buffered saline including 0.05% SDS or 0.01% SDS. In further non-limiting examples, the sample is a plasma sample, and the fraction is resuspended in buffered saline, such as PBS. The biological sample can be urine, feces, saliva, skin, whole blood, a blood fraction, cerebral spinal fluid, or a nasal brushing.

QuIC and RT-QuIC methods generally involve mixing a biological sample, or fraction thereof, that can include misfolded αSyn with a purified mutated rαSyn to make a reaction mix, and performing a primary reaction to form and amplify specific forms of αSyn protein the mixture, by using incubation conditions that promote coaggregation of the mutated rαSyn protein with the misfolded αSyn to result in a conversion of the mutated αSyn protein to mutated rαSyn aggregates. In these reactions, the development of spontaneously aggregated rαSyn is inhibited or delayed relative to reactions seeded with misfolded αSyn in a test sample.

Any of the substrates disclosed above can be used in the present methods. Without limitation, the substrate can be a mutated, truncated rαSyn protein that does not include amino acids 2-11. Thus, the mutated rαSyn protein can include amino acids 1 and 12-140 of an αSyn, with reference to wild-type human αSyn, for example see SEQ ID NO: 1. An exemplary amino acid sequence for this protein is provided as SEQ ID NO: 7. Thus the mutated rαSyn can include SEQ ID NO: 7 or SEQ ID NO: 8. The mutated rαSyn can consist of SEQ ID NO: 7 or SEQ ID NO: 8.

The substrate can be a mutated rαSyn that includes one or more point mutations, such as at residues K23, D2, K21, K45, T59, G67, V77, and/or A78. Suitable substrates are disclosed above. The substrate can include 1, 2, 3, 4, 5, 6, 7 or all 8 of these mutations. In some non-limiting examples, the mutated rαSyn includes only one mutation at K23, D2, K21, K45, T59, G67, V77, and/or A78. In specific non-limiting examples, the mutant rαSyn comprises one of SEQ ID NOs: 3, 5, 9, 11, 13, 15, 17, 19, 21 or 23, or a conservative variant thereof. In other specific non-limiting examples, the mutant rαSyn comprises, or consists of, one of SEQ ID NOs: 4, 6, 10, 12, 14, 16, 18, 20, 22 or 24, or a conservative variant thereof.

The mutated rαSyn can also be a deletion mutant, wherein amino acids 2-11 are deleted, and also can include 1, 2, 3, 4, 5, 6, or 7 mutations at positions K23, D2, K21, K45, T59, G67, V77, and/or A78 (with reference to the wild-type sequence, e.g., SEQ ID NO: 1). The mutation can be a substitution of K23, D2, K21, K45, T59, G67, V77, and/or A78 with any amino acid that is not the native amino acid. Optionally, the mutated rαSyn can include additional amino acids and the amino or carboxyl terminus.

In some embodiments additional substrate is added to the reaction mix. In other embodiments, additional substrate is not added to the reaction mix.

This primary reaction includes incubating the reaction mix to permit the misfolded αSyn aggregates present in the same, to initiate the conversion of mutated rαSyn to misfolded mutated rαSyn aggregates, fragmenting any aggregates formed during the incubation step; and repeating the incubation and fragmentation steps one or more times. In some embodiments, the primary reaction is repeated over 12, 24, 36, 48, 60, 72, 84, 96, 108, 120 hours or more. For example, the primary reaction can be repeated for about 12 to about 120 hours, such as 24 to 72 hours, or more. In other examples, the reaction can be performed for no more than about 12 hours or 24 hours, no more than 36 hours, no more than 48 hours, no more than 60 hours, no more than 72 hours, no more than 96 hours or no more than 120 hours. In several specific non-limiting examples, the reaction is performed for about 24 to about 48 hours. The reaction can be performed for 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours. In specific non-limiting examples, the sample is a brain tissue sample or a CSF sample.

In other embodiments, misfolded rαSyn aggregates can be detected at about 6 hours, 12 hours, 15 hours, 24 hours, 35 hours, 36 hours, or 48 hours. In other embodiments, misfolded rαSyn aggregates can be detected at about 6 to about 48 hours, such as about 12 to about 48 hours, such as about 24 to about 48 hours. In other embodiments, misfolded mutated rαSyn aggregates can be detected after 18-35 hours. In specific non-limiting examples, the sample is a CSF sample.

In some embodiments, the method is performed without serial amplification, such that substrate bound misfolded αSyn aggregates are retained in a reaction vessel, and that substrate is replenished without removing potential misfolded αSyn seeds. In other embodiments, serial amplification can be performed.

In further embodiments, misfolded αSyn aggregates can be amplified in a sample, by mixing the sample with purified mutated rαSyn n to make a reaction mix; performing an αSyn seeding assay that includes the steps of (i) contacting the biological sample or fraction thereof with a soluble mutated rαSyn to form a reaction mixture; ii) incubating the reaction mixture to permit coaggregation of misfolded αSyn aggregates present in the biological sample or fraction thereof with the mutated rαSyn; iii) maintaining incubation conditions that promote coaggregation of the mutated rαSyn with the misfolded αSyn aggregates to result in a conversion of the soluble mutated rαSyn to mutated rαSyn aggregates while inhibiting spontaneous aggregation of soluble mutant rαSyn; iv) agitating mutated rαSyn aggregates formed during step iii), wherein the conditions comprise shaking the reaction mixture in a shaking cycle, wherein each shaking cycle comprises a period of rest and a period of shaking; and b) detecting misfolded mutated rαSyn aggregates in the reaction mixture, and wherein detection of misfolded mutated rαSyn aggregates in the reaction mixture indicates that the subject has the synucleinopathy.

Detection of misfolded mutated rαSyn aggregates in the reaction mix indicates that misfolded αSyn was present in the sample. Additional mutated rαSyn can be added during the reaction, such as during the lag phase between the addition of the sample and the detection of mutated rαSyn aggregates formation. However, in some embodiments, a portion of the reaction mix is not removed and incubated with additional mutated rαSyn.

In some embodiments, the mutated rαSyn can be replenished at any time by adding additional mutated rαSyn to the reaction mix. In other embodiments, the mutated rαSyn is not replenished by adding additional mutated rαSyn to the reaction mix.

In some embodiments, the reaction includes the use of shaking in the absence of sonication. In other embodiments, the reaction uses shaking and sonication.

In either of these embodiments, the reaction can include cycles of shaking/rest that are 1:10 to 10:1 in duration, such as 1:5 to 5:1 in duration, for example, 1:2 to 2:1 in duration, or about 1:1 in duration.

The shaking cycle can be, for example, about 20 to about 180 seconds in length, such as about 30 to about 180 seconds in length, about 40 to about 180-seconds in length, about 50 to about 180 seconds in length, or about 60 to about 180 seconds in length. In some embodiments of these cycle times, the period of rest and the period of shaking are equal. In other embodiments of these cycle times, the period of rest and the period of shaking are unequal.

In some embodiments, the shaking and rest cycle are equal. In one non-limiting example, the reaction alternates 60 seconds of shaking and 60 seconds of no shaking (rest). In another non-limiting example, the reaction alternates 30 seconds of shaking and 30 seconds of no shaking (rest). However, the times can be varied, such as 45 seconds of shaking and 45 seconds of no shaking or 70 seconds of shaking and 70 seconds of no shaking.

In some embodiments, the period of rest and the period of shaking are about 120 seconds in length for the total cycle. In other embodiments, the total cycle time is about 60 to 180 seconds in length, such as, but not limited to 60, 70, 80, 90, 100, 110, 120, 130, 140, 150, 160, 170, or 180 seconds in length. In non-limiting examples, the period of shaking and rest in each cycle can be equal, as discussed above.

In other embodiments, the period of rest and the period of shaking are unequal. For example, the reaction includes 90 seconds of shaking and 30 seconds of no shaking, or 100 seconds of shaking and 20 seconds of no shaking, or 80 seconds of shaking and 40 seconds of rest. In additional embodiments, the total cycle time is about 60, 70, 80, 90, 100, 110 or 120 seconds in length and includes at least 30 seconds, at least 40, or at least 50, or at least 60 seconds of shaking. In specific non-limiting examples, the total cycle time is 60 to 180 seconds in length, such as, but not limited to 60, 70, 80, 90, 100, 110, 120, 130, 140, 150, 160, 170, or 180 seconds in length.

Reactions can be performed at 30-55° C., for example 35-50° C., such as 37-42° C., such as about 37° C., 42° C., or at about 42° C. to 55° C., such as 42° C. to about 50° C.

In some embodiments, the reaction is performed using sodium chloride (NaCl) at a concentration of about 50 mM to about 500 mM, such as about 100 to about 700, or about 100 mM to about 500 mM NaCl. In additional embodiments, about 100 mM, 200 mM, 300 mM, 400 mM NaCl. In other embodiments, the reaction is performed using 200 to 400 mM NaCl, such as using 170 mM NaCl. In some embodiments, the reaction does not include an added detergent, such as an anionic, cationic, and/or zwitterionic detergent. In some examples, the reaction does not include any added detergent. In further embodiments, the reaction does not include added anionic detergent, such as, but not limited to, sodium dodecyl sulfate (SDS).

In other embodiments, the reaction includes an anionic detergent, such as SDS. In some embodiments, anionic detergent at a concentration up to about 0.1% is included in the reaction. The anionic detergent concentration, such as the SDS concentration, can be, for example, about 0.0001% to about 0.005%. The anionic detergent concentration can be, for example, less than 0.005%. The detergent concentration can be, for example, about 0.0001%, 0.0002%, 0.0003%, 0.0004%, 0.0005%, 0.0006%, 0.0007%, 0.0008%, 0.0009% of an anionic detergent, such as, but not limited to, SDS. In other embodiments, the detergent concentration can be, for example, about 0.001%, 0.002%, 0.003%, 0.004%, 0.005%, 0,006%, 0.007%, 0.008%, 0.009%, 0.01%, 0.02%, 0.03%, 0.04%, 0.05%, 0.06%, 0.07%, 0.08%, 0.09% or 0.1% of an anionic detergent, such as, but not limited to, SDS.

A solid substrate, such as a bead, such as beads can be used in the reaction. The beads can be any solid substrate, and include, but are not limited to, glass, polystyrene, silica, silica/zirconia, or metal beads. In some specific non-limiting examples, glass beads are utilized.

The beads can be spherical and have a diameter of about 0.5 mm to about 3 mm in diameter, such as about 0.5 to about 2 mm in diameter, such as about 1 to about 2 mm in diameter. In some non-limiting examples, the beads have a diameter of about 1 mm.

The beads can be included in a reaction at a concentration of 1 to 10 beads per 100 microliters (µl), such as 2 to 8 beads per 100 µl, such as 4 to 6 beads per 100 µl. In some embodiments, the reaction includes 1, 2, 3, 4, 5, 6, 7, 8, 9, or 10 beads per 100 µl. In some non-limiting examples, the beads are glass.

In an RT-QuIC assay, a reaction product, such as misfolded rαSyn aggregates, is detected in real time (RT). There is generally a lag phase in a QuIC reaction, wherein amyloid cannot be detected. The lag phase is considered to end when a statistically significant amount of amyloid can be detected, as compared to the background level of fluorescence. The present methods result in a short lag time. In some embodiments, the misfolded rαSyn aggregates can be detected, using fluorescence, at about 6 hours, 12 hours, 24 hours, 36 hours, 48 hours, 60 hours, 72 hours, 84 hours or 90 hours. In additions embodiments, misfolded rαSyn aggregates can be detected at about 6 to about 24 hours, such as about 12 to about 24 hours, such as about 18 to about 24 hours. In other embodiments, misfolded rαSyn aggregates can be detected at about 6 to about 48 hours, such as about 12 to about 48 hours, such as about 24 to about 48 hours. In further embodiments, misfolded rαSyn aggregates can be detected at about 6 to about 72 hours, such as about 12 to about 72 hours, such as about 24 to about 72 hours, such as about 48 to 72 hours or 60 to 72 hours. In further embodiments, misfolded rαSyn aggregates can be detected at about 6 to about 90 hours, such as about 12 to about 90 hours, such as about 24 to about 90 hours, 48 to 90 hours, 60 to 90 hours or 72 to 90 hours. In specific non-limiting examples, the sample is a CSF sample.

Thus, QuIC reaction can be an RT-QuIC reaction, and thus can include an amyloid-sensing dye, such as thioflavin T (ThT) or thioflavin S (ThS), or any other substrate which allows detection of the amyloid. Exemplary dyes include P-FTAA (quadro-formylthiophene acetic acid), HS-68, HS-67, HS-72, P-HTAA, P-HTAA-Se, P-FTAA-Se, and HS-53. The structure of these dyes is shown in Klingstedt et al., *Chemistry* 2013 Jul. 29; 19(31):10179-92. doi: 10.1002/chem.201301463, Epub 2013 Jun. 18, which is incorporated herein by reference.

The RT-QuIC assay incorporates mutated rαSyn as a substrate, intermittent shaking of the reactions such as in multi-well plates, largely detergent- and chaotrope-free reaction conditions and, in some embodiments, ThT- or ThS-based fluorescence detection of any resulting amyloid protein generated by the reaction. One advantage of using ThT (or ThS) is that it can be included in the reaction mixture. However, any of the dyes disclosed above can also be utilized.

In some embodiments, ThT is utilized. Thioflavin T is a benzothiazole dye that exhibits enhanced fluorescence upon binding to amyloid fibrils (see Khurana et al., J. Structural Biol. 151: 229-238, 2005), and is commonly used to detect amyloid fibrils.

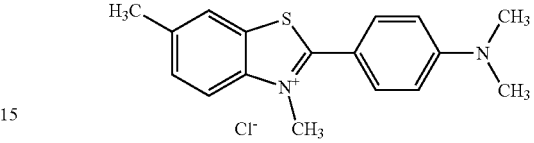

Following amplification, the misfolded rαSyn aggregates in the reaction mix is detected. If ThT is included in the reaction (RT-QuIC), then can be detected using fluorescence at 450+/−10 nm excitation and 480+/−10 nm emission (see for example, Wilham et al., PLOS Pathogens 6(12): 1-15, 2010, incorporated herein by reference.) ThT can be included directly in the amplification mixture. In some embodiments, if ThT is included, the reaction mix does not include high concentrations of chaotropes or detergents.

In one non-limiting example, in RT-QuIC reactions the final concentration of ThT in each reaction is 1 mM. In other examples, ThT is used at a final concentration of about 0.001 to 10 mM in the reaction.

Other dyes can be used in place of ThT, such as Thioflavin S, Congo red and Congo red-derived fluorescent probe (trans, trans),-1-bromo-2,5-bis-(3-hydroxycarbonyl-4-hydroxy)styrylbenzene (BSB). One of skill in the art can readily utilize these dyes.

The fluorescence emitted by ThT (or ThS) can be measured in real time (RT). There is usually a lag phase in a RT-QuIC reaction, wherein ThT fluorescence cannot be detected. At some point, a statistically significant amount of fluorescence can be measured that is above background fluorescence. The time of initiation of the reaction to the time of appearance of a statistically significant amount of detectable fluorescence, which represents the presence of misfolded rαSyn aggregates, can be measured as the lag phase. The length of the lag phase can vary when different substrates are used. In some embodiments, the use of the mutated rαSyn substrates, disclosed above, shortens the lag time for the presently disclosed reactions, thus allowing misfolded rαSyn aggregates to be detected quickly.

If standard QuIC is utilized, misfolded rαSyn aggregates can be detected by means other than ThT fluorescence, for example, using an antibody (see below).

Two types of misfolded αSyn protein can be generated in QuIC reactions, one arising spontaneously without seeding and the other initiated by the presence of misfolded αSyn in the test sample. An unexpectedly superior decrease in the speed and amount of spontaneously arising rαSyn aggregates formed is achieved with the QuIC assays disclosed herein. Thus, the RT-QuIC (which includes thioflavin T) reactions disclosed herein provides sensitive and specific detection of misfolded αSyn, and allows diagnosis of synucleinopathies.

V. Methods for Detecting In the Absence of a Dye

Once aggregates have been generated, the aggregates can be detected in the reaction mixture. Direct and indirect methods can be used for detection of aggregates in a reaction mixture. Detection using a fluorescent dye is described above. However, other methods can be utilized.

A. Western Blot

In some examples, reaction mixtures are then subjected to Western blot for detection of aggregates. Typical Western blot procedures begin with fractionating proteins by sodium dodecyl sulfate-polyacrylamide gel electrophoresis (SDS-PAGE) under reducing conditions. The proteins are then electroblotted onto a membrane, such as nitrocellulose or PVDF and probed, under conditions effective to allow immune complex (antigen/antibody) formation, with an anti-αSyn antibody. Exemplary antibodies for detection of αSyn include Purified Mouse Anti-αSyn Clone 42/α-Synuclein (BD Transduction Laboratories).

Following complex formation, the membrane is washed to remove non-complexed material. An exemplary washing procedure includes washing with a solution such as PBS/Tween, or borate buffer. The immunoreactive bands are visualized by a variety of assays known to those in the art. For example, the enhanced chemiluminescence assay (Amersham, Piscataway, N.J.) can be used.

If desired, αSyn concentration can be estimated by Western blot followed by densitometric analysis, and comparison to Western blots of samples for which the concentration of αSyn is known. For example, this can be accomplished by scanning data into a computer followed by analysis with quantitation software. To obtain a reliable and robust quantification, several different dilutions of the sample generally are analyzed in the same gel.

B. ELISA, Immunochromatographic Strip Assay, and Conformation Dependent Immunoassay As described above, immunoassays in their most simple and direct sense are binding assays. Specific non-limiting immunoassays of use include various types of enzyme linked immunosorbent assays (ELISAs), immunochromatographic strip assays, radioimmunoassays (RIA), and specifically conformation-dependent immunoassays.

In one exemplary ELISA, anti-αSyn antibodies are immobilized onto a selected surface exhibiting protein affinity, such as a well in a polystyrene microtiter plate. Then, a reaction mixture suspected of containing αSyn is added to the wells. After binding and washing to remove non-specifically bound immune complexes, the bound αSyn can be detected. Detection generally is achieved by the addition of another anti-αSyn antibody that is linked to a detectable label. This type of ELISA is a simple "sandwich ELISA." Detection also can be achieved by the addition of a second anti-αSyn antibody, followed by the addition of a third antibody that has binding affinity for the second antibody, with the third antibody being linked to a detectable label.

In another exemplary ELISA, the reaction mixture suspected of containing the αSyn is immobilized onto the well surface and then contacted with the anti-αSyn antibodies. After binding and washing to remove non-specifically bound immune complexes, the bound anti-αSyn antibodies are detected. Where the initial anti-αSyn antibodies are linked to a detectable label, the immune complexes can be detected directly. Again, the immune complexes can be detected using a second antibody that has binding affinity for the first anti-αSyn antibody, with the second antibody being linked to a detectable label.

Another ELISA in which protein of the reaction mixture is immobilized involves the use of antibody competition in the detection. In this ELISA, labeled antibodies against αSyn are added to the wells, allowed to bind, and detected by means of their label. The amount of αSyn protein in a given reaction mixture is then determined by mixing it with the labeled antibodies against αSyn before or during incubation with coated wells. The presence of αSyn in the sample acts to reduce the amount of antibody against αSyn available for binding to the well and thus reduces the ultimate signal. Thus, the aggregates of rαSyn in the sample can be quantified.

Irrespective of the format employed, ELISAs have certain features in common, such as coating, incubating or binding, washing to remove non-specifically bound species, and detecting the bound immune complexes. These are described below.

In coating a plate with either antigen or antibody, one generally incubates the wells of the plate with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antibodies. These include bovine serum albumin, casein, and solutions of milk powder. The coating allows for blocking of nonspecific adsorption sites on the immobilizing surface, and thus reduces the background caused by non-specific binding of antibodies onto the surface.

It is customary to use a secondary or tertiary detection means rather than a direct procedure with ELISAs, though this is not always the case. Thus, after binding of a protein or antibody to the well, coating with a non-reactive material to reduce background, and washing to remove unbound material, the immobilizing surface is contacted with the biological sample or fraction thereof to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin, milk proteins, and phosphate buffered saline (PBS)/Tween. These added agents also tend to assist in the reduction of nonspecific background. "Suitable" conditions also mean that the incubation is at a temperature and for a period of time sufficient to allow effective binding. Incubation steps are typically from about 1 to 2 to 4 hours, at temperatures preferably on the order of 25° C. to 27° C., or can be overnight at about 4° C. or so.

Following all incubation steps in an ELISA, the contacted surface is washed so as to remove non-complexed material. An exemplary washing procedure includes washing with a solution such as PBS/Tween or borate buffer. Following the formation of specific immune complexes between the test sample and the originally bound material, and subsequent washing, the occurrence of even minute amounts of immune complexes can be determined.

To provide a detecting means, the second or third antibody generally will have an associated label to allow detection. In some examples, this is an enzyme that will generate color development upon incubating with an appropriate chromogenic substrate. Thus, for example, the first or second immune complex is contacted and incubated with a urease, glucose oxidase, alkaline phosphatase or hydrogen peroxidase-conjugated antibody for a period of time and under conditions that favor the development of further immune complex formation (for instance, incubation for two hours at room temperature in a PBS-containing solution such as PBS-Tween).

After incubation with the labeled antibody, and subsequent to washing to remove unbound material, the amount of label is quantified, for instance, by incubation with a chromogenic substrate such as urea and bromocresol purple or 2,2'-azino-di-(3-ethyl-benzthiazoline-6-sulfonic acid) and $H_2O_2$, in the case of peroxidase as the enzyme label. Quantification is then achieved by measuring the degree of color generation, for instance, using a visible spectra spectrophotometer.

C. Recombinant αSyn Protein Labeling

In certain embodiments, the mutated rαSyn protein can be labeled to enable high sensitivity of detection of protein that is converted into aggregates. For example, the mutated rαSyn can be radioactively labeled, epitope tagged, or fluorescently labeled. The label can be detected directly or indirectly. Radioactive labels include, but are not limited to $^{125}I$, $^{32}P$, $^{33}P$, and $^{35}S$.

The mixture containing the labeled protein is subjected to a αSyn seeding assay, such as QuIC, and the product detected with high sensitivity by following conversion of the labeled protein to aggregates, and after removal of the unconverted protein. Alternatively, the protein can be labeled in such a way that a signal can be detected upon the conformational changes induced during conversion. An example of this is the use of FRET technology, in which the protein is labeled by two appropriate fluorophores, which upon refolding become close enough to exchange fluorescence energy (see for example U.S. Pat. No. 6,855,503).

In certain other embodiments, the use of a fluorescently-tagged substrate for the reaction is combined with the use an immunochromatographic strip test with an immobilized αSyn specific antibody. Binding of the rαSyn to the antibody is then detected with a fluorescence detector.

D. Protease Treatment

Misfolded αSyn and rαSyn can also be are separated by protease treatment. In some embodiments, the total protein concentration in the reaction is measured, such as using Coomassie blue. The reaction mixtures are incubated with, for example, Proteinase K (PK). An exemplary protease treatment includes digestion of the protein in the reaction mixture with 1-20 µg/ml of PK for about 1 hour at 37° C. Reactions with PK can be stopped prior to assessment of prion levels by addition of PMSF or electrophoresis sample buffer. Depending on the nature of the sample, incubation at 37° C. with 1-50 µg/ml of PK generally is sufficient to remove rαSyn. The amount of protein remaining in the sample can then be measured.

rPrP-res$^{(Sc)}$ also can be separated from the rPrP$^{Sen}$ by the use of ligands that specifically bind and precipitate the misfolded form of the protein, including conformational antibodies, certain nucleic acids, plasminogen, PTA and/or various peptide fragments.

EXAMPLES

Assays called Real-Time Quaking Induced Conversion (RT-QuIC) have provided ultrasensitive, specific and quantitative diagnostic tests for prion diseases (Wilham et al., 2010, PLoS Path 6:e1001217; Atarashi et al., 2011, Nat Med 17:175-178). RT-QuIC assays are multi-well plate-based reactions that can rapidly amplify oligomeric/multimeric prion seeds by as much as a trillion-fold (Wilham et al., 2010, PLoS Path 6:e1001217; Orru et al., 2011, mBio 2:e00078-11; Foutz et al., 2017, Ann Neurol 81:79-92). Prion RT-QuIC assays have been applied successfully to a variety of biological samples including brain (Wilham et al., 2010, PLoS Path 6:e1001217; Peden et al., 2012, J Gen Virol 93:438-44), cerebrospinal fluid (CSF) (Orru et al., 2015, J Gen Virol 93:438-44; McGuire et al., 2012, Ann Neurol 72:278-285; Cramm et al., 2015, Mol Neurobiol 51:396-405; Sano et al., 2013, PLoS One 8:e54915), whole blood and plasma (Orru et al., 2011, mBio 2:e00078-11; Vascellari et al., 2012, PLoS One 7:e48969), urine (John et al., 2013, Prion 7:253-8), and nasal brushings (Orru et al., 2014; New Engl J Med 371:519-529; Zannusso et al., 2014, N Engl J Med 371:1842-3) and are being widely implemented for the diagnosis of prion diseases in humans and animals. Notably, recent studies demonstrated 100% diagnostic sensitivity and specificity in diagnosing human sporadic Creutzfeldt-Jakob disease using CSF and/or nasal swabs (Bongianni et al., 2017, JAMA Neurology 74:1-8). A need remains for adapting these methods for other proteins, such as αSyn.

An RT-QuIC approach for synucleinopathies was developed and applied to total of 137 PD and DLB cases and controls (Fairfoul et al., 2016, Ann Clin Transl Neurol 3:812-818). This αSyn RT-QuIC gave 95% and 92% sensitivity for PD and DLB patients, respectively, with 100% specificity. Another assay, an αSyn protein misfolding cyclic amplification (αSyn PMCA), provided 89% sensitivity for PD and 97% specificity in analyses of 173 total cases and controls (Shahnawaz et al., 2017, JAMA Neurol 74:163-172). In both of these assays, small volumes of CSF are added to reactions containing excesses of recombinant wild-type αSyn. Any αSyn seeds in the sample initiates fibril formation by the recombinant αSyn which, in turn, enhances the fluorescence of thioflavin T. However, these reactions are slow, and must be performed over 5 to ~13 days.

It is disclosed herein that using a mutant rαSyn substrate, a more rapid αSyn RT-QuIC assay was developed, wherein misfolded αSyn present in a sample was quickly detected. Thus, the assay can be completed within 2 days with excellent diagnostic sensitivity and specificity.

Example 1

Materials and Methods

Alpha-synuclein osmotic shock protein purification protocol: Five ml of media were inoculated from a glycerol stock of *E. coli* bacteria containing the vector for K23Q αSyn protein expression. Following a 4-5-hour incubation with continuous 225 rpm agitation at 3TC, 1 L of the auto-induction media was prepared and the 5 mL starter culture was added. The cells were grown in a shaking incubator at 37° C., 225 rpm, overnight. The next day cells were harvested by splitting the 1 L culture into 4 250 ml conical tubes and centrifuging at 3273×g, 4° C., 10 min.

Next, the cell pellets were resuspended in 10% volume of room temperature osmotic shock buffer, (25 mL per 250 mL of cell culture before centrifugation) and incubated at room temperature for 10 min. This was resuspended gently with a 25 mL serological pipette. Next the suspension was centrifuged at 9000×g, 20° C., 20 min. The supernatant was discarded and the pellet was resuspended gently in ice-cold water, using 10 mL of water per pellet. This step was done very gently using a 25 mL serological pipette. The samples were pooled into two tubes of 20 ml and 20 µL of saturated $MgCl_2$ were added per 20 mL of cell suspension. The solution was then mixed and incubated on ice with mild rocking for 3 min. Next, the suspension was centrifuged at 9000×g, 4° C., 30 min. The supernatant was collected in a 100 ml glass beaker that contained a stir bar for continuous mixing. The pH was changed using 800-900 uL of a 1 M HCl solution to pH 3.5. The HCl was added in boluses, while monitoring the pH carefully to adjust appropriately.

This generated a large amount of white precipitate. The suspension was then incubated with gentle stirring at room temperature for 10 min. The formation of air bubbles was avoided during this step. Next the samples were centrifuged at 9000×g, 4° C., 30 min, and the supernatant was collected in a 100 ml beaker with a stir bar for continuous agitation. This step was followed by the addition of 800-900 uL of 1 M NaOH to change to pH to 7.5. As described previously, a bolus of NaOH was added with systematic monitoring of the pH to adjust appropriately.

The protein extract was then filtered through a pore size filter of 0.45 µm, or lower. At this stage, the extract could be stored at 4° C. for an hour or so if needed. Next, the extract was loaded onto a 5 ml Ni-NTA column and washed with Buffer A (20 mM Tris, pH 7.5). The column was further washed with 10% buffer B1 (20 mM Tris, 500 mM imidazole, pH 7.5) which generated a peak that was not collected. Next, a peak was collected between 30 and 75% Buffer B1. This peak was then loaded onto a Q-HP column and washed with Buffer A. The column was further washed with 10% buffer B1 (20 mM Tris, 500 mM imidazole, pH 7.5). A peak was recovered between 30 and 45% Buffer B2 (20 mM Tris, 1000 mM NaCl, pH 7.5) and filtered through 0.22 µm filter.

The protein was then dialyzed against water overnight at 4° C. using a 3 kDa MWCO dialysis membrane. The next day, the protein was moved into fresh water for another 4 h dialysis.

The protein concentration was determined with a UV-VIS spectrophotometer using a theoretical extinction coefficient at 280 nm of 0.36 $(mg/mL)^{-1}cm^{-1}$. The obtained protein was lyophilized in aliquots and stored it for a final concentration of ~1.0 mg/ml once resuspended in 500 µL of 40 mM phosphate buffer (pH 8.0). These aliquots were stored at −80° C. until further analysis.

Brain homogenate preparations: Brain homogenates (BH; 10% w/v) were prepared by homogenizing the tissue in PBS using a Bead beater (1 min at maximum speed). The homogenate was then spun at 2000×g for 2 min at room temperature and the supernatant was transferred to a new tube and stored at −80° C. for αSyn RT-QuIC analysis. For αSyn RT-QuIC testing, BHs were serially diluted in PBS.

RT-QuIC protocol: RT-QuIC reactions were performed in a black 96-well plate with a clear bottom (Nunc) preloaded with 6 glass beads (1 mm in diameter; BioSpec Products) per well. For brain homogenate seeded reactions, the reaction mix was composed of 40 mM phosphate buffer (pH 8.0), 170 mM NaCl, 0.1 mg/ml rαSyn, 10 µM thioflavin T (ThT). Aliquots of the reaction mix (98 µL) were loaded into each well of the 96-well plate and seeded with 2 µL of indicated BH dilutions. The plate was then sealed with a plate sealer film (Nalgene Nunc International) and incubated at 42° C. in a BMG FLUOstar Omega plate reader with cycles of 1 min shaking (400 rpm double orbital) and 1 min rest throughout the indicated incubation time. ThT fluorescence measurements (450+/−10 nm excitation and 480+/−10 nm emission; bottom read) were taken every 45 min.

In the case of CSF seeded reactions a plate pre-loaded with 6 glass beads per well was loaded with a reaction mix containing 40 mM phosphate buffer (pH 8.0), 170 mM NaCl, 0.1 mg/ml rαSyn, 10 µM thioflavin T (ThT) and 0.0015% sodium dodecyl sulfate (SDS) detergent (in a final 100 µL reaction volume). In this case aliquots of the reaction mix (85 µL) were loaded into each well of the 96-well plate and seeded with 15 µL of CSF or CSF dilutions.

Reactions were classified as RT-QuIC positive based on criteria similar to those previously described for RT-QuIC analyses of brain specimens (Wilham 2010, PLoS Pathog; Orru 2014; NEJM).

Example 2

Sodium Dodecyl Sulfate (SDS) Titration in CSF Seeded αSyn RT-QuIC

The results presented in FIG. 1 shows a much faster and stronger fluorescence signal when SDS is added to the reaction mix. As the concentration of SDS decreases, so does the speed of detection. Of note is the spontaneous conversion of the substrate we observed when using 0.002% SDS (gray circles at ~69 hours) in the CBD seeded CSF reactions. This suggest that a concentration of SDS lower than 0.002% should be used.

Example 3

Sodium Dodecyl Sulfate (SDS) and CSF Titration in αSyn RT-QuIC

Figures 2A, 2B:
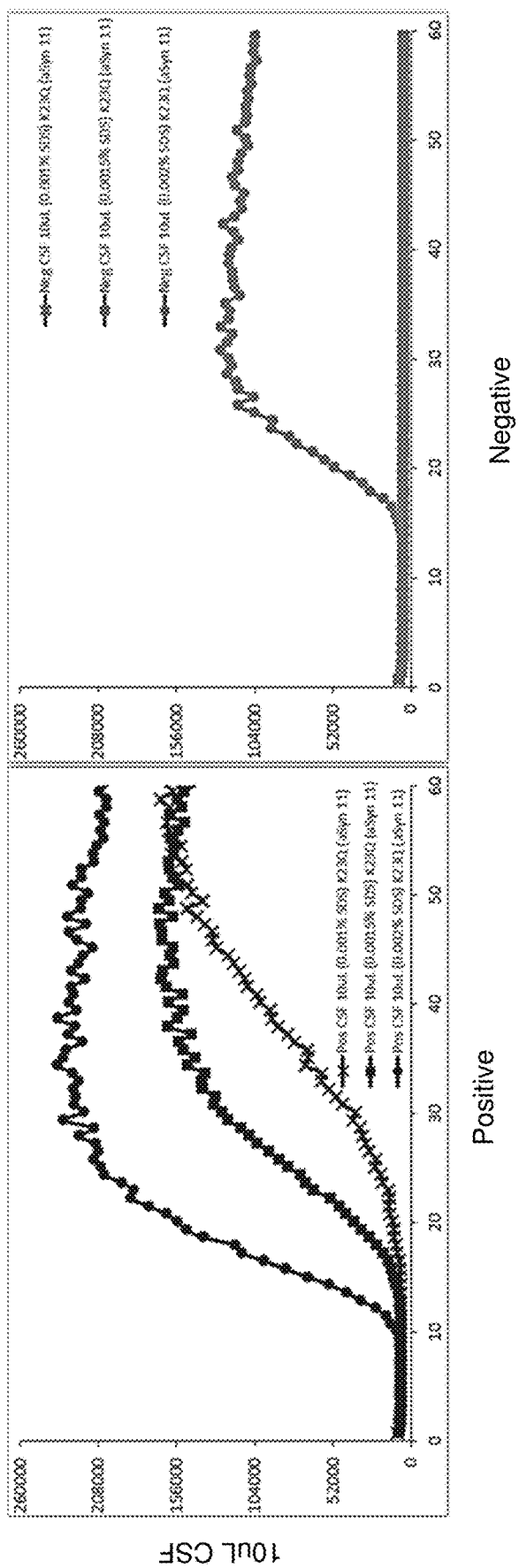
Figure 5:
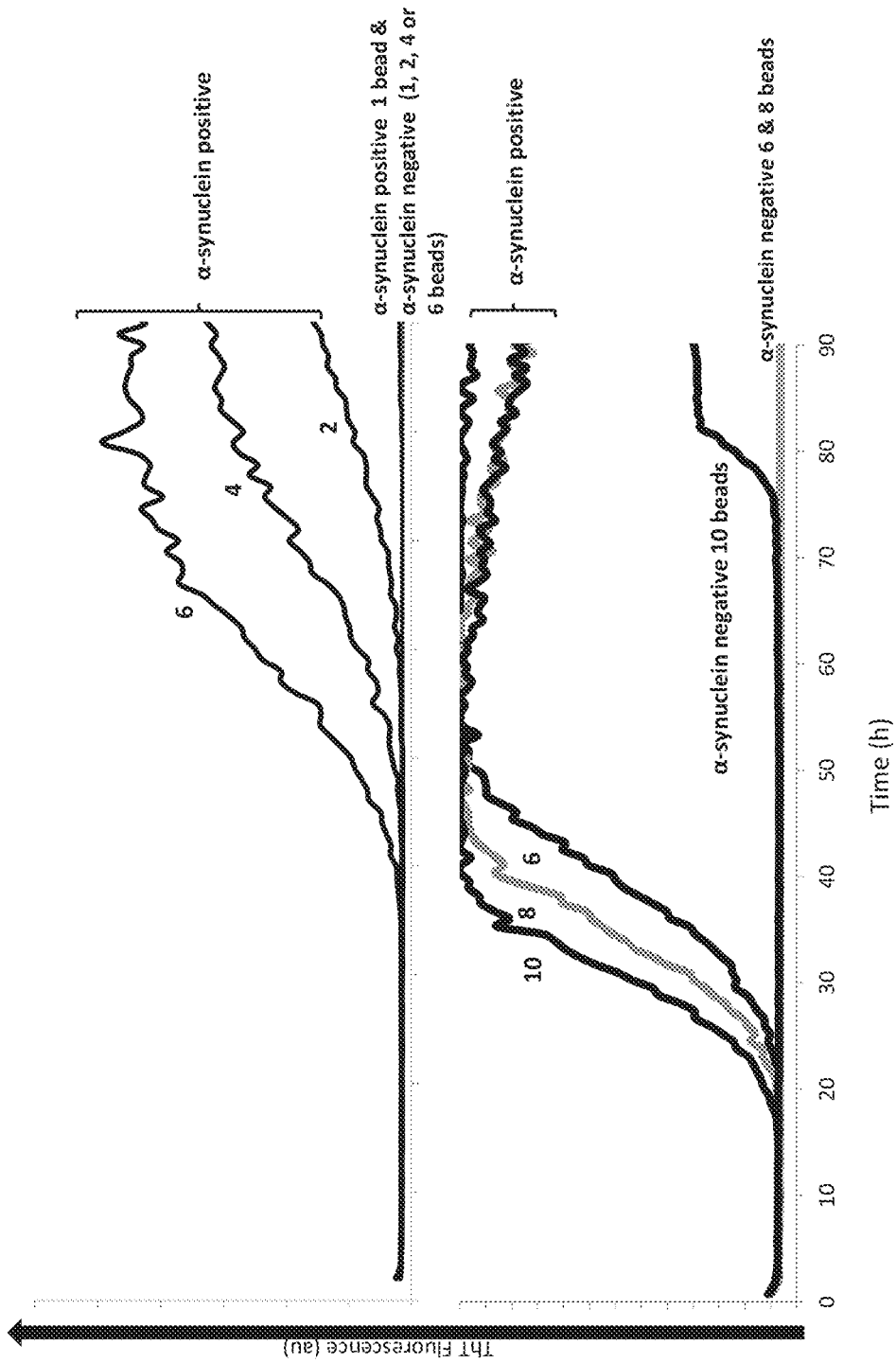
FIG. 5. αSyn RT-QuIC glass bead titration αSyn RT-QuIC reactions using the K23Q rαSyn substrate were seeded with a $10^{-3}$ dilution of either non-synucleinopathy (CBD) or synucleinopathy (PD) brain samples and incubated at 42° C. with one-minute double orbital shaking at 400 rpm and one-minute rest, for 90 hours. Quadruplicate wells were set up with either 1, 4, 6, 8 or 10 glass beads (1 mm diameter) per well as indicated and the average ThT fluorescence from those quadruplicates is shown in two overlapping experiments in the upper and lower panels. In each experiment, faster responses from the PD-seeded reactions were observed from those containing more beads. However, the bottom panel indicates that with 10 beads per well, false-positive reactions seeded with the CBD brain can begin to occur at ~75 h.

The results presented in FIG. 2 show that when using 10 µL of CSF per reaction in combination with 0.002% SDS some spontaneous conversion of the substrate in non-synucleinopathy (corticobasal degeneration) CSF-seeded reactions occurred. This was not observed when the same volume of CSF was used in combination with 0.0015% SDS (FIG. 2B). In FIG. 2C, where reactions were seeded with 15 µl of CSF, rapid detection of αSyn seeding activity was observed in Parkinson CSF-seeded reactions and no spontaneous conversion of the substrate (FIG. 2D) was observed in negative CSF seeded reactions. In FIG. 2E, where reactions were seeded with 20 µl of CSF, samples showed weaker and slower fluorescence signals (average of all replicate wells) with spontaneous conversion of the substrate in CBD CSF seeded reaction with 0.002 and 0.0015% SDS in the reaction mix. These results suggest that there was only modest gain of speed of detection or fluorescence signal intensity using the larger volume of CSF (20 µL per well) compared to 10 or 15 µL per reaction. Furthermore, the combination of 20 µL of CSF with 0.002 or 0.0015% SDS, still showed evidence of spontaneous conversion of the substrate in CBD-seeded control reactions (FIG. 2F). Therefore, 15 µL of CSF per well was used in combination with 0.0015% SDS. These conditions allow for fast discrimination between synucleinopathy-positive and -negative samples and did not lead to spontaneous conversion of the substrate in the absence of synucleinopathy sample.

Example 4

Blinded Testing of CSF Samples by αSyn RT-QuIC

These results shown in FIG. 3 document specific and rapid detection of αSyn seeding activity in CSF samples from PD and DLB patients. The findings also show lack of detection of seeding activity in samples from AD and non-synucleinopathy patients.

Example 5

Comparison the Performance of Wild Type and K23Q αSyn Recombinant Protein in the αSyn RT-QuIC A wild type αSyn recombinant protein or a protein containing the K23Q amino acid substitution was used as the rαSyn substrate for the reactions. As shown in FIG. 4, the results show that, using the present methods, the K23Q mutant substrate supports much faster amplification of αSyn seeding activity, with detection down to $10^{-5}$ BH dilution within 30 hours (FIG. 4A). The wild type substrate, detects down to $10^{-5}$ BH with much slower kinetics within 50 hours (FIG. 4C).

A similar phenomenon was observed with CSF-seeded reactions, with significantly faster amplification (~20 hours) of αSyn seeding activity observed when using the K23Q mutant substrate (FIG. 4B) rather than the wild type substrate which supported much slower amplification kinetics of ~40 hours. (FIG. 4D). Overall, faster detection of seeding activity was achieved using the K23Q mutant protein as the substrate compared to the WT substrate.

Example 6

Glass Beads

Figure 6:
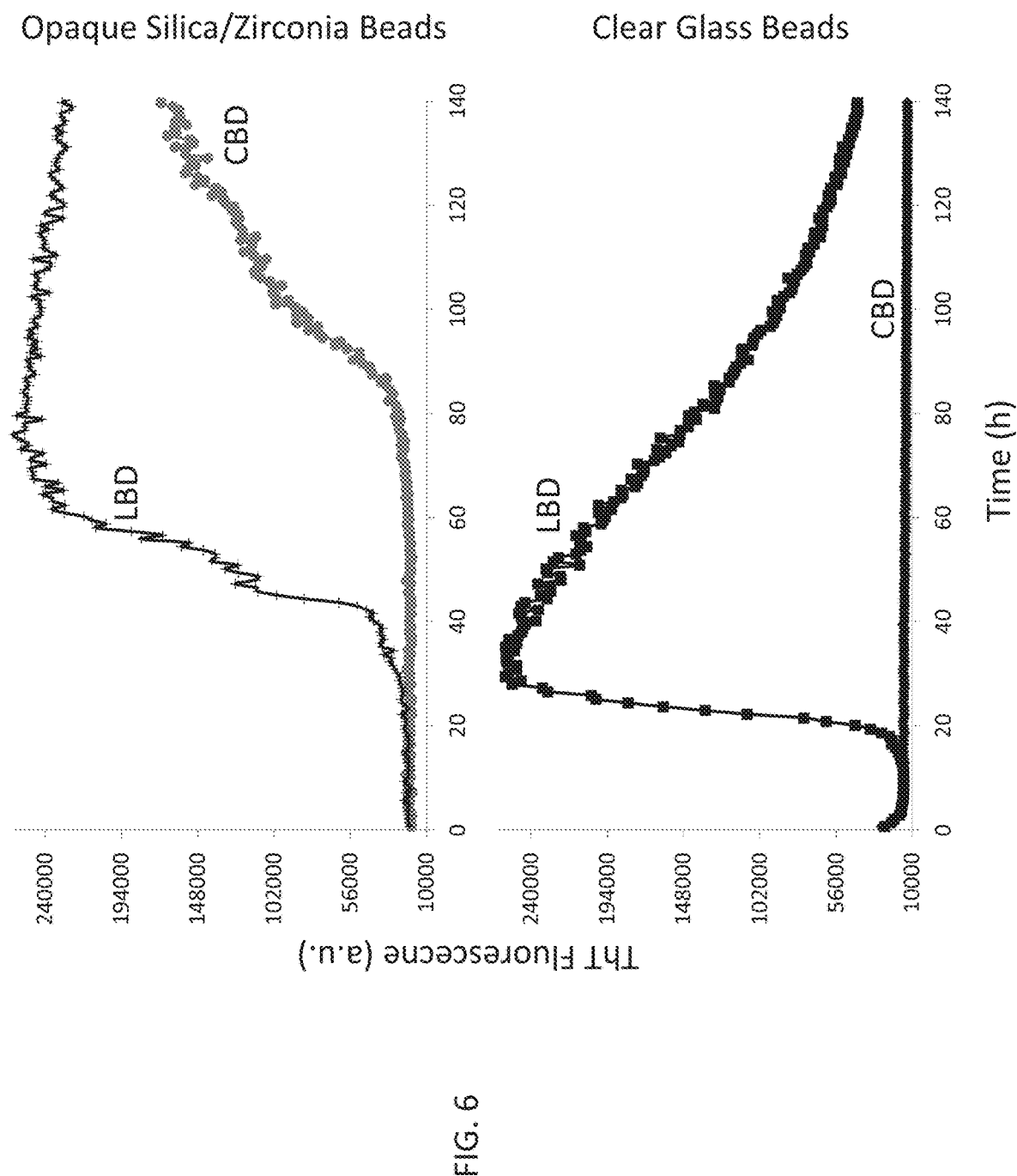
FIG. 6. Bead material comparison. 1.0 mm Opaque silica/zirconia beads (top) or clear glass beads (bottom) were added to reactions seeded with $10^{-2}$ dilutions of Lewy body enriched samples derived from brain homogenates containing synucleinopathy (DLB) or without synucleinopathy (CBD). Reactions were performed in quadruplicate and the average fluorescence from the 4 wells is shown. The results indicate that faster responses were obtained with the clear glass beads, and that negative control CBD reactions containing the silica/zirconia beads began to become falsely positive earlier, i.e., after about 80 h.

Each sample trace represents the average ThT signal of quadruplicate wells. The results show that increasing the number of beads in the reaction decreases the time of amplification, with reactions containing 10 beads being the fastest. However, these same reactions also show evidence of spontaneous conversion of the substrate in synucleinopathy-negative control reactions. Six beads per well was selected for use. Additional results are shown in FIG. 6. The reaction containing the opaque beads was slower, noisier, and triggered spontaneous aggregation earlier than the clear glass beads.

Example 7

Analysis of Blood Plasma Samples by αSyn RT-QuIC

Blood plasma samples, or dilutions thereof, are used as test specimens in αSyn RT-QuIC reactions using the present methods. In some cases, the plasma dilutions are added directly to the αSyn RT-QuIC reactions. In other cases, synucleinopathy-associated αSyn seeds in the plasma samples are first captured by binding to beads or other particles coated with antibodies or other ligands that bind to αSyn seeds, and then rinsed prior to being added to the αSyn RT-QuIC reactions. In other cases, synucleinopathy-associated αSyn seeds in the plasma samples are first concentrated, for example by phosphotungstate anion (PTA) precipitation or exosome isolation, and then processed prior to being added to the αSyn RT-QuIC reactions. Plasma samples from synucleinopathy patients, concentrates, or beads that are incubated with the synucleinopathy plasma samples, cause more rapid increase in ThT fluorescence in the reactions than analogous samples from non-synucleinopathy cases, allowing discrimination between synucleinopathy and non-synucleinopathy patients.

Example 8

Analysis of Blood Buffy Coat Samples by αSyn RT-QuIC

Buffy coat cell fractions from blood samples, or dilutions thereof, are treated to disrupt cellular membranes, for example with freeze-thaw cycles, sonication, bead beaters, nuclease, protease and/or lipase treatments, and added to αSyn RT-QuIC reactions. When protease treatments are used, protease inhibitors are added prior to performing the αSyn RT-QuIC. In some cases, the disrupted buffy coat cell preparations are added directly to the αSyn RT-QuIC reactions. In other cases, synucleinopathy-associated αSyn seeds in the disrupted buffy coat preparations are first captured by binding to beads or other particles coated with antibodies or other ligands that bind to synucleinopathy-associated αSyn seeds. The beads are then rinsed prior to being added to αSyn RT-QuIC reactions. In other cases, synucleinopathy-associated αSyn seeds in the buffy coat samples are first concentrated, for example by phosphotungstate anion (PTA) precipitation or exosome isolation, processed, then added to the αSyn RT-QuIC reactions. Buffy coat, concentrates or buffy coat-treated bead samples from synucleinopathy patients cause more rapid increase in ThT fluorescence in the reactions than samples from non-synucleinopathy cases, allowing discrimination between synucleinopathy and non-synucleinopathy patients.

Example 9

Analysis of Whole Blood Samples by αSyn RT-QuIC

Anti-coagulant-treated whole blood samples, or dilutions thereof, are treated to disrupt cellular membranes, for example with freeze-thaw cycles, sonication, bead beaters, nuclease, protease and/or lipase treatments, and added to αSyn RT-QuIC reactions. When protease treatments are used, the protease inhibitors are added prior to performing the αSyn RT-QuIC reaction. In some cases, the disrupted whole blood preparations are added directly to the αSyn RT-QuIC reactions. In other cases, synucleinopathy-associated αSyn seeds in the disrupted whole blood samples are first captured by binding to beads or other particles coated with antibodies or other reagents that bind to synucleinopathy-associated αSyn seeds. The beads are then rinsed prior to being added to αSyn RT-QuIC reactions. In other cases, synucleinopathy-associated αSyn seeds in the whole blood samples are first concentrated, for example by phosphotungstate anion (PTA) precipitation or exosome isolation, and then processed prior to being added to the αSyn RT-QuIC reactions. The blood, concentrates or blood-treated bead samples from synucleinopathy patients cause more rapid increase in ThT fluorescence in the reactions than samples from non-synucleinopathy cases, allowing discrimination between synucleinopathy and non-synucleinopathy patients.

Example 10

Detection of αSyn Seeding Activity in Olfactory Mucosa Samples

Figure 8A:
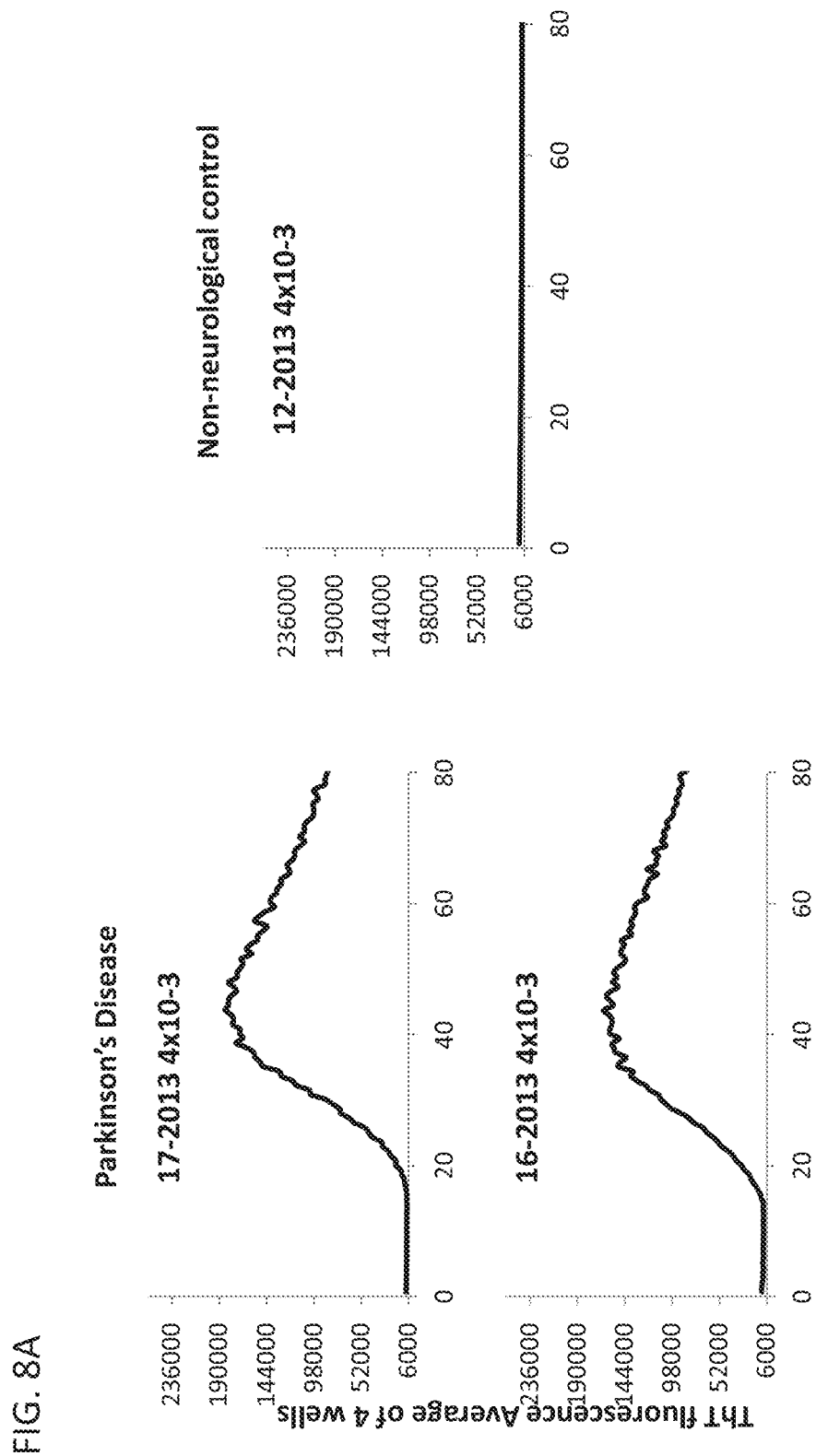
FIGS. 8A-8B. Detection of endogenous αSyn seeding activity in olfactory mucosa (OM) samples from Parkinson's disease patients. OM samples were homogenized in PBS as previously described (Orru et al. NEJM 371: 519-529 (2014) and diluted to give a final concentration of $10^{-2}$ and $10^{-3}$. Quadruplicate reactions were seeded with the indicated dilutions with each trace in the graphs representing average fluorescence readings for each sample dilution. Samples were collected from two Parkinson's disease, three Alzheimer's disease, one CBD and one non-neurological control patient. The results show specific detection of αSyn seeding activity in OM samples from Parkinson's disease patients but not several non-synucleinopathy control samples.
Figure 8B:
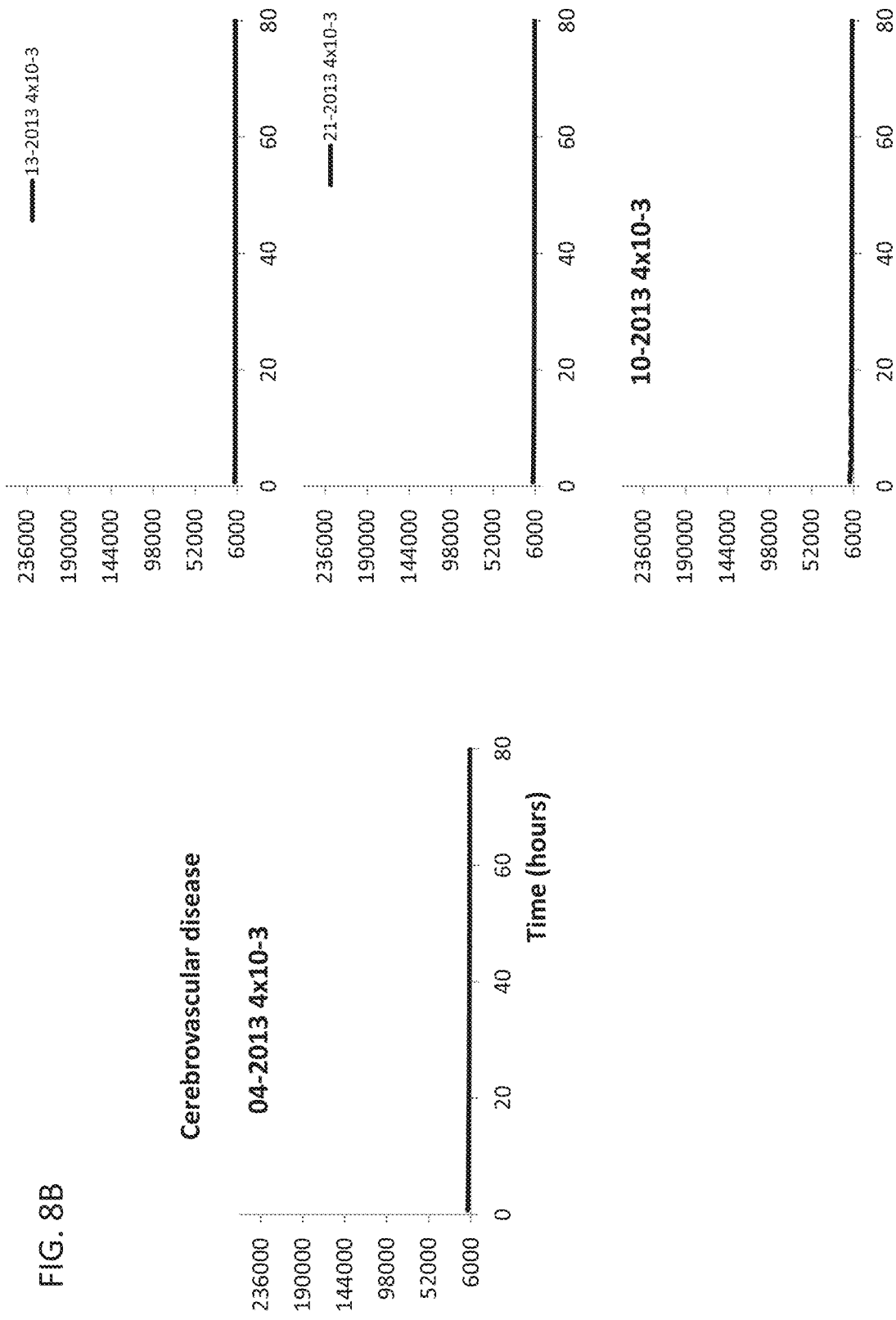

In order to identify additional tissue specimens that can be collected from living patients and, therefore, brushings of the olfactory mucosal (OM) layer that lines the upper nasal vault were used. Spiking experiments were first performed to determine if the components, or matrix, of OM samples interfered with αSyn RT-QuIC assays. Dilutions of brain tissue from synucleinopathy [diffuse Lewy body disease (DLBD)] or non-synucleinopathy [corticobasal degeneration (CBD)] were added to phosphate buffered saline (PBS) or to an OM sample from a non-synucleinopathy patient. Comparisons of these preparations in αSyn RT-QuIC assays indicated that there was no major interference by OM components (FIGS. 7A-7B). OM samples were then collected from two living Parkinson's disease (PD) cases and αSyn seeding activity was detected. However, αSyn seeding activity was not detected in OM samples from five non-synucleinopathy control patients of various types (FIGS. 8A-8B). These results evidence that αSyn seeding activity of PD cases can be detected in OM brushings.

In some protocols, brushings or swabbings of the nasal mucosa or olfactory neuroepithelium, for example collected as described in Bongianni et al., JAMA Neurology 74: 155-162, are processed as described in Orrù et al, New Engl J Med 371:519-529, and added to αSyn RT-QuIC reactions. In some cases, the samples are treated to disrupt cellular membranes, for example with freeze-thaw cycles, sonication, bead beaters, nuclease, mucinase, protease and/or lipase treatments prior to addition to αSyn RT-QuIC reactions. When protease treatments are used, the protease inhibitors are added prior to the next step in the protocol. In some cases, the resulting disrupted samples are added directly to the αSyn RT-QuIC reactions. In other cases, synucleinopathy-associated αSyn seeds in the nasal brushing samples are first captured by binding to beads or other particles coated with antibodies or other reagents that bind to synucleinopathy-associated αSyn seeds. The beads are then rinsed prior to being added to αSyn RT-QuIC reactions. In other cases, synucleinopathy-associated αSyn seeds in the nasal brushing samples are first concentrated, for example by phosphotungstate anion (PTA) precipitation or exosome isolation, and then processed prior to being added to the αSyn RT-QuIC reactions. The samples from synucleinopathy patients cause more rapid increase in ThT fluorescence in the reactions than samples from non-synucleinopathy cases, allowing discrimination between synucleinopathy and non-synucleinopathy patients.

Example 11

Relative αSyn Seeding Activities in CSF and Brain Tissue from PD and DLB Cases

Figures 9A, 9B:
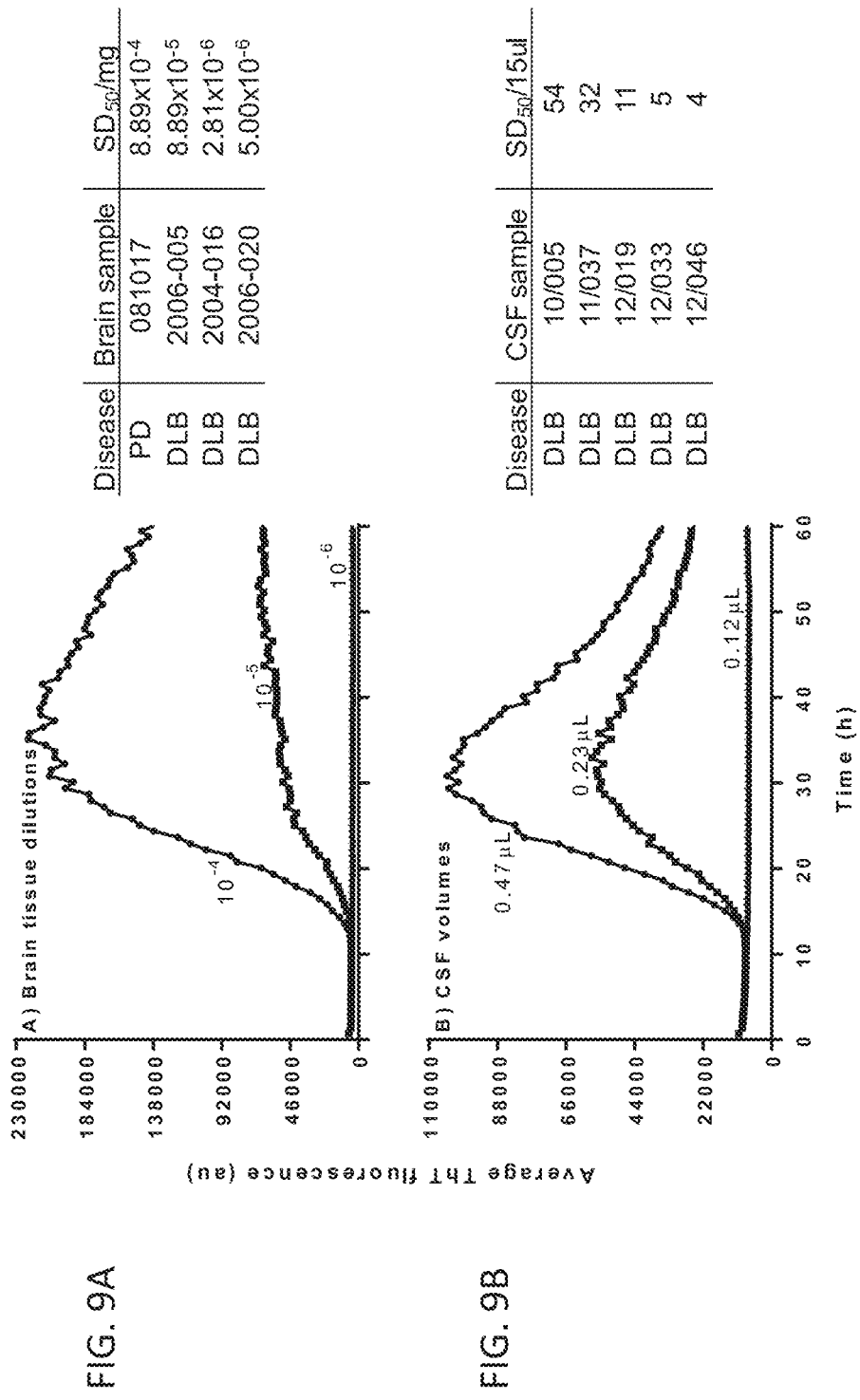
FIGS. 9A-9B. End-point dilutions of synucleinopathy BH (FIG. 9A; sample #081017) or CSF (FIG. 9B; sample #10/005) samples by αSyn RT-QuIC. BH samples (FIG. 7A) were serially diluted 10-fold in PBS and CSF samples (FIG. 7B) were serially diluted two-fold in into normal pooled CSF. The values by each trace represent the tissue equivalents loaded into the reaction. Each sample trace represents the average ThT signal of quadruplicate wells. Tables to the right of each graph indicate the concentration of $SD_{50}$ units calculated by Spearman-Kärber analysis for each case.

To quantify the αSyn RT-QuIC seeding activities in samples from synucleinopathy cases, end-point dilution analyses were preformed of frontal cortex brain tissue from representative PD (n=1) and DLB (n=3) cases and CSF samples from 5 DLB cases. All 4 cases indicated that positive reactions were obtained out to 10-5-10-6 dilutions of either the PD and DLB brain tissues (FIG. 9). Positive reactions were obtained from as little as 0.2 μl CSF per reaction well in DLB cases (FIG. 9). Spearman-Kärber analyses (Dougherty R M (1964) Animal virus titration techniques. In: Harris R J C (ed) Techniques in experimental virology. Academic Press, Inc., City, pp 183-186) provided estimates of the concentrations of seeding activity units giving positive reactions in 50% of replicate reactions, i.e., the 50% "seeding doses" or SD50s (Wilham et al., (2010). PLoS Path 6: e1001217 Doi 10.1371/journal.ppat.1001217) (FIG. 7). The DLB and PD samples contained ~106 SD50 per mg of tissue while the CSF samples had 4-54 SD50s per 15 μl, i.e., usual sample volume. The latter results indicated that these synucleinopathy CSF specimens had seeding activities that are substantially higher than the minimum detectable level of 1 SD50. However, on a per weight basis, seeding activity in brain tissue appeared to be $10^4$-$10^5$-fold higher than the seeding activities measured in PD and DLB CSF specimens (FIG. 9). Slightly different conditions were used for the brain homogenate and CSF specimens.

Example 12

Analytical Sensitivity Using Synthetic αSyn Fibrils

Figure 10:
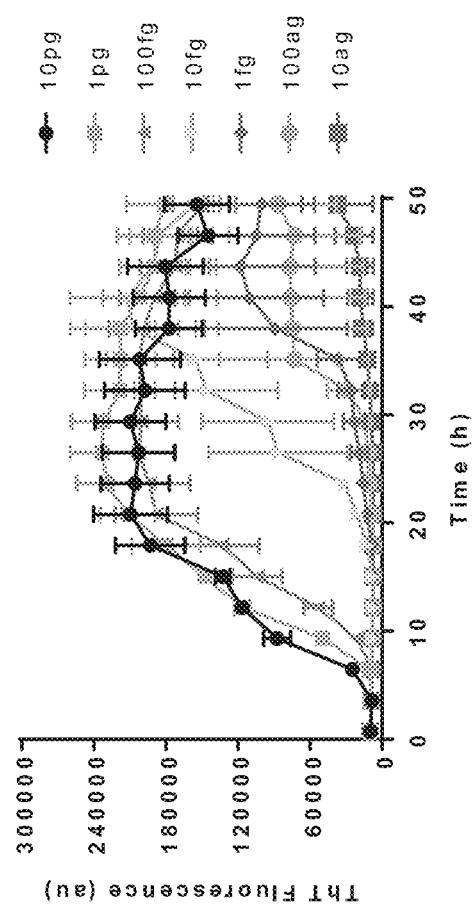
FIG. 10. End-point dilutions of synthetic seeds spiked into CSF. Synthetic rαSyn fibrils were generated by continuous shaking at 1000 rpm at 37° C. for 3 days in a 1.5 mL tube containing 100 μL of 1 mg/ml WT rαSyn. Samples were monitored by ThT fluorescence. Following fibrillization the samples were spiked into non-synucleinopathy CSF and diluted in 10-fold serial dilutions. Each sample trace represents the average t SEM ThT signal of quadruplicate wells. For clarity, data points were plotted every fourth point and negative controls, which were all below the positivity threshold, are not displayed.

To obtain an indication of the analytical sensitivity of αSyn RT-QuIC, synthetic rαSyn fibrils were prepared, spiked into non-synucleinopathy CSF and assayed using serial dilutions. As little as 100 ag of the synthetic fibril preparations gave at least 2/4 positive replicate reactions (FIG. 10), which was at least as sensitive analytically as the αSyn PMCA assay (Shahnawaz et al. (2017) JAMA Neurol 74: 163-172 Doi 10.1001/jamaneurol.2016.4547).

Example 13

Use of IO Particles to Capture αSyn Seeds from Biological Specimens

To improve the sensitivity of αSyn RT-QuIC assays of biological specimens and reduce the potential for assay interference by components of those specimens, IO particles were tested as a vehicle of binding and sequestering αSyn seeds from human plasma and CSF samples. IO particles are useful for capturing transmissible spongiform encephalopathy prions that can then be detected by protein misfolding cyclic amplification (PMCA), RT-QuIC and other techniques (Miller M B et al. J Virol, 2011 March; 85(6):2813-7. doi: 10.1128/JVI.02451-10. Epub 2011 Jan. 12; Jacobson K H et al., Environmental Sci and Technol, 2013 Jul. 2; 47(13):6925-34. doi: 10.1021/es3045899. Epub 2013 May 30; Denkers N D et al., J Gen Virol, 2016 August; 97(8): 2023-9. doi: 10.1099/jgv.0.000515. Epub 2016 May 27, incorporated herein by reference). Iron has a potential role in PD and is present in the Lewy bodies of PD. It was determined that IO was useful for capturing αSyn aggregates from tissues or fluids, which can then be used in the methods disclosed herein.

Figure 11:
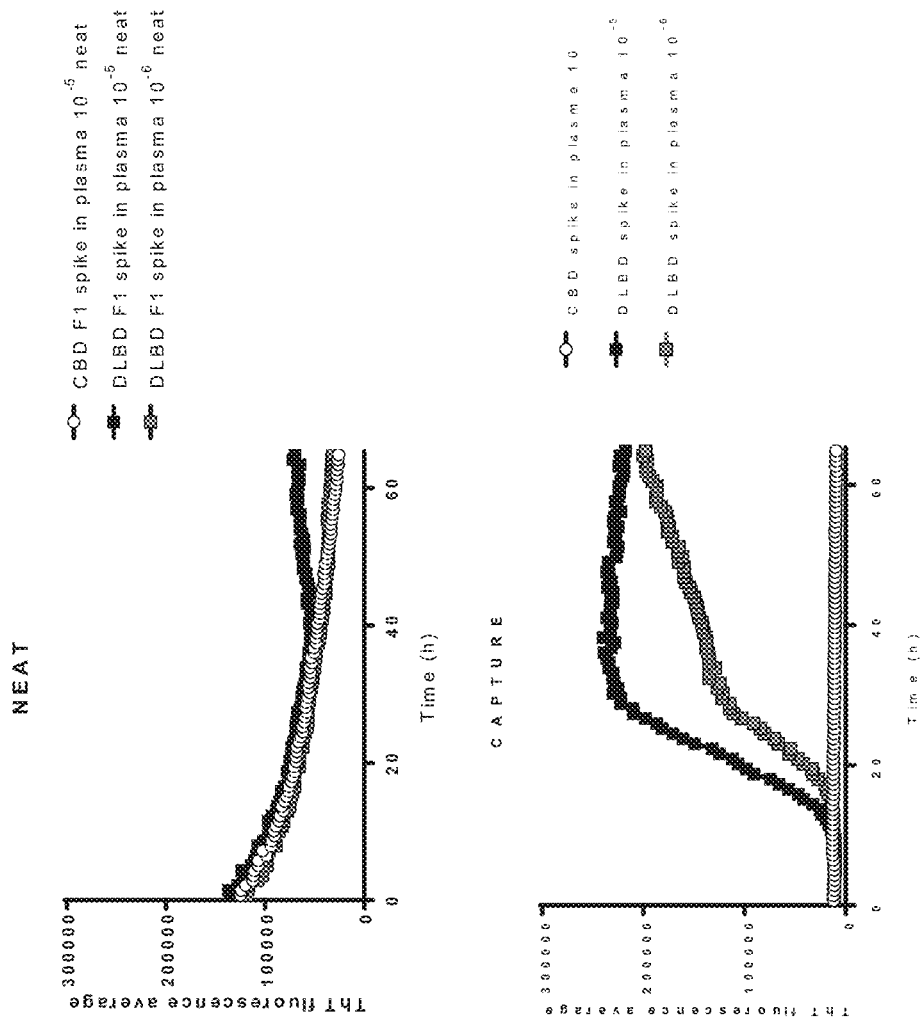
FIG. 11. Comparison of αSyn detection in spiked plasma by direct addition of the plasma to the reaction (neat) and following iron oxide (IO) capture (capture). 500 μL of normal human plasma were spiked with brain homogenates to give final concentrations of $10^{-5}$ CBD brain tissue or $10^{-5}$ and $10^{-6}$ DLBD brain tissue dilutions. 2 μL per well of the indicated dilutions were loaded into quadruplicate reactions (neat). 2 μL (98 μg) of IO particles (capture) were added to the 500 μL of spiked plasma, briefly sonicated and incubated at room temperature for 2 hours with "end-over-end" rotation. Next, the IO particles were washed once in PBS. The particles were resuspended in 10 μL of 0.1% SDS in PBS by brief sonication and transferred to a clean tube. 2 μL were then loaded into each quadruplicate well. While only very slow subtle seeding activity was detected in the DLDB $10^{-5}$ neat reaction, capture with IO particles allowed for robust detection of $10^{-5}$ and $10^{-6}$ DLBD brain tissue dilutions spiked into plasma. The net effect is that IO allowed a 50-fold concentration of DLBD seeds from 500 μL dilute spiked plasma samples such that detection was greatly enhanced over that allowed by analyses of 2 μL neat spiked plasma with the same ($10^{-6}$) or 10-fold higher ($10^{-5}$) concentration of DLBD brain homogenate. IO capture of seeding activity enhanced αSyn RT-QuIC detection in DLBD spiked plasma. IO capture increased assay sensitivity by permitting collection and detection of αSyn seeds from much larger volumes of plasma.
Figure 12:
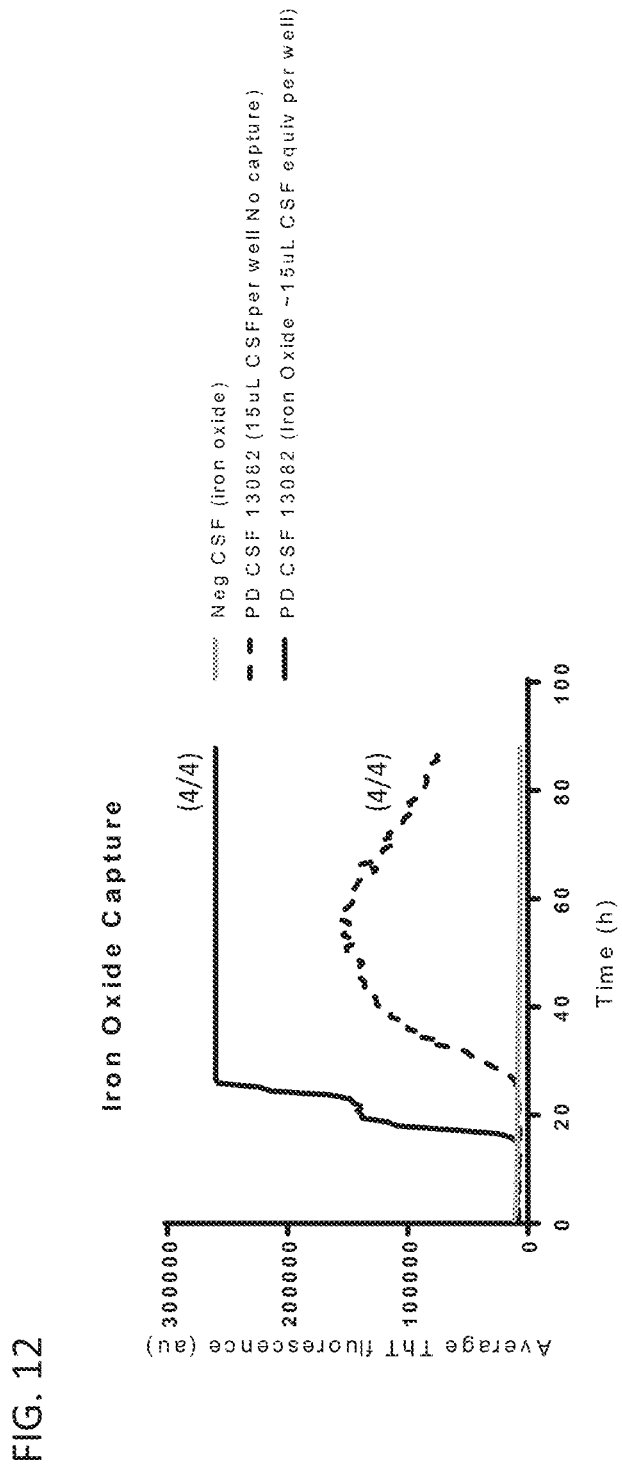
FIG. 12. Comparison of αSyn seeding activity detection in CSF by direct addition of the CSF to the reaction (neat) or following IO capture (capture). 15 μL of endogenous CSF from a DLBD patient (sample number 13082) were loaded into quadruplicate wells (neat) or spiked into 500 μL of normal human CSF. Endogenous αSyn seeding activity spiked into CSF was captured using 2p L (98 μg) of IO particles. The particles were washed once in PBS prior to being resuspended in 10 μl of PBS. Following sonication, 2 μL of this suspension were then loaded into each well in quadruplicate reactions. A notable enhancement in signal intensity and speed of the reaction was observed following capture with the IO beads. Capture with IO particles enhanced detection of Parkinson's disease specific seeding activity in CSF.
Figure 13A:
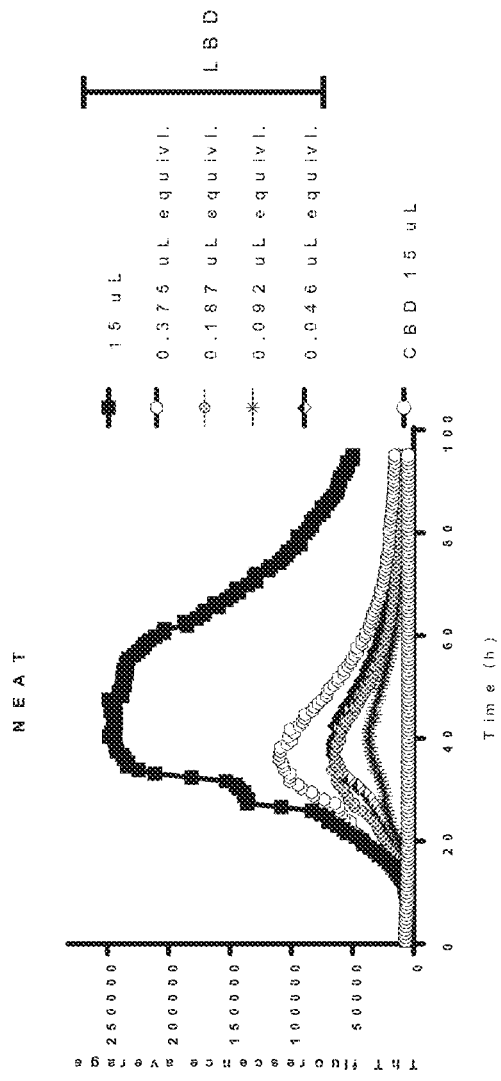
FIGS. 13A-13B. Comparison of αSyn RT-QuIC testing of neat vs. IO capture of endogenous LBD seeding activity in CSF.
Figure 13B:
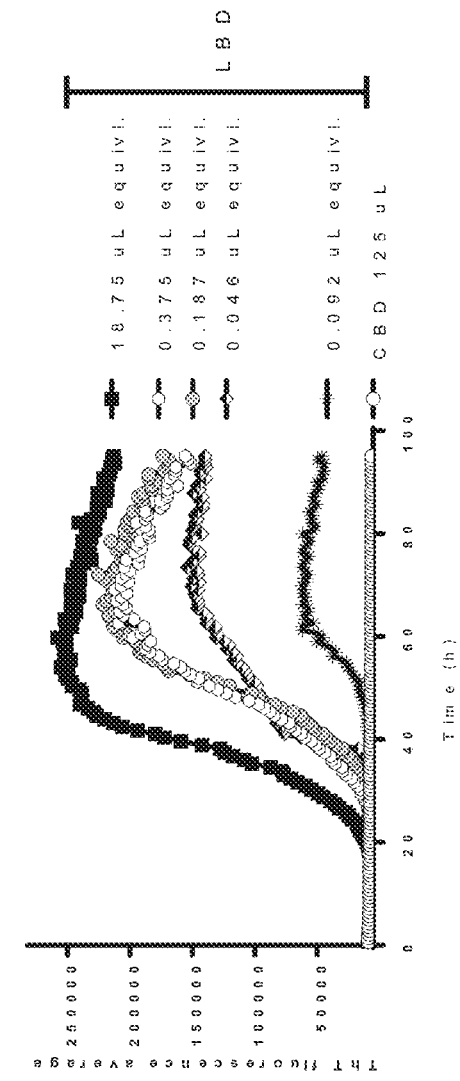

FIG. 11 shows assays of DLBD seeds spiked into 500 μL normal human plasma and then captured on IO particles. This protocol allowed detection of seed concentrations that were undetectable if the same amount of seed was added directly to αSyn RT-QuIC reactions in the maximum non-inhibitory volume of plasma, i.e. ~2 μL. Thus, IO capture increased assay sensitivity by permitting the collection and detection of αSyn seeds from much larger volumes of plasma than can be added directly to RT-QuIC reactions without inhibition by matrix components. Similar experiments showed that αSyn seeding activity that is endogenous in the CSF of a DLBD patient could be captured on IO particles and detected with enhanced signal intensity and speed in αSyn RT-QuIC assays (FIG. 12). Endpoint dilution assays with LBD (Lewy Body dementia) CSF indicated that minimum detectable amounts of αSyn seeding activity in CSF, when added directly to αSyn RT-QuIC reactions, can also be detected after >2,700-fold dilution into normal CSF if captured on IO particles (FIGS. 13A-13B). Thus, IO capture increased the sensitivity of the assay by permitting the collection and detection of αSyn seeds from much larger volumes of CSF and plasma.

Example 14

Differential Effects of 0.05% SDS on Detection αSyn Seeding Activity Captured with IO from Human CSF and Plasma To try to further improve the sensitivity of αSyn RT-QuIC when testing samples subjected to IO capture, the effect of resuspending the IO particles (after the capture step) in either 0.05% SDS in PBS was compared to PBS alone. It was determined that, with human CSF samples, resuspension in PBS alone was preferable for maximal sensitivity (FIGS. 14A and 14B). In contrast resuspension in 0.05% SDS in PBS was preferable for human plasma samples (FIGS. 14C and 14D).

Example 15

Improved Fluorescence Detection in the Presence of IO by Increasing the Thioflavin T (ThT) Concentration The αSyn RT-QuIC assays containing IO particles tended to have lower maximal ThT fluorescence in synucleinopathy-seeded reactions. To increase sensitivity, the effects of increasing the ThT concentration 10-fold was determined. It was possible that the IO was impeding ThT fluorescence. FIG. 15 presents evidence demonstrating that, while the lower ThT concentration can be used, the higher ThT concentration increased the strength of ThT fluorescence when testing DLBD-spiked human CSF or plasma samples. However, less pronounced effects were seen in the case of plasma samples. Thus, both high and low concentration of ThT can be used, although increased concentration of ThT increased sensitivity.

Example 16

Figure 17:
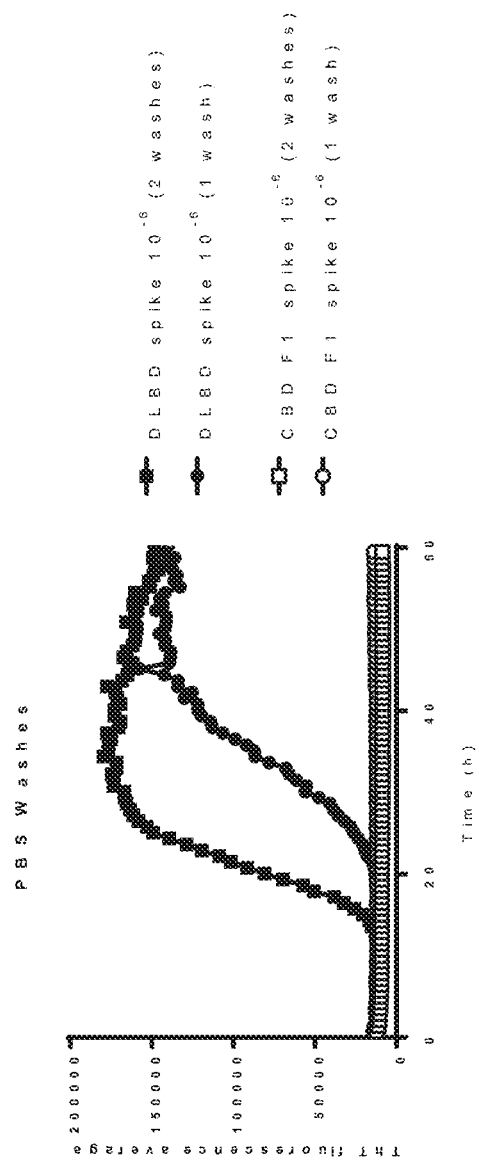
FIG. 17. Comparison of 1 vs. 2 PBS washes in IO particles capture of αSyn seeding activity spiked into human plasma. Human plasma (500 µL) was spiked to give a $10^{-6}$ CBD brain tissue dilution or $10^{-6}$ DLBD brain tissue dilution. αSyn seeding activity was captured using 98 µg of IO particles with an incubation of 2 hours at room temperature. At the end of the capture the particles were washed either once or twice with PBS and resuspended in 0.1% SDS/PBS and briefly sonicated at 63% power prior to seeding 4 wells. The traces are the average of four replicate wells. Although all conditions allowed detection of αSyn seeding activity the data showed stronger and faster detection of seeding activity when the particles were subjected to two washes. Thus, washes can improve the performance of the assay, but are not required.

Improved αSyn RT-QuIC Detection of DLBD Seeding Activity in Human Plasma with PBS Washes and 0.05-0.1% SDS It was possible that αSyn seeds captured on IO beads could have inhibitory substances bound to them. Thus, the effects of post-capture PBS washes and resuspension in SDS solutions were tested. FIGS. 16 and 17 show that when the IO particles were twice washed with PBS and resuspended in 0.1% SDS in PBS, there was stronger, faster and more sensitive detection of DLBD seeding activity spiked into human plasma. Thus, washing may remove inhibitory substances and increase sensitivity. One or more washing steps can be used.

Example 17

Figure 18:
FIG. 18. End-point dilution analysis of captured of αSyn seeding activity in human plasma. 500 µL of normal non-diseased human plasma were spiked with serial dilutions of either a CBD ($10^{-6}$ tissue dilution in 500 µL of plasma) or DLBD ($10^{-6}$-$10^{-8}$ brain tissue dilutions in 500 µL of plasma) brain sample. Seeding activity was captured from plasma using 2 µL (98 µg) of IO particles in a 2 hours incubation at room temperature. Quadruplicate reactions were seeded with ⅛ of these particles and data was plotted using the average of quadruplicate reactions. Although αSyn seeding activity could be weakly detected without IO capture (FIG. 11A), the results indicate that IO capture allows stronger detection of lower levels of αSyn, specifically $10^{-8}$ DLBD brain tissue dilutions in 500 µL human plasma. IO capture of αSyn seeding activity enhanced detection in dementia with Lewy Bodies spiked plasma.

End-Point Dilution Analysis of Captured αSyn Seeding Activity in Human Plasma In order to determine the sensitivity of αSyn RT-QuIC with IO capture for detecting αSyn seeds spiked into normal human plasma, serial 10-fold dilutions of DLBD brain homogenate in plasma were assessed. The results shown in FIG. 18 indicate that IO capture allows detection of $10^{-8}$ DLBD brain tissue dilutions in 500 μL human plasma. Thus, although the assays can be performed without IO, the IO significantly increased sensitivity of the assays.

Example 18

Efficiency of IO Capture from Human Plasma and CSF

Figure 19:
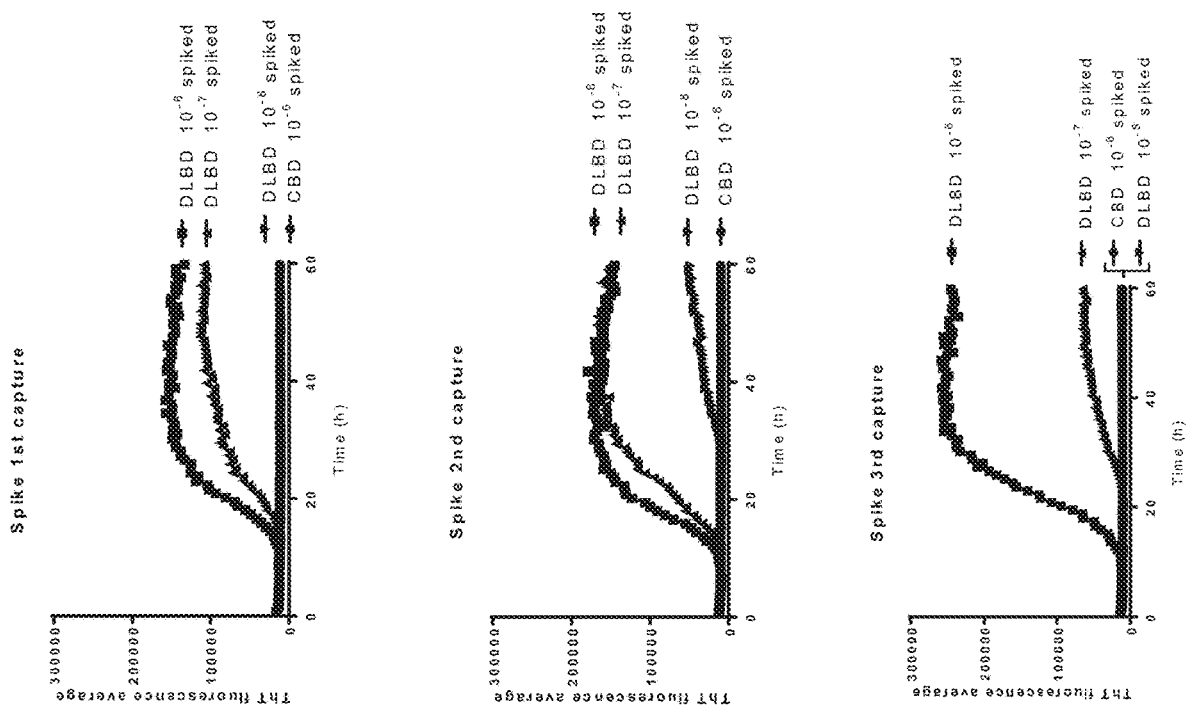
FIG. 19. αSyn RT-QuIC assessment of IO capture efficiency in human plasma. Non-diseased normal plasma (500 µL) was spiked with the indicated serial dilutions of a DLBD and CBD brain tissue and subjected to three consecutive captures with the same spiked material being incubated with fresh 2 µL (98 µg) of IO particles for 2 hours at room temperature. After each capture the particles were washed twice with PBS, resuspended in 8 µL of 0.1% SDS/PBS and stored at 4° C. until ready to be tested. Prior to seeding the wells, the particles were briefly sonicated at 63% power. ThT fluorescence traces are the average of 4 replicate wells. The results showed that by the third capture slightly less seeding activity was detected at the $10^{-7}$ brain tissue dilution spike than the second capture. This suggested that, by the third capture, less seeding activity is left behind than the $1^{st}$ or $2^{nd}$ capture. In any case, as shown below for CSF (see FIG. 20), only a fraction of the seeds present in plasma were captured at each round. Nonetheless, discrimination between αSyn positive and negative samples was clearly evident using the IO capture method. The results showed that multiple rounds of IO capture can be used.
Figure 20:
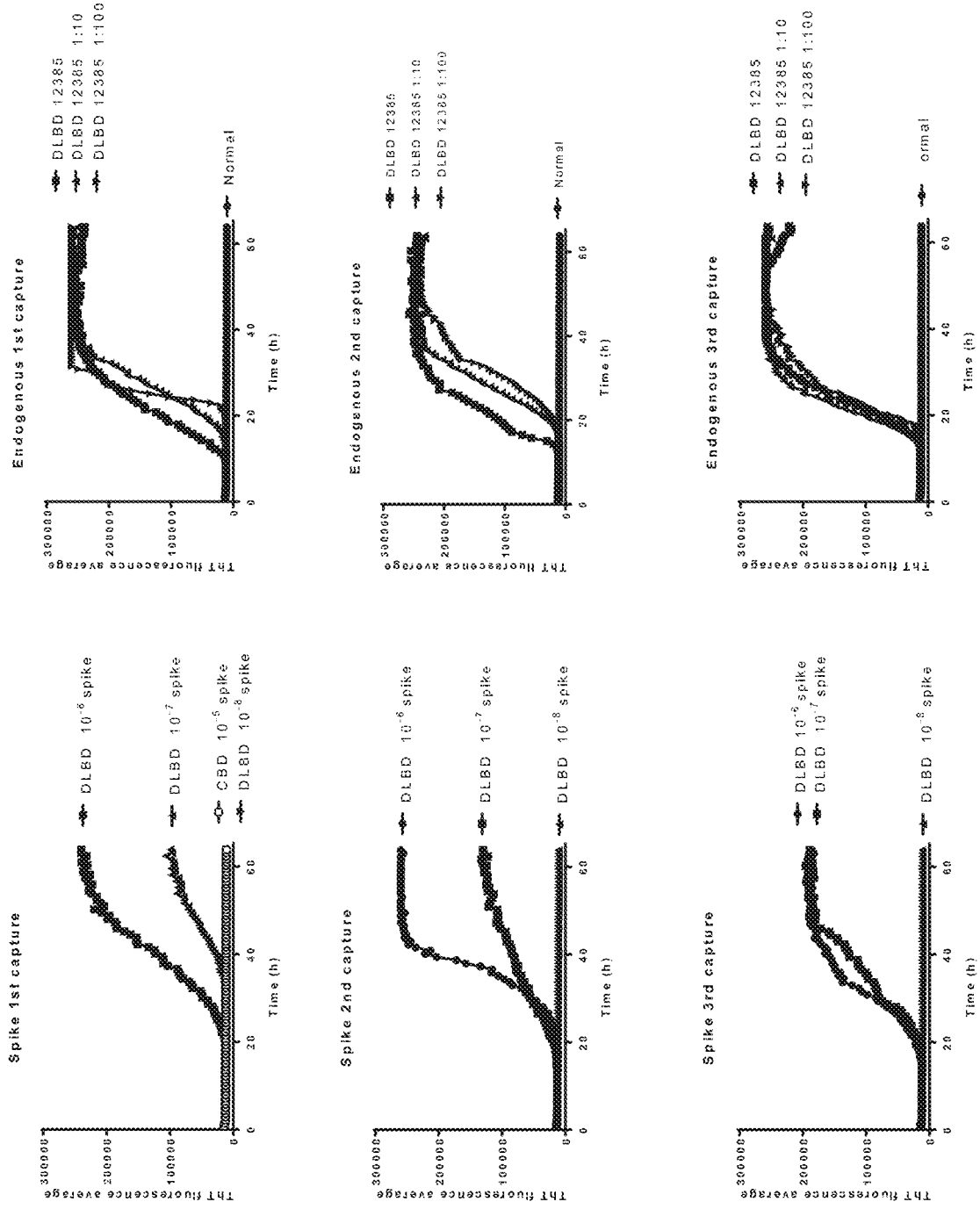
FIGS. 20A-20B. αSyn RT-QuIC assessment of IO capture efficiency in human CSF.
Figure 21:
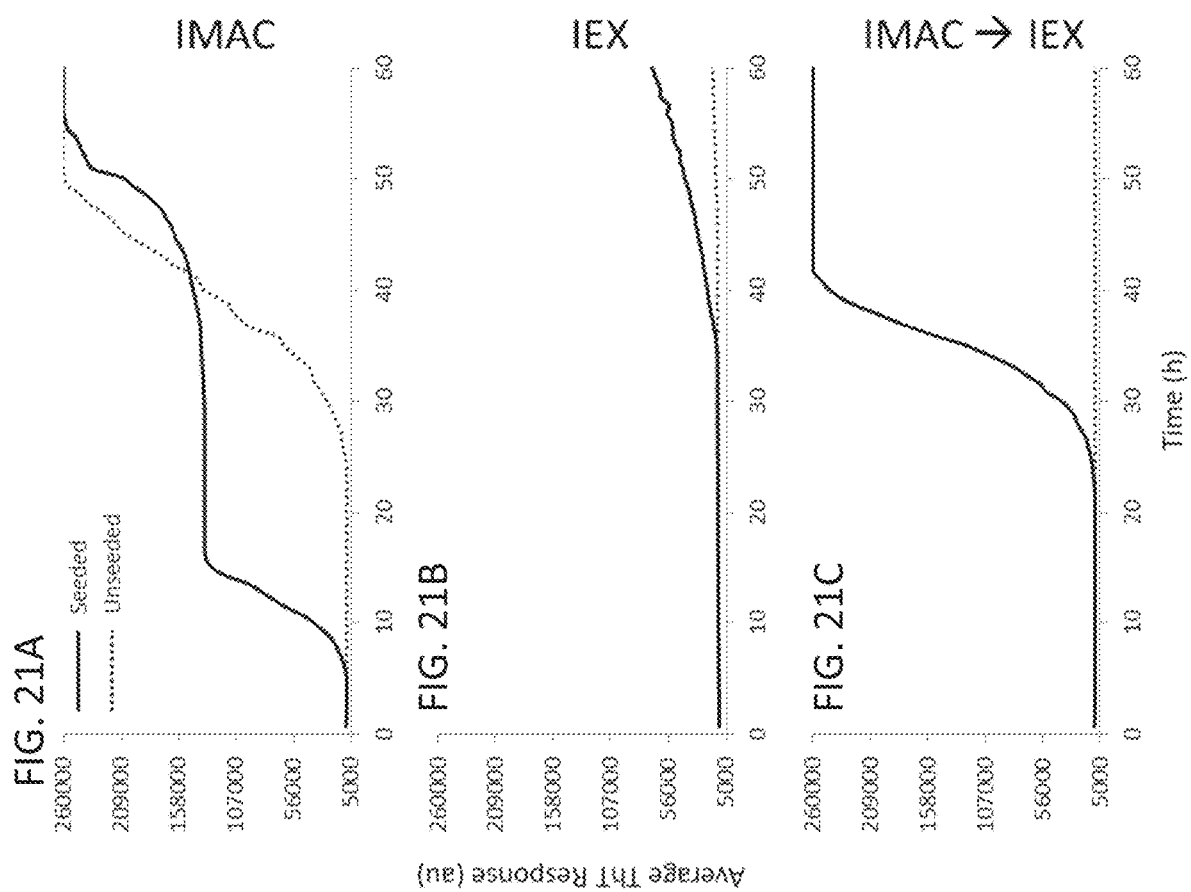
FIGS. 21A-21C. Purification. Alpha-syn RT-QuIC reactions were performed using wild-type recombinant alpha-synuclein substrates purified with an immobilized metal affinity column (IMAC.
Figure 22:
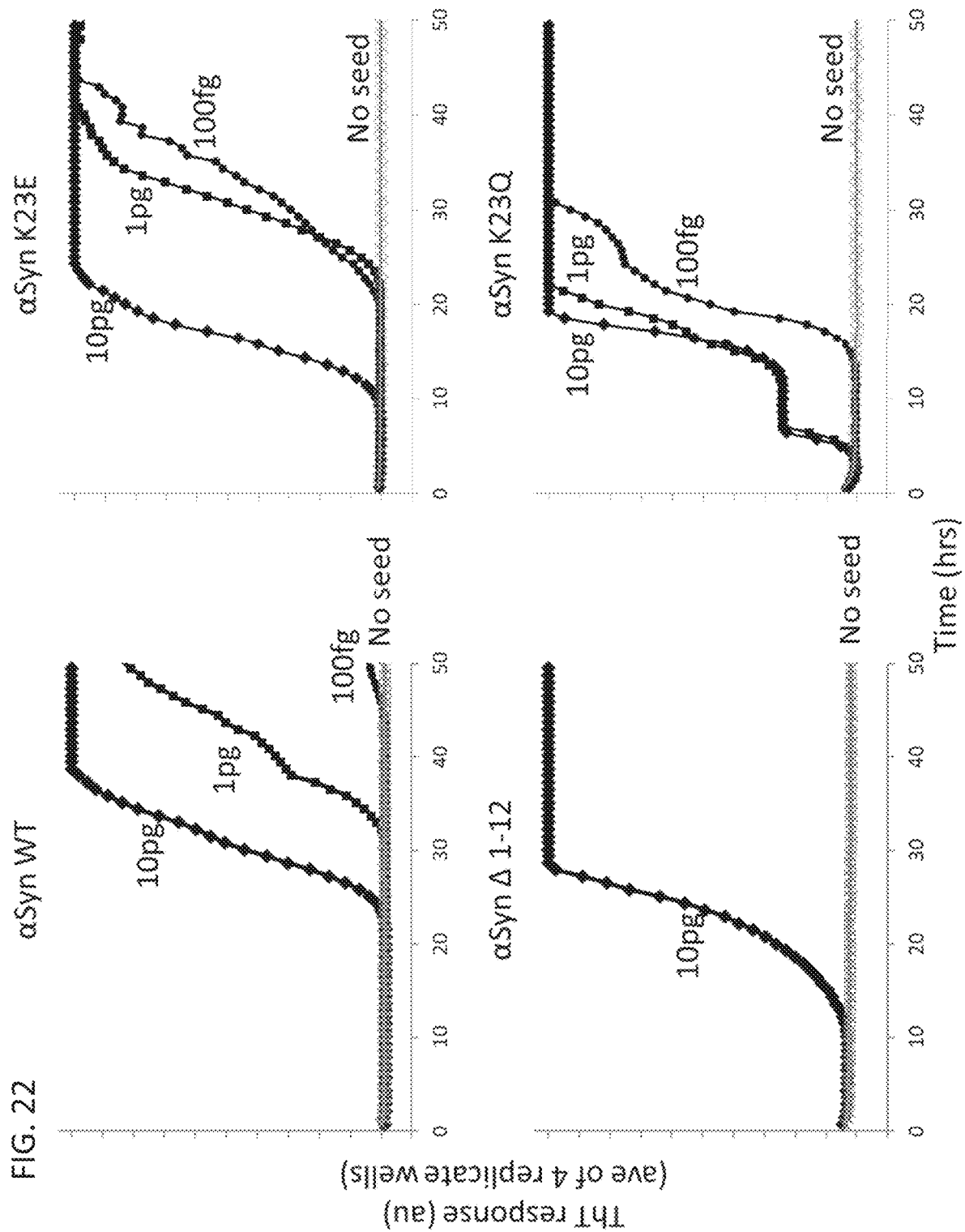
FIG. 22. Comparison of αSynuclein mutant substrates to wild-type. To generate quantifiable artificial seed for spiking experiments, synthetic recombinant αSynuclein (rαSyn) fibrils were generated by continuous shaking at 1000 rpm at 37° C. for 3 days in a 1.5 mL tube containing 100 μL of 1 mg/ml WT rαSyn. Fibril growth was then monitored by ThT fluorescence. Following fibrillization the samples were serially diluted in 10-fold in phosphate buffer. Two microliters of each dilution, yielding final seed concentrations of 10 pg, 1 pg, or 100 fg, or a 10 pg monomeric ("No seed") αSyn were used to seed reactions containing substrates consisting of wild-type αSyn, K23E αSyn, K23Q αSyn, or αSyn with amino acids 2-11 deleted from its sequence. Each sample trace represents the average ThT signal of quadruplicate wells. With the exception of Syn Δ 2-11, the other mutants (K23E and K23Q) had faster amplification kinetics and better sensitivity than the wild-type. The K23Q mutant substrate showed increased sensitivity and most rapid detection in comparison to the other substrates tested.

To assess the proportion of DLBD seeding activity that is captured from plasma and CSF, serial IO capture steps (up to 3) were performed and the IO particles were assessed after each step. The results shown in FIG. 19 and FIG. 20 revealed that αSyn seeding activity was readily detected even after 3 capture rounds, indicating that in each round, only a minority of the DLBD seeds were being captured. However, the sensitivity of αSyn RT-QuIC was adequate to allow clear discrimination of positive vs. negative samples at each round. Thus, a single capture step, or multiple capture steps, can be used with the assay.

In view of the many possible embodiments to which the principles of the disclosure may be applied, it should be recognized that the illustrated embodiments are only examples and should not be taken as limiting the scope of the disclosure. Rather, the scope of the disclosure is defined by the following claims.

The invention claimed is:

1. A method of determining whether a subject has a synucleinopathy, comprising:
    A) performing an alpha synuclein (aSyn) seeding assay on a biological sample from the subject comprising:
        i) contacting the biological sample with a soluble mutated recombinant alpha synuclein (rαSyn) to form a reaction mixture, wherein the reaction mixture comprises about 0.1 mg/ml of the soluble mutated rαSyn, about 4 to 8 beads per 100 μl, and a pH of about 8.0, and wherein the soluble mutated rαSyn comprises an amino acid sequence comprising a) one to eight point mutations in SEQ ID NO: 1, wherein the point mutations are at residues K23, D2, K21, K45, T59, G67, V77, and/or A78 and/or b) a deletion of up to ten amino acids in amino acids 2-11 of SEQ ID NO: 1;
        ii) incubating the reaction mixture at a temperature of 35-50° C. to permit coaggregation of misfolded αSyn aggregates present in the biological sample with the mutated rαSyn;
        iii) maintaining incubation conditions that promote coaggregation of the mutated rαSyn with the misfolded αSyn aggregates to result in a conversion of the soluble mutated rαSyn to mutated rαSyn aggregates while inhibiting spontaneous aggregation of soluble mutant rαSyn; and
        iv) agitating mutated rαSyn aggregates formed during step iii), wherein the conditions comprise shaking the reaction mixture in a shaking cycle, wherein each shaking cycle comprises a period of rest and a period of shaking; and
    B) detecting misfolded mutated rαSyn aggregates in the reaction mixture, and wherein detection of misfolded mutated rαSyn aggregates in the reaction mixture indicates that the subject has the synucleinopathy.

2. The method of claim 1, wherein the reaction mixture comprises 6 to 8 beads per 100 μl.

3. The method of claim 1, wherein the reaction mixture comprises about 6 beads per 100 μl.

4. The method of claim 1, wherein the beads are glass beads.

5. The method of claim 1, wherein the beads are about 1 mm in diameter.

6. The method of claim 1, wherein the reaction mixture is incubated at a temperature of about 42° C.

7. The method of claim 1, wherein the period of rest and the period of shaking are each about 60 seconds in length.

8. The method of claim 1, wherein shaking is performed at about 400 rpm.

9. The method of claim 1, wherein the biological sample is cerebrospinal fluid (CSF) sample, and wherein the reaction mixture further comprises 0.001%-0.005% sodium dodecyl sulfate (SDS).

10. The method of claim 9, wherein the reaction mixture comprises 0.0015% SDS.

11. The method of claim 9, wherein the reaction mixture comprises about 15 μl of the CSF sample per 100 μl of the reaction mixture.

12. The method of claim 1, wherein the subject is a human, and the synucleinopathy is Parkinson disease, Lewy body dementia, or multiple system atrophy.

13. The method of claim 1, wherein the reaction mix of step i) further comprises a detectable label.

14. The method of claim 13, wherein detecting misfolded mutated raSyn aggregates comprises the use of fluorescence.

15. The method of claim 14, wherein detecting the presence of misfolded mutated raSyn aggregates comprises the use of thioflavin T (ThT).

16. The method of claim 1, wherein agitating aggregates in step (iv) comprises agitating aggregates in the absence of sonication.

17. The method of claim 1, wherein misfolded mutated raSyn aggregates are detected within 24-48 hours.

18. The method of claim 1, wherein the soluble mutated raSyn comprises the amino acid sequence of any one of SEQ ID NOs: 3, 4, 5, 6, 7, and 8, 13 and 14.

19. A method of determining whether a subject has a synucleinopathy, comprising:
    A) performing an alpha synuclein (αSyn) seeding assay on a biological sample, or fraction thereof, from the subject, comprising:
        i) contacting the biological sample or a fraction thereof with a soluble mutated recombinant alpha synuclein (rαSyn) to form a reaction mixture, wherein the soluble mutated rαSyn comprises SEQ ID NO: 1 comprising at least one point mutation, wherein the at least one point mutation comprises K23E;
        ii) incubating the reaction mixture to permit coaggregation of misfolded αSyn aggregates present in the biological sample or fraction thereof with the mutated rαSyn;
        iii) maintaining incubation conditions that promote coaggregation of the mutated rαSyn with the misfolded αSyn aggregates to result in a conversion of the soluble mutated rαSyn to mutated rαSyn aggregates while inhibiting spontaneous aggregation of soluble mutant rαSyn; and iv) agitating mutated rαSyn aggregates formed during step iii), wherein the conditions comprise shaking the reaction mixture in a shaking cycle, wherein each shaking cycle comprises a period of rest and a period of shaking; and B) detecting misfolded mutated rαSyn aggregates in the reaction mixture, and wherein detection of misfolded mutated rαSyn aggregates in the reaction mixture indicates that the subject has the synucleinopathy.

20. The method of claim 19, wherein the soluble mutated rαSyn comprises the amino acid sequence of SEQ ID NO: 3 or SEQ ID NO: 4.

* * * * *

SEQUENCE LISTING

```
<160> NUMBER OF SEQ ID NOS: 24

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
```

```
                    65                  70                  75                  80
Thr Val Glu Gly Ala Gly Ser Ile Ala Ala Thr Gly Phe Val Lys
                85                  90                  95

Lys Asp Gln Leu Gly Lys Asn Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
        130                 135                 140

<210> SEQ ID NO 2
<211> LENGTH: 160
<212> TYPE: PRT
<213> ORGANISM: Artificial Sequence
<220> FEATURE:
<223> OTHER INFORMATION: 6XHis SNCA

<400> SEQUENCE: 2

Met Gly Ser Ser His His His His His His Ser Ser Gly Leu Val Pro
1               5                   10                  15

Arg Gly Ser His Met Asp Val Phe Met Lys Gly Leu Ser Lys Ala Lys
            20                  25                  30

Glu Gly Val Val Ala Ala Ala Glu Lys Thr Lys Gln Gly Val Ala Glu
        35                  40                  45

Ala Ala Gly Lys Thr Lys Glu Gly Val Leu Tyr Val Gly Ser Lys Thr
    50                  55                  60

Lys Glu Gly Val Val His Gly Val Ala Thr Val Ala Glu Lys Thr Lys
65                  70                  75                  80

Glu Gln Val Thr Asn Val Gly Gly Ala Val Val Thr Gly Val Thr Ala
                85                  90                  95

Val Ala Gln Lys Thr Val Glu Gly Ala Gly Ser Ile Ala Ala Ala Thr
            100                 105                 110

Gly Phe Val Lys Lys Asp Gln Leu Gly Lys Asn Glu Glu Gly Ala Pro
        115                 120                 125

Gln Glu Gly Ile Leu Glu Asp Met Pro Val Asp Pro Asp Asn Glu Ala
    130                 135                 140

Tyr Glu Met Pro Ser Glu Glu Gly Tyr Gln Asp Tyr Glu Pro Glu Ala
145                 150                 155                 160

<210> SEQ ID NO 3
<211> LENGTH: 140
<212> TYPE: PRT
<213> ORGANISM: Artificial Sequence
<220> FEATURE:
<223> OTHER INFORMATION: SNCA K23E

<400> SEQUENCE: 3

Met Asp Val Phe Met Lys Gly Leu Ser Lys Ala Lys Glu Gly Val Val
1               5                   10                  15

Ala Ala Ala Glu Lys Thr Glu Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80
```

```
Thr Val Glu Gly Ala Gly Ser Ile Ala Ala Ala Thr Gly Phe Val Lys
                 85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 4
<211> LENGTH: 160
<212> TYPE: PRT
<213> ORGANISM: Artificial Sequence
<220> FEATURE:
<223> OTHER INFORMATION: 6XHis SNCA K23E

<400> SEQUENCE: 4

Met Gly Ser Ser His His His His His His Ser Ser Gly Leu Val Pro
1               5                   10                  15

Arg Gly Ser His Met Asp Val Phe Met Lys Gly Leu Ser Lys Ala Lys
            20                  25                  30

Glu Gly Val Val Ala Ala Ala Glu Lys Thr Glu Gln Gly Val Ala Glu
        35                  40                  45

Ala Ala Gly Lys Thr Lys Glu Gly Val Leu Tyr Val Gly Ser Lys Thr
    50                  55                  60

Lys Glu Gly Val Val His Gly Val Ala Thr Val Ala Glu Lys Thr Lys
65                  70                  75                  80

Glu Gln Val Thr Asn Val Gly Gly Ala Val Val Thr Gly Val Thr Ala
                85                  90                  95

Val Ala Gln Lys Thr Val Glu Gly Ala Gly Ser Ile Ala Ala Ala Thr
            100                 105                 110

Gly Phe Val Lys Lys Asp Gln Leu Gly Lys Asn Glu Glu Gly Ala Pro
        115                 120                 125

Gln Glu Gly Ile Leu Glu Asp Met Pro Val Asp Pro Asp Asn Glu Ala
    130                 135                 140

Tyr Glu Met Pro Ser Glu Glu Gly Tyr Gln Asp Tyr Glu Pro Glu Ala
145                 150                 155                 160

<210> SEQ ID NO 5
<211> LENGTH: 140
<212> TYPE: PRT
<213> ORGANISM: Artificial Sequence
<220> FEATURE:
<223> OTHER INFORMATION: SNCA K23Q

<400> SEQUENCE: 5

Met Asp Val Phe Met Lys Gly Leu Ser Lys Ala Lys Glu Gly Val Val
1               5                   10                  15

Ala Ala Ala Glu Lys Thr Gln Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95
```

```
Lys Asp Gln Leu Gly Lys Asn Glu Glu Gly Ala Pro Gln Glu Gly Ile
        100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
    130                 135                 140

<210> SEQ ID NO 6
<211> LENGTH: 160
<212> TYPE: PRT
<213> ORGANISM: Artificial Sequence
<220> FEATURE:
<223> OTHER INFORMATION: 6XHis SNCA K23Q

<400> SEQUENCE: 6

Met Gly Ser Ser His His His His His His Ser Gly Leu Val Pro
1               5                   10                  15

Arg Gly Ser His Met Asp Val Phe Met Lys Gly Leu Ser Lys Ala Lys
            20                  25                  30

Glu Gly Val Val Ala Ala Ala Glu Lys Thr Gln Gln Gly Val Ala Glu
        35                  40                  45

Ala Ala Gly Lys Thr Lys Glu Gly Val Leu Tyr Val Gly Ser Lys Thr
    50                  55                  60

Lys Glu Gly Val Val His Gly Val Ala Thr Val Ala Glu Lys Thr Lys
65                  70                  75                  80

Glu Gln Val Thr Asn Val Gly Gly Ala Val Val Thr Gly Val Thr Ala
                85                  90                  95

Val Ala Gln Lys Thr Val Glu Gly Ala Gly Ser Ile Ala Ala Ala Thr
            100                 105                 110

Gly Phe Val Lys Lys Asp Gln Leu Gly Lys Asn Glu Glu Gly Ala Pro
        115                 120                 125

Gln Glu Gly Ile Leu Glu Asp Met Pro Val Asp Pro Asp Asn Glu Ala
    130                 135                 140

Tyr Glu Met Pro Ser Glu Glu Gly Tyr Gln Asp Tyr Glu Pro Glu Ala
145                 150                 155                 160

<210> SEQ ID NO 7
<211> LENGTH: 130
<212> TYPE: PRT
<213> ORGANISM: Artificial Sequence
<220> FEATURE:
<223> OTHER INFORMATION: SNCA del12

<400> SEQUENCE: 7

Met Lys Glu Gly Val Val Ala Ala Ala Glu Lys Thr Lys Gln Gly Val
1               5                   10                  15

Ala Glu Ala Ala Gly Lys Thr Lys Glu Gly Val Leu Tyr Val Gly Ser
            20                  25                  30

Lys Thr Lys Glu Gly Val Val His Gly Val Ala Thr Val Ala Glu Lys
        35                  40                  45

Thr Lys Glu Gln Val Thr Asn Val Gly Gly Ala Val Val Thr Gly Val
    50                  55                  60

Thr Ala Val Ala Gln Lys Thr Val Glu Gly Ala Gly Ser Ile Ala Ala
65                  70                  75                  80

Ala Thr Gly Phe Val Lys Lys Asp Gln Leu Gly Lys Asn Glu Glu Gly
                85                  90                  95

Ala Pro Gln Glu Gly Ile Leu Glu Asp Met Pro Val Asp Pro Asp Asn
```

```
                100                 105                 110
Glu Ala Tyr Glu Met Pro Ser Glu Glu Gly Tyr Gln Asp Tyr Glu Pro
            115                 120                 125
Glu Ala
    130

<210> SEQ ID NO 8
<211> LENGTH: 150
<212> TYPE: PRT
<213> ORGANISM: Artificial Sequence
<220> FEATURE:
<223> OTHER INFORMATION: 6XHis SNCA del12

<400> SEQUENCE: 8

Met Gly Ser Ser His His His His His His Ser Ser Gly Leu Val Pro
1               5                   10                  15

Arg Gly Ser His Met Lys Glu Gly Val Val Ala Ala Ala Glu Lys Thr
            20                  25                  30

Lys Gln Gly Val Ala Glu Ala Ala Gly Lys Thr Lys Glu Gly Val Leu
        35                  40                  45

Tyr Val Gly Ser Lys Thr Lys Glu Gly Val Val His Gly Val Ala Thr
    50                  55                  60

Val Ala Glu Lys Thr Lys Glu Gln Val Thr Asn Val Gly Gly Ala Val
65                  70                  75                  80

Val Thr Gly Val Thr Ala Val Ala Gln Lys Thr Val Glu Gly Ala Gly
                85                  90                  95

Ser Ile Ala Ala Ala Thr Gly Phe Val Lys Lys Asp Gln Leu Gly Lys
            100                 105                 110

Asn Glu Glu Gly Ala Pro Gln Glu Gly Ile Leu Glu Asp Met Pro Val
        115                 120                 125

Asp Pro Asp Asn Glu Ala Tyr Glu Met Pro Ser Glu Glu Gly Tyr Gln
    130                 135                 140

Asp Tyr Glu Pro Glu Ala
145                 150

<210> SEQ ID NO 9
<211> LENGTH: 140
<212> TYPE: PRT
<213> ORGANISM: Artificial Sequence
<220> FEATURE:
<223> OTHER INFORMATION: SNCA D2X
<220> FEATURE:
<221> NAME/KEY: misc_feature
<222> LOCATION: (2)..(2)
<223> OTHER INFORMATION: Xaa can be any naturally occurring amino acid

<400> SEQUENCE: 9

Met Xaa Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95
```

```
Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 10
<211> LENGTH: 160
<212> TYPE: PRT
<213> ORGANISM: Artificial Sequence
<220> FEATURE:
<223> OTHER INFORMATION: 6XHis SNCA D2X
<220> FEATURE:
<221> NAME/KEY: misc_feature
<222> LOCATION: (22)..(22)
<223> OTHER INFORMATION: Xaa can be any naturally occurring amino acid

<400> SEQUENCE: 10

Met Gly Ser Ser His His His His His His Ser Ser Gly Leu Val Pro
1               5                   10                  15

Arg Gly Ser His Met Xaa Val Phe Met Lys Gly Leu Ser Lys Ala Lys
            20                  25                  30

Glu Gly Val Val Ala Ala Ala Glu Lys Thr Lys Gln Gly Val Ala Glu
        35                  40                  45

Ala Ala Gly Lys Thr Lys Glu Gly Val Leu Tyr Val Gly Ser Lys Thr
    50                  55                  60

Lys Glu Gly Val Val His Gly Val Ala Thr Val Ala Glu Lys Thr Lys
65                  70                  75                  80

Glu Gln Val Thr Asn Val Gly Gly Ala Val Val Thr Gly Val Thr Ala
                85                  90                  95

Val Ala Gln Lys Thr Val Glu Gly Ala Gly Ser Ile Ala Ala Ala Thr
            100                 105                 110

Gly Phe Val Lys Lys Asp Gln Leu Gly Lys Asn Glu Glu Gly Ala Pro
        115                 120                 125

Gln Glu Gly Ile Leu Glu Asp Met Pro Val Asp Pro Asp Asn Glu Ala
    130                 135                 140

Tyr Glu Met Pro Ser Glu Glu Gly Tyr Gln Asp Tyr Glu Pro Glu Ala
145                 150                 155                 160

<210> SEQ ID NO 11
<211> LENGTH: 140
<212> TYPE: PRT
<213> ORGANISM: Artificial Sequence
<220> FEATURE:
<223> OTHER INFORMATION: SNCA K21X
<220> FEATURE:
<221> NAME/KEY: misc_feature
<222> LOCATION: (21)..(21)
<223> OTHER INFORMATION: Xaa can be any naturally occurring amino acid

<400> SEQUENCE: 11

Met Asp Val Phe Met Lys Gly Leu Ser Lys Ala Lys Glu Gly Val Val
1               5                   10                  15

Ala Ala Ala Glu Xaa Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60
```

```
Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
    130                 135                 140

<210> SEQ ID NO 12
<211> LENGTH: 160
<212> TYPE: PRT
<213> ORGANISM: Artificial Sequence
<220> FEATURE:
<223> OTHER INFORMATION: 6XHis SNCA K21X
<220> FEATURE:
<221> NAME/KEY: misc_feature
<222> LOCATION: (41)..(41)
<223> OTHER INFORMATION: Xaa can be any naturally occurring amino acid

<400> SEQUENCE: 12

Met Gly Ser Ser His His His His His His Ser Ser Gly Leu Val Pro
1               5                   10                  15

Arg Gly Ser His Met Asp Val Phe Met Lys Gly Leu Ser Lys Ala Lys
                20                  25                  30

Glu Gly Val Val Ala Ala Ala Glu Xaa Thr Lys Gln Gly Val Ala Glu
            35                  40                  45

Ala Ala Gly Lys Thr Lys Glu Gly Val Leu Tyr Val Gly Ser Lys Thr
    50                  55                  60

Lys Glu Gly Val Val His Gly Val Ala Thr Val Ala Glu Lys Thr Lys
65                  70                  75                  80

Glu Gln Val Thr Asn Val Gly Gly Ala Val Val Thr Gly Val Thr Ala
            85                  90                  95

Val Ala Gln Lys Thr Val Glu Gly Ala Gly Ser Ile Ala Ala Ala Thr
                100                 105                 110

Gly Phe Val Lys Lys Asp Gln Leu Gly Lys Asn Glu Glu Gly Ala Pro
            115                 120                 125

Gln Glu Gly Ile Leu Glu Asp Met Pro Val Asp Pro Asp Asn Glu Ala
    130                 135                 140

Tyr Glu Met Pro Ser Glu Glu Gly Tyr Gln Asp Tyr Glu Pro Glu Ala
145                 150                 155                 160

<210> SEQ ID NO 13
<211> LENGTH: 140
<212> TYPE: PRT
<213> ORGANISM: Artificial Sequence
<220> FEATURE:
<223> OTHER INFORMATION: SNCA K23X
<220> FEATURE:
<221> NAME/KEY: misc_feature
<222> LOCATION: (23)..(23)
<223> OTHER INFORMATION: Xaa can be any naturally occurring amino acid

<400> SEQUENCE: 13

Met Asp Val Phe Met Lys Gly Leu Ser Lys Ala Lys Glu Gly Val Val
1               5                   10                  15

Ala Ala Ala Glu Lys Thr Xaa Gln Gly Val Ala Glu Ala Ala Gly Lys
                20                  25                  30
```

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 14
<211> LENGTH: 160
<212> TYPE: PRT
<213> ORGANISM: Artificial Sequence
<220> FEATURE:
<223> OTHER INFORMATION: 6XHis SNCA K23X
<220> FEATURE:
<221> NAME/KEY: misc_feature
<222> LOCATION: (43)..(43)
<223> OTHER INFORMATION: Xaa can be any naturally occurring amino acid

<400> SEQUENCE: 14

Met Gly Ser Ser His His His His His His Ser Ser Gly Leu Val Pro
1               5                   10                  15

Arg Gly Ser His Met Asp Val Phe Met Lys Gly Leu Ser Lys Ala Lys
            20                  25                  30

Glu Gly Val Val Ala Ala Ala Glu Lys Thr Xaa Gln Gly Val Ala Glu
            35                  40                  45

Ala Ala Gly Lys Thr Lys Glu Gly Val Leu Tyr Val Gly Ser Lys Thr
    50                  55                  60

Lys Glu Gly Val Val His Gly Val Ala Thr Val Ala Glu Lys Thr Lys
65                  70                  75                  80

Glu Gln Val Thr Asn Val Gly Gly Ala Val Val Thr Gly Val Thr Ala
            85                  90                  95

Val Ala Gln Lys Thr Val Glu Gly Ala Gly Ser Ile Ala Ala Ala Thr
            100                 105                 110

Gly Phe Val Lys Lys Asp Gln Leu Gly Lys Asn Glu Glu Gly Ala Pro
            115                 120                 125

Gln Glu Gly Ile Leu Glu Asp Met Pro Val Asp Pro Asp Asn Glu Ala
            130                 135                 140

Tyr Glu Met Pro Ser Glu Glu Gly Tyr Gln Asp Tyr Glu Pro Glu Ala
145                 150                 155                 160

<210> SEQ ID NO 15
<211> LENGTH: 140
<212> TYPE: PRT
<213> ORGANISM: Artificial Sequence
<220> FEATURE:
<223> OTHER INFORMATION: SNCA K45X
<220> FEATURE:
<221> NAME/KEY: misc_feature
<222> LOCATION: (45)..(45)
<223> OTHER INFORMATION: Xaa can be any naturally occurring amino acid

<400> SEQUENCE: 15

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Xaa Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 16
<211> LENGTH: 160
<212> TYPE: PRT
<213> ORGANISM: Artificial Sequence
<220> FEATURE:
<223> OTHER INFORMATION: 6XHis SNCA K45X
<220> FEATURE:
<221> NAME/KEY: misc_feature
<222> LOCATION: (65)..(65)
<223> OTHER INFORMATION: Xaa can be any naturally occurring amino acid

<400> SEQUENCE: 16

Met Gly Ser Ser His His His His His His Ser Ser Gly Leu Val Pro
1               5                   10                  15

Arg Gly Ser His Met Asp Val Phe Met Lys Gly Leu Ser Lys Ala Lys
            20                  25                  30

Glu Gly Val Val Ala Ala Ala Glu Lys Thr Lys Gln Gly Val Ala Glu
        35                  40                  45

Ala Ala Gly Lys Thr Lys Glu Gly Val Leu Tyr Val Gly Ser Lys Thr
    50                  55                  60

Xaa Glu Gly Val Val His Gly Val Ala Thr Val Ala Glu Lys Thr Lys
65                  70                  75                  80

Glu Gln Val Thr Asn Val Gly Gly Ala Val Val Thr Gly Val Thr Ala
                85                  90                  95

Val Ala Gln Lys Thr Val Glu Gly Ala Gly Ser Ile Ala Ala Ala Thr
            100                 105                 110

Gly Phe Val Lys Lys Asp Gln Leu Gly Lys Asn Glu Glu Gly Ala Pro
        115                 120                 125

Gln Glu Gly Ile Leu Glu Asp Met Pro Val Asp Pro Asp Asn Glu Ala
    130                 135                 140

Tyr Glu Met Pro Ser Glu Glu Gly Tyr Gln Asp Tyr Glu Pro Glu Ala
145                 150                 155                 160

<210> SEQ ID NO 17
<211> LENGTH: 140
<212> TYPE: PRT
<213> ORGANISM: Artificial Sequence
<220> FEATURE:
<223> OTHER INFORMATION: SNCA T59X
<220> FEATURE:
<221> NAME/KEY: misc_feature
<222> LOCATION: (59)..(59)
<223> OTHER INFORMATION: Xaa can be any naturally occurring amino acid

<400> SEQUENCE: 17

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Xaa Lys Glu Gln Val Thr
50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 18
<211> LENGTH: 160
<212> TYPE: PRT
<213> ORGANISM: Artificial Sequence
<220> FEATURE:
<223> OTHER INFORMATION: 6XHis SNCA T59X
<220> FEATURE:
<221> NAME/KEY: misc_feature
<222> LOCATION: (79)..(79)
<223> OTHER INFORMATION: Xaa can be any naturally occurring amino acid

<400> SEQUENCE: 18

Met Gly Ser Ser His His His His His His Ser Ser Gly Leu Val Pro
1               5                   10                  15

Arg Gly Ser His Met Asp Val Phe Met Lys Gly Leu Ser Lys Ala Lys
            20                  25                  30

Glu Gly Val Val Ala Ala Ala Glu Lys Thr Lys Gln Gly Val Ala Glu
        35                  40                  45

Ala Ala Gly Lys Thr Lys Glu Gly Val Leu Tyr Val Gly Ser Lys Thr
50                  55                  60

Lys Glu Gly Val Val His Gly Val Ala Thr Val Ala Glu Lys Xaa Lys
65                  70                  75                  80

Glu Gln Val Thr Asn Val Gly Gly Ala Val Val Thr Gly Val Thr Ala
                85                  90                  95

Val Ala Gln Lys Thr Val Glu Gly Ala Gly Ser Ile Ala Ala Ala Thr
            100                 105                 110

Gly Phe Val Lys Lys Asp Gln Leu Gly Lys Asn Glu Glu Gly Ala Pro
        115                 120                 125

Gln Glu Gly Ile Leu Glu Asp Met Pro Val Asp Pro Asp Asn Glu Ala
    130                 135                 140

Tyr Glu Met Pro Ser Glu Glu Gly Tyr Gln Asp Tyr Glu Pro Glu Ala
145                 150                 155                 160

```
<210> SEQ ID NO 19
<211> LENGTH: 140
<212> TYPE: PRT
<213> ORGANISM: Artificial Sequence
<220> FEATURE:
<223> OTHER INFORMATION: SNCA G67X
<220> FEATURE:
<221> NAME/KEY: misc_feature
<222> LOCATION: (67)..(67)
<223> OTHER INFORMATION: Xaa can be any naturally occurring amino acid

<400> SEQUENCE: 19

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Xaa Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 20
<211> LENGTH: 160
<212> TYPE: PRT
<213> ORGANISM: Artificial Sequence
<220> FEATURE:
<223> OTHER INFORMATION: 6XHis SNCA G67X
<220> FEATURE:
<221> NAME/KEY: misc_feature
<222> LOCATION: (87)..(87)
<223> OTHER INFORMATION: Xaa can be any naturally occurring amino acid

<400> SEQUENCE: 20

Met Gly Ser Ser His His His His His His Ser Ser Gly Leu Val Pro
1               5                   10                  15

Arg Gly Ser His Met Asp Val Phe Met Lys Gly Leu Ser Lys Ala Lys
            20                  25                  30

Glu Gly Val Val Ala Ala Ala Glu Lys Thr Lys Gln Gly Val Ala Glu
        35                  40                  45

Ala Ala Gly Lys Thr Lys Glu Gly Val Leu Tyr Val Gly Ser Lys Thr
    50                  55                  60

Lys Glu Gly Val Val His Gly Val Ala Thr Val Ala Glu Lys Thr Lys
65                  70                  75                  80

Glu Gln Val Thr Asn Val Xaa Gly Ala Val Val Thr Gly Val Thr Ala
                85                  90                  95

Val Ala Gln Lys Thr Val Glu Gly Ala Gly Ser Ile Ala Ala Ala Thr
            100                 105                 110

Gly Phe Val Lys Lys Asp Gln Leu Gly Lys Asn Glu Glu Gly Ala Pro
        115                 120                 125

Gln Glu Gly Ile Leu Glu Asp Met Pro Val Asp Pro Asp Asn Glu Ala
```

```
                    130                 135                 140
Tyr Glu Met Pro Ser Glu Glu Gly Tyr Gln Asp Tyr Glu Pro Glu Ala
145                 150                 155                 160

<210> SEQ ID NO 21
<211> LENGTH: 140
<212> TYPE: PRT
<213> ORGANISM: Artificial Sequence
<220> FEATURE:
<223> OTHER INFORMATION: SNCA V77X
<220> FEATURE:
<221> NAME/KEY: misc_feature
<222> LOCATION: (77)..(77)
<223> OTHER INFORMATION: Xaa can be any naturally occurring amino acid

<400> SEQUENCE: 21

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Xaa Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 22
<211> LENGTH: 160
<212> TYPE: PRT
<213> ORGANISM: Artificial Sequence
<220> FEATURE:
<223> OTHER INFORMATION: 6XHis SNCA V77X
<220> FEATURE:
<221> NAME/KEY: misc_feature
<222> LOCATION: (97)..(97)
<223> OTHER INFORMATION: Xaa can be any naturally occurring amino acid

<400> SEQUENCE: 22

Met Gly Ser Ser His His His His His His Ser Ser Gly Leu Val Pro
1               5                   10                  15

Arg Gly Ser His Met Asp Val Phe Met Lys Gly Leu Ser Lys Ala Lys
                20                  25                  30

Glu Gly Val Val Ala Ala Ala Glu Lys Thr Lys Gln Gly Val Ala Glu
            35                  40                  45

Ala Ala Gly Lys Thr Lys Glu Gly Val Leu Tyr Val Gly Ser Lys Thr
    50                  55                  60

Lys Glu Gly Val Val His Gly Val Ala Thr Val Ala Glu Lys Thr Lys
65                  70                  75                  80

Glu Gln Val Thr Asn Val Gly Gly Ala Val Val Thr Gly Val Thr Ala
                85                  90                  95

Xaa Ala Gln Lys Thr Val Glu Gly Ala Gly Ser Ile Ala Ala Ala Thr
```

```
                    100                 105                 110
Gly Phe Val Lys Lys Asp Gln Leu Gly Lys Asn Glu Glu Gly Ala Pro
            115                 120                 125

Gln Glu Gly Ile Leu Glu Asp Met Pro Val Asp Pro Asp Asn Glu Ala
        130                 135                 140

Tyr Glu Met Pro Ser Glu Gly Tyr Gln Asp Tyr Glu Pro Glu Ala
145                 150                 155                 160

<210> SEQ ID NO 23
<211> LENGTH: 140
<212> TYPE: PRT
<213> ORGANISM: Artificial Sequence
<220> FEATURE:
<223> OTHER INFORMATION: SNCA A78X
<220> FEATURE:
<221> NAME/KEY: misc_feature
<222> LOCATION: (78)..(78)
<223> OTHER INFORMATION: Xaa can be any naturally occurring amino acid

<400> SEQUENCE: 23

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Xaa Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 24
<211> LENGTH: 160
<212> TYPE: PRT
<213> ORGANISM: Artificial Sequence
<220> FEATURE:
<223> OTHER INFORMATION: SNCA A78X
<220> FEATURE:
<221> NAME/KEY: misc_feature
<222> LOCATION: (98)..(98)
<223> OTHER INFORMATION: Xaa can be any naturally occurring amino acid

<400> SEQUENCE: 24

Met Gly Ser Ser His His His His His His Ser Ser Gly Leu Val Pro
1               5                   10                  15

Arg Gly Ser His Met Asp Val Phe Met Lys Gly Leu Ser Lys Ala Lys
            20                  25                  30

Glu Gly Val Val Ala Ala Ala Glu Lys Thr Lys Gln Gly Val Ala Glu
        35                  40                  45

Ala Ala Gly Lys Thr Lys Glu Gly Val Leu Tyr Val Gly Ser Lys Thr
    50                  55                  60

Lys Glu Gly Val Val His Gly Val Ala Thr Val Ala Glu Lys Thr Lys
```

```
                65                  70                  75                  80
Glu Gln Val Thr Asn Val Gly Gly Ala Val Val Thr Gly Val Thr Ala
                    85                  90                  95

Val Xaa Gln Lys Thr Val Glu Gly Ala Gly Ser Ile Ala Ala Ala Thr
                100                 105                 110

Gly Phe Val Lys Lys Asp Gln Leu Gly Lys Asn Glu Glu Gly Ala Pro
        115                 120                 125

Gln Glu Gly Ile Leu Glu Asp Met Pro Val Asp Pro Asp Asn Glu Ala
        130                 135                 140

Tyr Glu Met Pro Ser Glu Glu Gly Tyr Gln Asp Tyr Glu Pro Glu Ala
145                 150                 155                 160
```